US008486897B2

(12) United States Patent
Castelot-Deliencourt-Godefroy

(10) Patent No.: US 8,486,897 B2
(45) Date of Patent: Jul. 16, 2013

(54) C-ARYL GLYCOSIDE COMPOUNDS FOR THE TREATMENT OF DIABETES AND OBESITY

(75) Inventor: Géraldine Castelot-Deliencourt-Godefroy, Rouen (FR)

(73) Assignee: TFCHEM, Rouen (FR)

( * ) Notice: Subject to any disclaimer, the term of this patent is extended or adjusted under 35 U.S.C. 154(b) by 93 days.

(21) Appl. No.: 12/935,468

(22) PCT Filed: Apr. 2, 2009

(86) PCT No.: PCT/EP2009/053970
§ 371 (c)(1),
(2), (4) Date: Sep. 29, 2010

(87) PCT Pub. No.: WO2009/121939
PCT Pub. Date: Oct. 8, 2009

(65) Prior Publication Data
US 2011/0034402 A1    Feb. 10, 2011

(30) Foreign Application Priority Data

Apr. 2, 2008 (FR) ..................................... 08 52185

(51) Int. Cl.
*A61K 31/70* (2006.01)
*C07H 1/00* (2006.01)

(52) U.S. Cl.
USPC .......................................... 514/23; 536/1.11

(58) Field of Classification Search
USPC ........................................................ 536/1.1
See application file for complete search history.

(56) References Cited

U.S. PATENT DOCUMENTS

2006/0142206 A1   6/2006   Quirion et al.
2009/0318678 A1   12/2009  Castelot-Deliencourt-Godefroy et al.

FOREIGN PATENT DOCUMENTS

| WO | WO 01/27128 A1 | 4/2001 |
| WO | WO 01/74834 A1 | 10/2001 |
| WO | WO 2004/014928 A2 | 2/2004 |
| WO | WO-2005/012242 | 2/2005 |
| WO | WO 2005/044256 A1 | 5/2005 |
| WO | WO 2007/128899 A2 | 11/2007 |
| WO | WO-2009/117367 | 9/2009 |

OTHER PUBLICATIONS

International Search Report issued in application No. PCT/EP2009/053970 on Sep. 22, 2010.
French Search Report issued in application No. FR 0852185 on Jun. 19, 2008.
Arakawa et al., "Improved diabetic syndrome in C57BL/KSJ-db/db mice by oral administration of the Na+-glucose cotransporter inhibitor T-1095," British J. Pharma., 2001, pp. 578-586, vol. 132, No. 2.

Chen et al., "*E* and *Z* α-C-Galactosylceramides by Julia-Lythgoe-Kocienski Chemistry: A Test of the Receptor-Binding Model for Glycolipid Immunostimulants," ChemBioChem. 2006, pp. 1017-1022, vol. 7.
Deleuze et al., "Synthesis of *gem*-Difluorocarba-D-glucose: A Step Further in Sugar Mimesis," Angew. Chem. Int. Ed., 2004, pp. 6680-6683, vol. 43.
Finch et al., "Synthesis of [5.1]Metacyclophane," J. Org. Chem., 1979, pp. 2804-2805, vol. 44, No. 15.
Frixa et al., "Synthesis of *meso*-substituted porphyrins carrying carboranes and oligo(ethylene glycol) units for potential applications in boron neutron capture therapy," Org. Biomol. Chem., 2003, pp. 306-317, vol. 1.
Hatch et al., "Studies on Total Synthesis of the Olivomycins," J. Org. Chem., 1978, pp. 4172-4177, vol. 43, No. 21.
Houlton et al., "A Convenient Strategy for Replacement of the Anomeric Hydroxyl Group by Difluoromethyl Functionality in Carbohydrate Derivatives," Tetrahedron, 1993, pp. 8087-8106, vol. 49, No. 36.
Jin et al., "Increased Efficiencies of the Copolymers with Fluoro Groups in Vinylene Units," Macromolecules, 2007, pp. 6799-6806, vol. 40, No. 19.
Jin et al., "Synthesis and electroluminescent properties of copolymers based on PPV with Fluoro groups in vinylene units," Polymer, 2007, pp. 1541-1549, vol. 48.
Johannsson et al., "Growth Hormone Treatment of Abdominally Obese Men Reduces Abdominal Fat Mass, Improves Glucose and Lipoprotein Metabolism, and Reduces Diastolic Blood Pressure," J. Clin. Endocrinol. Metab., 1997, pp. 727-734, vol. 82, No. 3, doi: 10.1210/jc.82.3.727.
Kahn et al., "Normalization of Blood Glucose in Diabetic Rats with Phlorizin Treatment Reverses Insulin-resistant Glucose Transport in Adipose Cells without Restoring Glucose Transporter Gene Expression," J. Clin. Invest., Feb. 1991, pp. 561-570, vol. 87.
Kolympadi et al., "Synthesis and Conformational Analysis of (α-D-Galactosyl)phenylmethane and α-,β-Difluoromethane Analogues: Interactions with the Plant Lectin Viscumin," Chem. Eur. J., 2009, pp. 2861-2873, vol. 15.
Kuroboshi et al., "Oxidative Desulfurization-Fluorination: A Facile Entry to a Wide Variety of Organofluorine Compounds Leading to Novel Liquid-Crystalline Materials," Adv. Synth. Catal., 2001, pp. 235-250, vol. 343, No. 3.
Kuzuhara et al., "Syntheses with Partially Benzylated Sugars. VIII. Substitution at C-5 in an Aldose. The Synthesis of 5-*O*-Methyl-D-glucofuranose Derivatives," Aug. 1967, pp. 2531-2534, vol. 32.
Labé guère et al., "An efficient diastereoselective synthesis of β-1-formyl-2,3,4,6-tetra-*O*-benzyl-D-glucopyranoside," Tetrahedron Letters, 2002, 7271-7272, vol. 43.

(Continued)

*Primary Examiner* — Elli Peselev
(74) *Attorney, Agent, or Firm* — Foley & Lardner LLP

(57) ABSTRACT

Compounds of formula (I) and pharmaceutically acceptable salts thereof, for use in the prevention and treatment of diseases including diabetes.

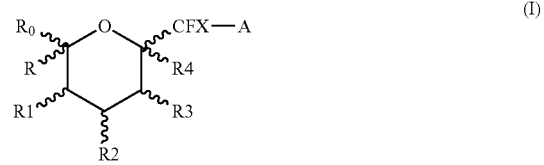

(I)

19 Claims, No Drawings

OTHER PUBLICATIONS

Magueur et al., "Fluoro-artemisinins: When a *gem*-difluoroethylene replaces a carbonyl group," J. Fluorine Chem., 2006, pp. 637-642, vol. 127.

Motherwell et al., "A Convenient Method for Replacement of the Anomeric Hydroxy Group in Carbohydrates by Difluoromethyl Functionality," J. Chem. Soc., Chem., Commun., 1989, pp. 1437-1439.

Peters et al., "On the Illusive Nature of o-Formylazobenzenes: Exploiting the Nucleophilicity of the Azo Group for Cyclization to Indazole Derivatives," J. Org. Chem., 2006, pp. 7840-7845, vol. 71, No. 20.

Risseeuw et al., "Synthesis of alkylated sugar amino acids: conformationally restricted L-Xaa-L-Ser/Thr mimics," Org. Biomol. Chem., 2007, pp. 2311-2314, vol. 5.

Rossetti et al., "Correction of Hyperglycemia with Phlorizin Normalizes Tissue Sensitivity to Insulin in Diabetic Rats," 1986, pp. 1510-1515.

Rossetti et al., "Effect of Chronic Hyperglycemia on In Vivo Insulin Secretion in Partially Pancreatectomized Rats," J. Clin. Invest., Oct. 1987, pp. 1037-1044, vol. 80.

Sàanchez et al., "Convenient Methods for the Synthesis of β-C-Glycosyl Aldehydes," Synlett, Sep. 1994, pp. 705-708.

Tony et al., "Synthesis of β-*C-galacto*-Pyranosides with Fluorine on the Pseudoanomeric Substituent," Organic Letters, 2007, pp. 1441-1444, vol. 9, No. 8.

Toyota et al., "Intramolecular C=O•••B Interactions in *o*-Boron Substituted Benzaldehyde, Aceotphenone, and Benzophenone," Bull. Chem. Soc. Jpn., 2002, pp. 2667-2671, vol. 75, No. 12.

Tsujihara et al., "$Na^+$-Glucose Cotransporter (SGLT) Inhibitors as Antidiabetic Agents. 4. Synthesis and Pharmacological Properties of 4'-Dehydroxyphlorizin Derivatives Substituted on the B Ring," J. Med. Chem., 1999, pp. 5311-5324, vol. 42, No. 26.

Zeitouni et al., "A convenient new route to protected and free 2,6-anhydro-D-glycero-D-gulo-heptoses (1-formyl-β-D-glucopyranosides)," Tetrahedron Letters, 2004, pp. 7761-7763, vol. 45.

Zhu et al., "Synthesis of a C-Disaccharide Analog of the Thomsen-Friedenreich (T) Epitope," Synlett 2001, pp. 79-81, No. 1.

Greene—"Protective Groups in Organic Synthesis", John Wiley & Sons, New York (1981), Chapter 2.

White, John R. "Apple Trees to Sodium Glucose Co-Transporter Inhibitors: A Review of SGLT2 Inhibition", Clinical Diabetes, vol. 28, Nov. 1, 2010.

Yagi et al., "Inhibition of Mushroom-Tyrosinase by *Aloe* extract", *Planta Med*, Dec. 1987, pp. 515-517, vol. 53, Issue 6.

Maeda et al., "In vitro effectiveness of several whitening cosmetic components in human melanocytes", *J. Soc. Cosmet. Chem.*, 1991, pp. 361-368, vol. 42.

Tsang et al., "Tyrosinase Inhibitors from Crude Drugs," *Biol. Pharm. Bull.*, 1994, pp. 266-269, vol. 17, Issue 2.

C-ARYL GLYCOSIDE COMPOUNDS FOR THE TREATMENT OF DIABETES AND OBESITY

This invention relates to a family of fluorinated C-aryl glycoside compounds, the process for their preparation, as well as the application of same in the pharmaceutical and cosmetics fields, in particular for the treatment of diabetes and obesity.

Sugars and the derivatives thereof constitute one of the most common classes of compounds in nature. Based on their chemical structures, they exhibit various physicochemical properties and can play a key role in a wide variety of biological processes.

In recent years, there has been a growing interest in discovering new glycosides having advantageous properties in terms of improved efficacy, selectivity and stability.

Found among these compounds, in particular, are aryl glycosides or phenol glycosides having applications in the field of cosmetics or in the treatment or prevention of diseases such as diabetes, obesity, cancer, inflammatory diseases, auto-immune diseases, infections, thromboses, and with regard to numerous other therapeutic fields. By their biological properties and their structure, these compounds interest numerous research teams.

Phlorizin may be cited in particular, as a molecule known for its inhibiting activity with regard to sodium-dependent glucose co-transporters (SGLT) (Journal of Clinical Investigation, vol. 79, p. 1510, (1987); ibid., vol. 80, p. 1037 (1987); ibid., vol. 87, p. 561 (1991); J. of Med. Chem., vol. 42, p. 5311 (1999); British Journal of Pharmacology, vol. 132, p. 578, (2001)).

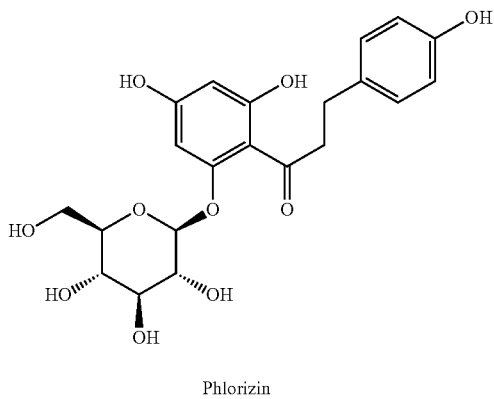 [SMILES: O=C(CCc1ccc(O)cc1)c1c(O)cc(O)cc1O[C@@H]1O[C@H](CO)[C@@H](O)[C@H](O)[C@H]1O]

Phlorizin

Inhibitors of sodium-dependent glucose co-transporters (SGLT), found in particular in the intestines and kidney, are potentially usable for treating diabetes, and more specifically type-II diabetes, but also for hyperglycemia, hyperinsulinemia, obesity, hypertriglyceridemia, syndrome X (also known by the name of metabolic syndrome, J. of Clin. Endocrinol. Metabol., 82, 727-734 (1997)), diabetes-related complications or else atherosclerosis. As a matter of fact, it is known that hyperglycemia participates in the onset and evolution of diabetes and leads to a reduction in the secretion of insulin and a reduction in insulin sensitivity, which results in an increase in the glucose level, thereby exacerbating diabetes. The treatment of hyperglycemia can thus be considered as a mean to treat diabetes.

Such being the case, one of the methods for treating hyperglycemia is to promote the excretion of excess of glucose directly into the urine, e.g., by inhibiting the sodium-dependent glucose co-transporter in the proximal tubules of the kidneys, the effect of which is to inhibit the re-absorption of glucose and to thereby promote the excretion thereof into the urine, leading thus to a reduction in the blood-sugar level.

At present, a large number of drugs exist, which can be used for treating diabetes, such as biguanides, sulfonylureas, insulin resistance-improving agents, and inhibitors of α-glycosidases. However, these compounds have numerous side effects, thereby increasing the need for new drugs.

Therefore, the invention relates to C-aryl glycoside compounds, which are useful, in particular, for the treatment of diabetes.

These compounds are analogues of O-aryl glycosides or phenol glycosides, wherein the anomeric oxygen is replaced by a carbon atom, carrying one or two fluorine atom(s), and have the distinctive feature of being stable analogues of O-aryl glycosides, which are stable when confronted with enzymatic degradation processes, in particular via glycosidase-type enzymes. Moreover, the mono or difluorinated carbon is a better mimic of oxygen than a $CH_2$ group.

Thus, contrary to the $CH_2$-glycosides, the replacement of the anomeric oxygen by a $CF_2$ or a CFH group, in particular minimizes the electronic effects due to the substitution, while at the same time resulting in stable compounds, resistant when confronted with enzymatic degradations, and in particular via glycosidase-type enzymes, but also resistant to hydrolysis condition in acidic or basic media.

C-fluorinated-glycoside compounds substituted at the anomeric position by an alkyl chain possibly substituted are described in the patent applications WO 2004/014 928 and WO 2007/128 899 but no biological activity of these compounds with regard to inhibiting SGLT is demonstrated in these applications. Moreover, no C-aryl glycoside compound is described, such a compound being not obtainable by a process such as described in these patent applications.

The inventors have thus developed new synthetic approaches enabling access to C-aryl glycoside compounds, compounds useful as SGLT inhibitors, in particular for the treatment of diabetes and obesity.

Therefore, the object of the present invention is a compound having the generic formula (I):

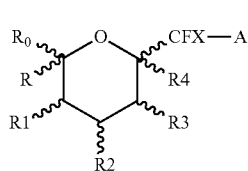

or a pharmaceutically acceptable salt thereof, a tautomer, an isomer or a mixture of isomers in any proportion, in particular a mixture of enantiomers, and particularly a racemate mixture, wherein:

X represents a hydrogen or a fluorine atom;

R represents a hydrogen or a fluorine atom or a $CH_3$, $CH_2F$, $CH_2OH$, $CH_2OSiR^aR^bR^c$, $CH_2OR^{11}$, $CH_2OCOR^{11}$, $CH_2OCO_2R^{11}$, $CH_2OCONR^{12}R^{13}$, $CH_2OP(O)(OR^{14})_2$ or $CH_2OSO_3R^{14}$ group;

R1 and R2 represent, independently from one another, a fluorine atom or an OH, $OSiR^aR^bR^c$, $OR^{11}$, $OCOR^{11}$, $OCO_2R^{11}$ or $OCONR^{12}R^{13}$ group;

R3 represents a hydrogen or fluorine atom or an OH, OSiR$^a$R$^b$R$^c$, OR$^{11}$, OCOR$^{11}$, OCO$_2$R$^{11}$, OCONR$^{12}$R$^{13}$, NR$^{12}$R$^{13}$ or NR$^{12}$COR$^{11}$ group;

R4 represents a hydrogen atom, an halogen atom or an OH, OSiR$^a$R$^b$R$^c$, OR$^{11}$, OCOR$^{11}$, OCO$_2$R$^{11}$, OCONR$^{12}$R$^{13}$, NR$^{12}$R$^{13}$, (C$_1$-C$_6$)-alkyl or (C$_2$-C$_6$)-alkenyl group;

R$_0$ represents a hydrogen or an halogen atom or an OH, OSiR$^a$R$^b$R$^c$, OR$^{11}$, OCOR$^{11}$, OCO$_2$R$^{11}$, OCONR$^{12}$R$^{13}$, OP(O)(OR$^{14}$)$_2$ or OSO$_3$R$^{14}$ group;

or R and R1, together with the carbon atoms carrying them, form a cyclic acetal having the following formula:

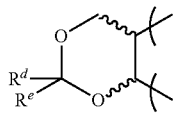

and/or (R$_0$ and R1), (R1 and R2), (R2 and R3), and/or (R3 and R4), together with the carbon atoms carrying them, form a cyclic acetal having the following formula:

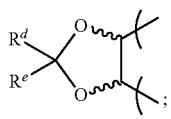

and

A represents an aryl, heteroaryl or aryl-(C$_1$-C$_6$)-alkyl-aryl group, possibly substituted by one or more groups chosen among an halogen atom, a CN, SO$_2$, SiR$^a$R$^b$R$^c$, (C$_1$-C$_6$)-alkyl, (C$_2$-C$_6$)-alkenyl, (C$_2$-C$_6$)-alkynyl, (C$_3$-C$_7$)-cycloalkyl, 5 to 7 ring-membered heterocycloalkyl, aryl, heteroaryl, aryl-(C$_1$-C$_6$)-alkyl, heteroaryl-(C$_1$-C$_6$)-alkyl, (C$_1$-C$_6$)-alkyl-aryl, (C$_1$-C$_6$)-alkyl-heteroaryl, OR$^{11}$, COR$^{11}$, OCOR$^{11}$, CO$_2$R$^{11}$, NR$^{12}$R$^{13}$, NR$^{12}$COR$^{11}$, CONR$^{12}$R$^{13}$, SR$^{11}$, SO$_2$R$^{11}$, CSR$^{11}$ and OSO$_3$R$^{11}$ group, the whole being possibly substituted by one or more groups chosen among an halogen atom, an OH, (C$_1$-C$_6$)-alkyl, (C$_1$-C$_6$)-alkoxy, COOH and CHO group;

with:

R$^{11}$ representing a (C$_1$-C$_6$)-alkyl, (C$_2$-C$_6$)-alkenyl, (C$_2$-C$_6$)-alkynyl, (C$_3$-C$_7$)-cycloalkyl, 5 to 7 ring-membered heterocycloalkyl, aryl, aryl-(C$_1$-C$_6$)-alkyl or (C$_1$-C$_6$)-alkyl-aryl group, this group being possibly substituted by one or more groups chosen among an halogen atom, an OH, COOH and CHO group;

R$^{12}$ and R$^{13}$ representing, independently from one another, a hydrogen atom or a (C$_1$-C$_6$)-alkyl or aryl-(C$_1$-C$_6$)-alkyl group;

R$^{14}$ representing a hydrogen atom or a (C$_1$-C$_6$)-alkyl group;

R$^a$, R$^b$ and R$^c$ representing, independently from one another, a (C$_1$-C$_6$)-alkyl, aryl or aryl-(C$_1$-C$_6$)-alkyl group; and R$^d$ and R$^e$ representing, independently from one another, a hydrogen atom or a (C$_1$-C$_6$)-alkyl group;

with the proviso that when R$_0$ is different from a hydrogen atom, then R4 represents a hydrogen atom, and with the proviso that the compound of formula (I) is not the following compound:

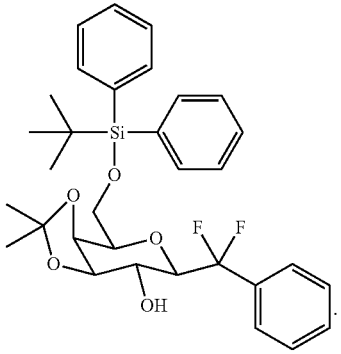 [SMILES: CC1(C)OC2C(CO[Si](c3ccccc3)(c3ccccc3)C(C)(C)C)OC(C(F)(F)c3ccccc3)C(O)C2O1]

The silylated compound cited above is described in Kurissery et al. (*Org. Lett.* 2007, 9, 8, 1441-1444) as synthesis intermediate. No biological activity of this compound is described or suggested in this publication.

In this invention, "pharmaceutically acceptable" is understood to mean what is useful in the preparation of a pharmaceutical composition which is generally safe, non-toxic and neither biologically nor otherwise undesirable and which is acceptable for veterinary as well as human pharmaceutical use.

In this invention, "pharmaceutically acceptable salts" of a compound, is understood to designate salts which are pharmaceutically acceptable, as defined herein, and which possess the desired pharmacological activity of the parent compound. Such salts include:

(1) hydrates and solvates, (2) acid addition salts formed with inorganic acids such as hydrochloric acid, bromhydric acid, sulphuric acid, nitric acid, phosphoric acid or the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, mandelic acid, methanesulfonic acid, muconic acid, 2-naphtalenesulfonic acid, propionic acid, salicylic acid, succinic acid, dibenzoyl-L-tartaric acid, tartaric acid, p-toluenesulfonic acid, trimethylacetic acid, trifluoroacetic acid and the like; and (3) salts formed when an acid proton present in the parent compound is either replaced by a metal ion, e.g., an alkali metal ion (e.g., Na$^+$, K$^+$ or Li$^+$), an alkaline-earth metal ion (like Ca$^{2+}$ or Mg$^{2+}$) or an aluminium ion; or coordinates with an organic or inorganic base. Acceptable organic bases include diethanolamine, ethanolamine, N-methylglucamine, triethanolamine, tromethamine and the like. Acceptable inorganic bases include aluminium hydroxide, calcium hydroxide, potassium hydroxide, sodium carbonate and sodium hydroxide.

In this invention, "tautomer" is understood to designate the various tautomer forms that the sugar of compound (1) may assume, namely a pyranose (6-membered ring), furanose (5-membered ring) or linear (open form) form, and also the various tautomer forms that could be observed with a ketone moiety, when it is present on the molecule, such as a cyclisation between an hydroxyle group and the ketone moiety.

However, the compounds of the invention can assume various tautomer forms only when the radical R4 represents an OH group, R1 having also to represent an OH group in order that the compounds of the invention can be in the furanose form.

Thus, for example, in the galactose series, the compounds of the invention might appear under the following various forms:

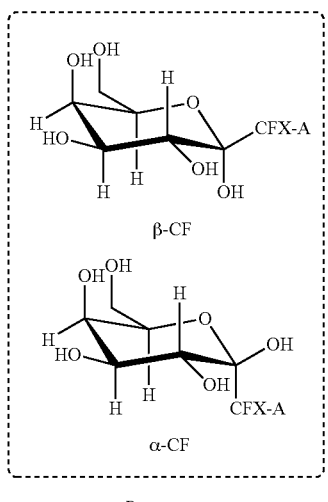

Pyranoses

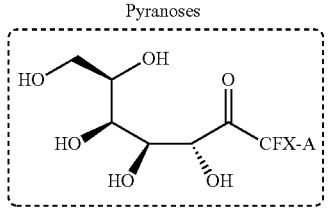

Linear

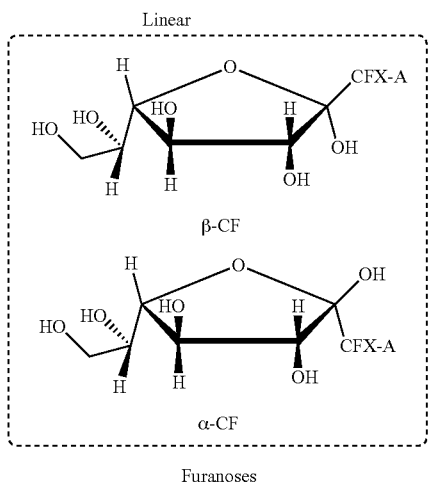

Furanoses

The anomeric carbon can thus appear in two different configurations in the closed pyranose and furanose forms.

The compounds of the invention can thus assume different tautomer forms which can be present in solution in equilibrium, with optionally a major tautomer form relatively to the other(s) tautomer form(s), or the compounds of the invention can assume only one tautomer form, such as only a furanose form, in some cases.

In this last case where the sugar assumes only one tautomer form, it is thus possible to block the configuration of the sugar to this tautomer form when R4=OH is transformed, notably by substitution of the OH group or conversion in a hydrogen or halogen atom.

In the case of the presence of OH and C=O functionalities in the same molecule, the following tautomer forms (open and cyclized) can be observed:

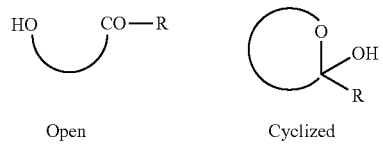

Open      Cyclized

In this invention, "isomers," within the meaning of this invention, is understood to designate diastereoisomers or enantiomers. These are therefore optical isomers also referred to as "stereoisomers". Stereoisomers which are not mirror images of one another are thus designated as "diastereoisomers," and stereoisomers which are non-superimposable mirror images are designated as "enantiomers".

Notably, the sugar moiety of the compounds of the invention can belong to the D or L series, and preferably to the D series.

A carbon atom bound to four non-identical substituents is called a "chiral centre".

An equimolar mixture of two enantiomers is called a racemate mixture.

Within the meaning of this invention, "halogen" is understood to mean an atom of fluorine, bromine, chlorine or iodine. Advantageously, this is an atom of fluorine, bromine or chlorine.

Within the meaning of this invention, "$(C_1-C_6)$-alkyl" group is understood to mean a saturated, linear or branched hydrocarbon chain comprising from 1 to 6 carbon atoms, in particular the methyl, ethyl, n-propyl, isopropyl, n-butyl, isobutyl, sec-butyl, tert-butyl, n-pentyl, n-hexyl groups.

Within the meaning of this invention, "$(C_1-C_6)$-alkoxy" group is understood to mean a $(C_1-C_6)$-alkyl group as defined above, which is bound to the molecule by means of an oxygen atom. It can be, in particular, a methoxy, ethoxy, n-propoxy, isopropoxy, n-butoxy, iso-butoxy, sec-butoxy, tert-butoxy, n-pentoxy or n-hexoxy group.

Within the meaning of this invention, "$(C_2-C_6)$-alkenyl" group is understood to mean a linear or branched hydrocarbon chain comprising at least one double bond and comprising from 2 to 6 carbon atoms, e.g., such as an ethenyl (vinyl) or propenyl group.

Within the meaning of the invention, "$(C_2-C_6)$-alkynyl" group is understood to mean a linear or branched hydrocarbon chain comprising at least one triple bond and comprising from 2 to 6 carbon atoms, e.g., such as an ethynyl or propynyl group.

Within the meaning of this invention, "$(C_3-C_7)$-cycloalkyl" group is understood to mean a saturated hydrocarbon ring comprising from 3 to 7, advantageously from 5 to 7, carbon atoms, in particular the cyclohexyl, cyclopentyl or cycloheptyl group.

Within the meaning of this invention, "heterocycloalkyl" group is understood to mean a saturated hydrocarbon ring having 5 to 7 members and containing one or more, advantageously one or two, heteroatoms, e.g., such as sulphur, nitrogen or oxygen atoms, e.g., such as the tetrahydrofuranyl, piperidinyl, pyrrolidinyl, tetrahydropyranyl, 1,3-dioxolanyl group.

Within the meaning of this invention, "aryl" group is understood to mean an aromatic group preferably comprising from 5 to 10 carbon atoms and including one or more fused rings, e.g., such as a phenyl or naphtyl group. This is advantageously phenyl.

Within the meaning of the invention, "heteroaryl" group is understood to mean any aryl group as defined above wherein one or more carbon atoms have been replaced by one or more heteroatoms, advantageously 1 to 4, and even more advantageously 1 to 2, e.g., such as sulphur, nitrogen or oxygen atoms. Examples of heteroaryl groups are the furyl, thiophenyl, pyrrolyl, pyridyl, pyrimidyl, pyrazolyl, imidazolyl, tetrazolyl or else indyl groups.

Within the meaning of this invention, "aryl-$(C_1$-$C_6)$-alkyl" group is understood to mean any aryl group as defined above, which is bound to the molecule by means of a $(C_1$-$C_6)$-alkyl group as defined above. In particular, a group such as this can be a benzyl group.

Within the meaning of this invention, "heteroaryl-$(C_1$-$C_6)$-alkyl" group is understood to mean a heteroaryl group as defined above, which is bound to the molecule by means of a $(C_1$-$C_6)$-alkyl group as defined above.

Within the meaning of this invention, "$(C_1$-$C_6)$-alkyl-aryl" group is understood to mean a $(C_1$-$C_6)$-alkyl group as defined above, which is bound to the molecule by means of an aryl group as defined above. In particular, a group such as this can be a methylphenyl group.

Within the meaning of this invention, "$(C_1$-$C_6)$-alkyl-heteroaryl" group is understood to mean a $(C_1$-$C_6)$-alkyl group as defined above, which is bound to the molecule by means of a heteroaryl group as defined above.

Within the meaning of this invention, "aryl-$(C_1$-$C_6)$-alkyl-aryl" group is understood to mean an aryl-$(C_1$-$C_6)$-alkyl group as defined above, which is bound to the molecule by means of an aryl group as defined above. In particular, such a group can be a benzyl-phenyl group.

According to a preferred embodiment, $R_0$ represents a hydrogen atom or an OH group and preferably a hydrogen atom. In this last case, when $R_0$=H, the compounds of the invention respond to the following formula (Ia):

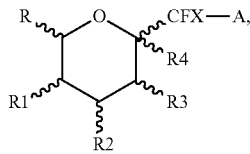

(Ia)

with R, R1, R2, R3, R4, X and A as defined above.

The compounds of the invention are advantageously based on the following formulas (Ibis) or (Iter):

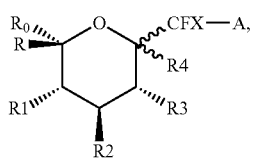

(Ibis)

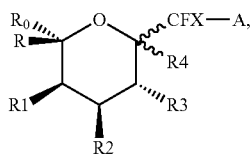

(Iter)

with R, R1, R2, R3, R4, $R_0$, X and A as defined above.

The compounds of the invention are advantageously based on the formula (Ibis).

Moreover, the compounds of the invention can also be based on the following formulas (Iquater) and (Ia-quarter), when R=H:

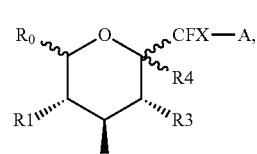

(Iquater)

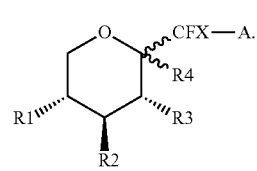

(Ia-quater)

The compounds of the invention are more advantageously based on the following formulas (Ia-bis) or (Ia-ter):

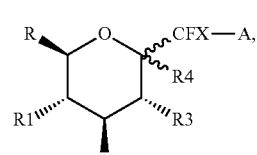

(Ia-bis)

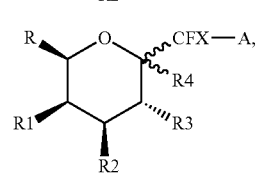

(Ia-ter)

with R, R1, R2, R3, R4, X and A as defined above.

The compounds of the invention are more advantageously based on the formula (Ia-bis).

According to a particular embodiment of the invention, A represents an aryl or heteroaryl group, possibly substituted by one or more groups chosen among an halogen atom, a CN, $SO_2$, $SiR^aR^bR^c$, $(C_1$-$C_6)$-alkyl, $(C_2$-$C_6)$-alkenyl, $(C_2$-$C_6)$-alkynyl, $(C_3$-$C_7)$-cycloalkyl, 5 to 7 ring-membered heterocycloalkyl, aryl, heteroaryl, aryl-$(C_1$-$C_6)$-alkyl, heteroaryl-$(C_1$-$C_6)$-alkyl, $(C_1$-$C_6)$-alkyl-aryl, $(C_1$-$C_6)$-alkyl-heteroaryl, $OR^{11}$, $COR^{11}$, $OCOR^{11}$, $CO_2R^{11}$, $NR^{12}R^{13}$, $CONR^{12}R^{13}$, $SR^{11}$, $SO_2R^{11}$, $CSR^{11}$ and $OSO_3R^{11}$ group, the whole being possibly substituted by one or more groups chosen among an halogen atom, an OH, COOH and CHO group, $R^a$, $R^b$, $R^c$, $R^{11}$, $R^{12}$ and $R^{13}$ being as defined above.

Advantageously, A represents a phenyl or benzylphenyl group, possibly substituted by one or more groups chosen among an halogen atom, a CN, $SO_2$, $SiR^aR^bR^c$, $(C_1$-$C_6)$-alkyl, $(C_2$-$C_6)$-alkenyl, $(C_2$-$C_6)$-alkynyl, $(C_3$-$C_7)$-cycloalkyl, 5 to 7 ring-membered heterocycloalkyl, aryl, heteroaryl, aryl-$(C_1$-$C_6)$-alkyl, heteroaryl-$(C_1$-$C_6)$-alkyl, $(C_1$-$C_6)$-alkyl-aryl, $(C_1$-$C_6)$-alkyl-heteroaryl, $OR^{11}$, $COR^{11}$, $OCOR^{11}$, $CO_2R^{11}$, $NR^{12}R^{13}$, $NR^{12}COR^{11}$, $CONR^{12}R^{13}$, $SR^{11}$, $SO_2R^{11}$, $CSR^{11}$ and $OSO_3R^{11}$ group, the whole being possibly substituted by one or more groups chosen among an halogen atom, an OH, $(C_1$-$C_6)$-alkyl, $(C_1$-$C_6)$-alkoxy, COOH and CHO group, $R^a$, $R^b$, $R^c$, $R^{11}$, $R^{12}$ and $R^{13}$ being as defined above.

In an equally advantageously manner, the radical A represents a phenyl group possibly substituted by one or more groups chosen among an halogen atom, a CN, $SO_2$, $SiR^aR^bR^c$, $(C_1$-$C_6)$-alkyl, $(C_2$-$C_6)$-alkenyl, $(C_2$-$C_6)$-alkynyl, $(C_3$-$C_7)$-cycloalkyl, 5 to 7 ring-membered heterocycloalkyl, aryl, heteroaryl, aryl-$(C_1-C_6)$-alkyl, heteroaryl-$(C_1-C_6)$-alkyl, $(C_1-C_6)$-alkyl-aryl, $(C_1-C_6)$-alkyl-heteroaryl, $OR^{11}$, $COR^{10}$, $OCOR^{11}$, $CO_2R^{11}$, $NR^{12}R^{13}$, $CONR^{12}R^{13}$, $SR^{11}$, $SO_2R^{11}$, $CSR^{11}$ and $OSO_3R^{11}$ group, the whole being possibly substituted by one or more groups chosen among an halogen atom, an OH, $(C_1-C_6)$-alkyl, $(C_1-C_6)$-alkoxy, COOH and CHO group, and notably among an halogen atom, an OH, COOH and CHO group, $R^a$, $R^b$, $R^c$, $R^{11}$, $R^{12}$ and $R^{13}$ being as defined above.

Consequently, according to a first particular embodiment of the invention, a compound of the invention is advantageously based on the following generic formula (II), and more advantageously based on the following generic formula (IIa):

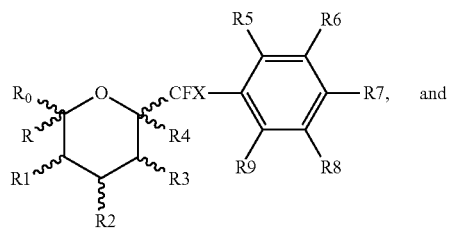
(II)

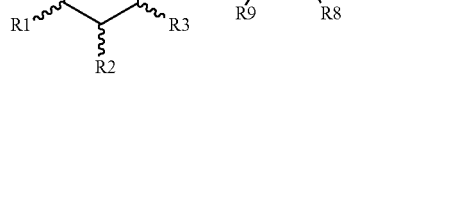
(IIa)

wherein:

R5, R6, R7, R8 and R9 represent, independently from one another, a hydrogen atom, an halogen atom, a CN, $SO_2$, $SiR^aR^bR^c$, $(C_1-C_6)$-alkyl, $(C_2-C_6)$-alkenyl, $(C_2-C_6)$-alkynyl, $(C_3-C_7)$-cycloalkyl, 5 to 7 ring-membered heterocycloalkyl, aryl, heteroaryl, aryl-$(C_1-C_6)$-alkyl, hetero aryl-$(C_1-C_6)$-alkyl, $(C_1-C_6)$-alkyl-aryl, $(C_1-C_6)$-alkyl-hetero aryl, $OR^{11}$, $COR^{11}$, $OCOR^{11}$, $CO_2R^{11}$, $NR^{12}R^{13}$, $NR^{12}COR^{11}$, $CONR^{12}R^{13}$, $SR^{11}$, $SO_2R^{11}$, $CSR^{11}$ or $OSO_3R^{11}$ group, the said group being possibly substituted by one or more groups chosen among an halogen atom, an OH, $(C_1-C_6)$-alkyl, $(C_1-C_6)$-alkoxy, COOH and CHO group; and in particular by one or more groups chosen among an halogen atom, an OH, COOH and CHO group, and X, R, R1, R2, R3, R4, $R_0$, $R^{11}$, $R^{12}$ and $R^{13}$ are as defined above.

Thus, compound of formula (IIa) corresponds to a compound of formula (II) wherein $R_0$=H.

According to a second particular embodiment of the invention, a compound of the invention is advantageously based on the following generic formula (IIbis), and more advantageously based on the following generic formula (IIa-bis):

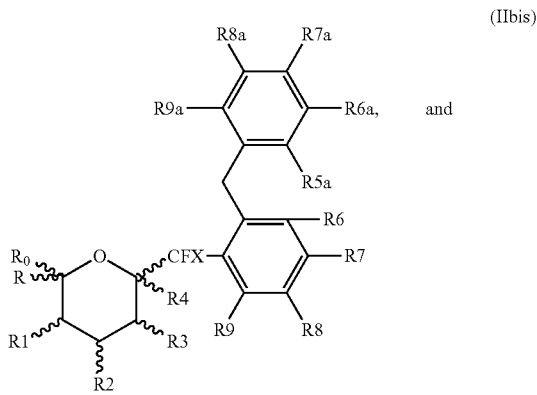
(IIbis)

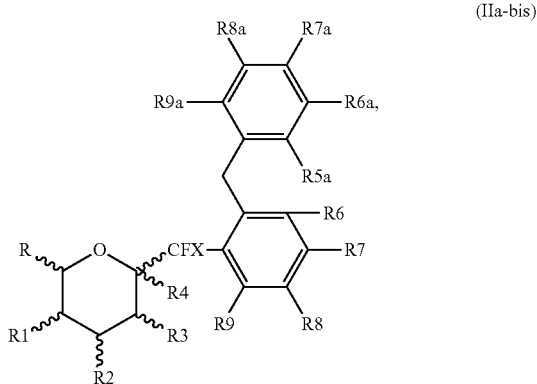
(IIa-bis)

wherein:

R6, R7, R8, R9, R5a, R6a, R7a, R8a and R9a represent, independently from one another, a hydrogen atom, an halogen atom, a CN, $SO_2$, $SiR^aR^bR^c$, $(C_1-C_6)$-alkyl, $(C_2-C_6)$-alkenyl, $(C_2-C_6)$-alkynyl, $(C_3-C_7)$-cycloalkyl, 5 to 7 ring-membered heterocycloalkyl, aryl, heteroaryl, aryl-$(C_1-C_6)$-alkyl, heteroaryl-$(C_1-C_6)$-alkyl, $(C_1-C_6)$-alkyl-aryl, $(C_1-C_6)$-alkyl-heteroaryl, $OR^{11}$, $COR^{11}$, $OCOR^{11}$, $CO_2R^{11}$, $NR^{12}R^{13}$, $NR^{12}COR^{11}$, $CONR^{12}R^{13}$, $SR^{11}$, $SO_2R^{11}$, $CSR^{11}$ or $OSO_3R^{11}$ group, the said group being possibly substituted by one or more groups chosen among an halogen atom, an OH, $(C_1-C_6)$-alkyl, $(C_1-C_6)$-alkoxy, COOH and CHO group; and in particular by one or more groups chosen among an halogen atom, an OH, COOH and CHO group, and X, R, R1, R2, R3, R4, $R_0$, $R^{11}$, $R^{12}$ and $R^{13}$ are as defined above.

Thus, compound of formula (IIa-bis) corresponds to a compound of formula (IIbis) wherein $R_0$=H.

Preferably, R1, R2 and R3 represent, independently from one another, a fluorine atom or an OH, $OSiR^aR^bR^c$, $OR^{11}$, $OCOR^{11}$, $OCO_2R^{11}$ or $OCONR^{12}R^{13}$ group R1, R2 and R3 may advantageously be chosen, independently from one another, among an OH, $OR^{11}$ and $OCOR^{11}$ group with $R^{11}$ as defined above.

Even more advantageously, R1, R2 and R3 may be chosen, independently from one another, among an OH, —O—$(C_1-C_6)$-alkyl, —O-aryl, —O—$(C_1-C_6)$-alkyl-aryl and —OCO—$(C_1-C_6)$-alkyl group.

In particular, R1, R2 and R3 may be chosen, independently from one another, among an OH, $OSiMe_3$ and benzyloxy (OBn) group, and preferably among OH and OBn.

According to a particular embodiment, R1, R2 and R3 are identical.

According to another particular embodiment, R1, R2 and R3 are identical and represent each an OH group and R represents a CH$_2$OH group.

R advantageously represents a hydrogen atom or a CH$_3$, CH$_2$OH, CH$_2$OR$^{11}$, CH$_2$OSiR$^a$R$^b$R$^c$, CH$_2$OCOR$^{11}$, CH$_2$OP(O)(OH)$_2$ or CH$_2$OSO$_3$H group, and in particular a hydrogen atom or a CH$_3$, CH$_2$OH, CH$_2$OR$^{11}$, CH$_2$OCOR$^{11}$, CH$_2$OP(O)(OH)$_2$ or CH$_2$OSO$_3$H group,
with R$^a$, R$^b$, R$^c$ and R$^{11}$ as defined above, and with CH$_2$OR$^{11}$ advantageously representing a —CH$_2$O—(C$_1$-C$_6$)-alkyl, —CH$_2$O-aryl and —CH$_2$O—(C$_1$-C$_6$)-alkyl-aryl, and CH$_2$OCOR$^{11}$ group advantageously representing a —CH$_2$OCO—(C$_1$-C$_6$)-alkyl group.

Even more advantageously, R represents a CH$_2$OH, CH$_2$OSiR$^a$R$^b$R$^c$, CH$_2$OR$^{11}$ or CH$_2$OCOR$^{11}$ group, and more advantageously a CH$_2$OH, CH$_2$OR$^{11}$ or CH$_2$OCOR$^{11}$ group, with R$^a$, R$^b$, R$^c$ and R$^{11}$ as defined above.

Yet even more advantageously, R represents a CH$_2$OH, —CH$_2$O—(C$_1$-C$_6$)-alkyl, —CH$_2$O-aryl, —CH$_2$O—(C$_1$-C$_6$)-alkyl-aryl and —CH$_2$OCO—(C$_1$-C$_6$)-alkyl group.

In particular, R can represent a CH$_2$OH, CH$_2$OSiMe$_3$ or CH$_2$OBn group, and preferably a CH$_2$OH or CH$_2$OBn group.

In the same way, R4 may advantageously represent a hydrogen or halogen atom or an OH or OR$^{11}$ group, and in particular a hydrogen atom or an OH or OR$^{11}$ group, with R$^{11}$ as defined above.

Yet even more advantageously, R4 may represent a hydrogen or halogen atom or an OH, —O—(C$_1$-C$_6$)-alkyl, —O-aryl and —O—(C$_1$-C$_6$)-alkyl-aryl group, and in particular, a hydrogen atom or an OH, —O—(C$_1$-C$_6$)-alkyl, —O-aryl and —O—(C$_1$-C$_6$)-alkyl-aryl group.

In particular, R4 can represent a hydrogen or halogen (such as Br, Cl, F) atom or an OH group, and advantageously, a hydrogen atom or an OH group.

R5, R6, R7, R8, R9, R5a, R6a, R7a, R8a and R9a can be chosen among a hydrogen atom, a halogen atom, advantageously a chlorine atom, an aryl-(C$_1$-C$_6$)-alkyl group, advantageously benzyl, the alkyl group being possibly substituted by an OH group.

Advantageously, R5, R6, R7, R8, R9, R5a, R6a, R7a, R8a and R9a will be chosen, independently from one another, among a hydrogen atom, a halogen atom, advantageously a chlorine or fluorine atom, an aryl-(C$_1$-C$_6$)-alkyl, such as benzyl, aryl-(C$_1$-C$_6$)-alkyl-O—, such as benzyloxy, or aryl-CO—, such as benzoyl, group, the alkyl moiety of said group being possibly substituted by an OH group and the aryl moiety of said group being possibly substituted by an halogen atom, such as fluorine, an OH, (C$_1$-C$_6$)-alkyl or (C$_1$-C$_6$)-alkoxy group.

According to a particular embodiment, R4 represents an NH$_2$ group.

In particular, the compounds of the invention can be chosen among the following molecules:

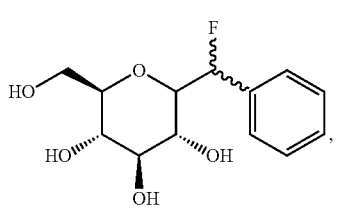

9a

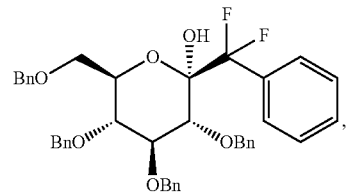

14a

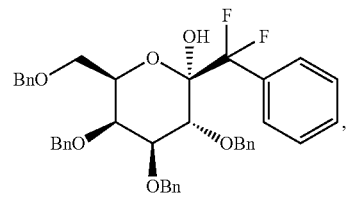

14b

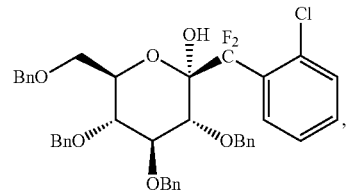

18

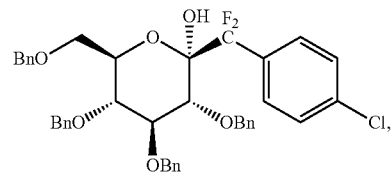

22

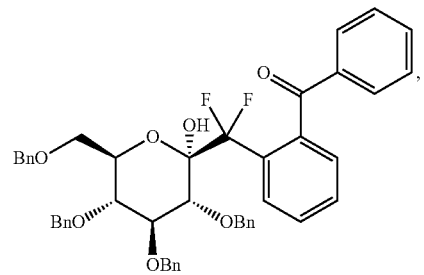

28

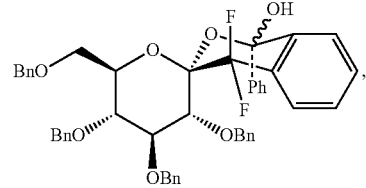

29d1/29d2

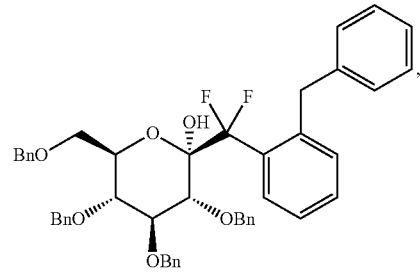

32

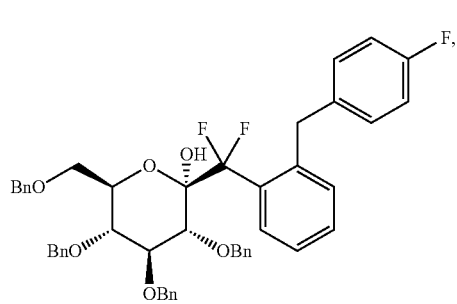
39
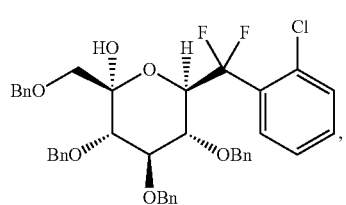
40
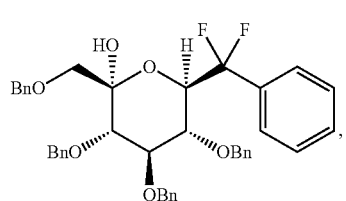
41
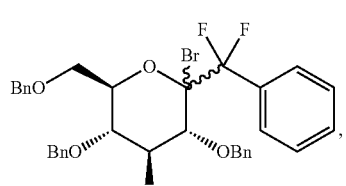
42
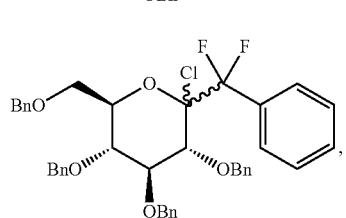
43
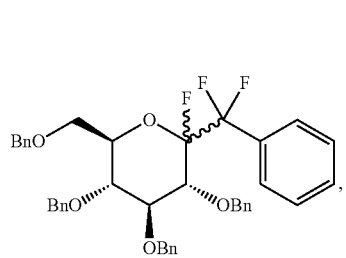
44d1/44d2
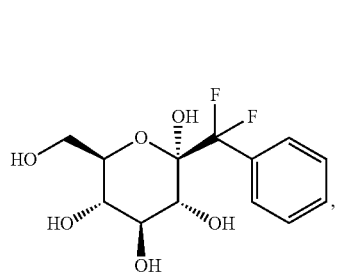
47-A
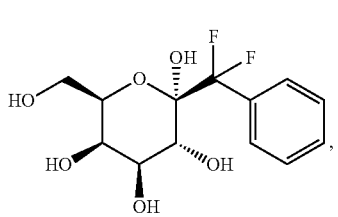
48-A
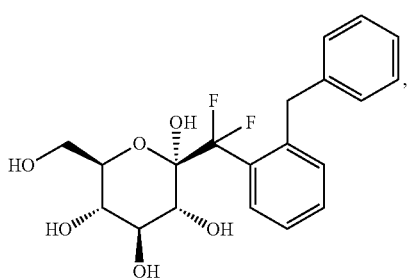
49-A
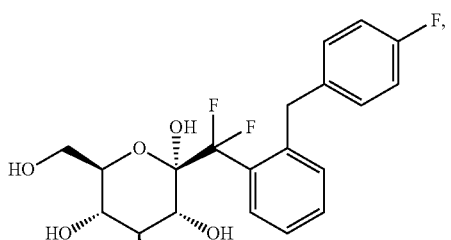
50-A
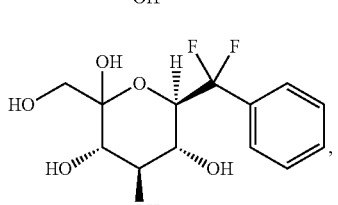
51
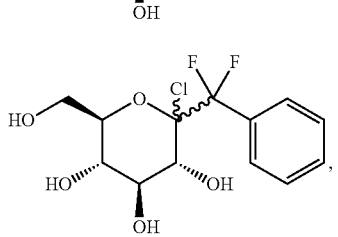
52
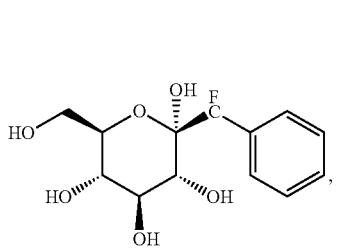
56
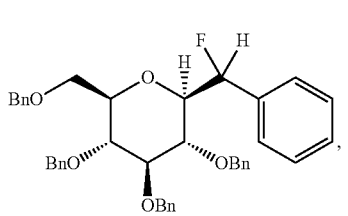
61

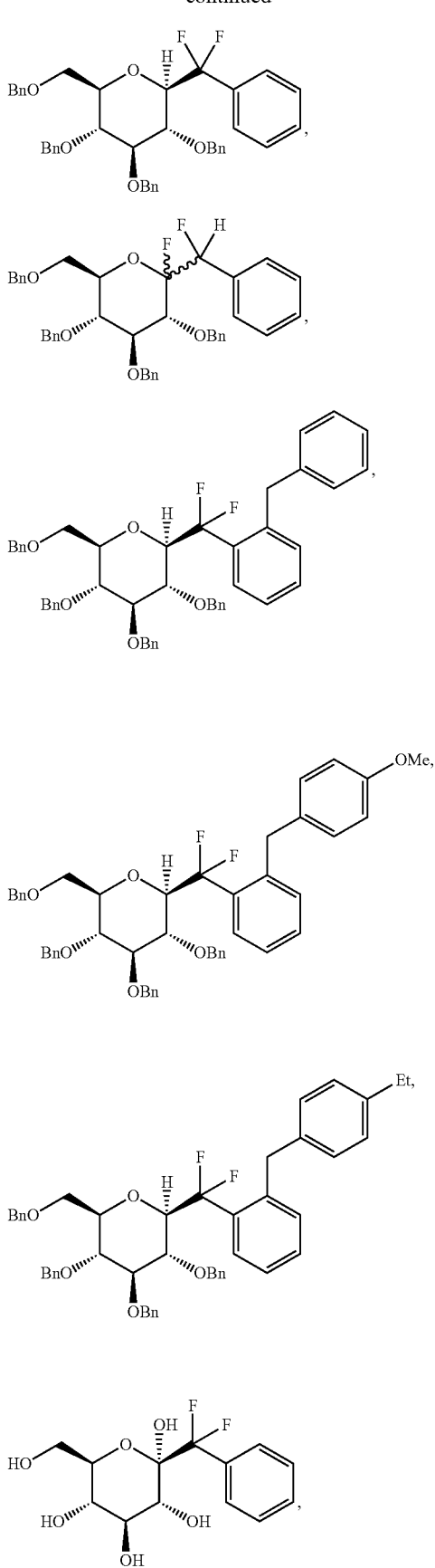
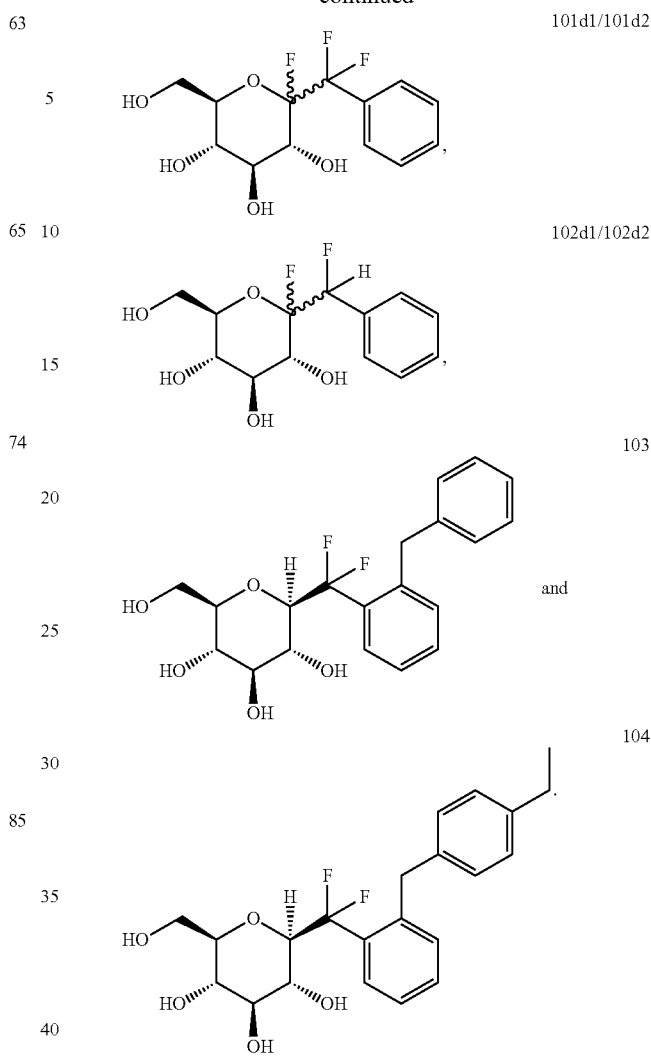

Another object of this invention is a compound as defined above, for use as a drug, in particular as an inhibitor of the sodium-dependent glucose co-transporter, such as SGLT1, SGLT2 and SGLT3.

Within the meaning of this invention, "inhibitor of the sodium-dependent glucose co-transporter" is understood to mean a compound capable of inhibiting partially or totally the sodium-dependent glucose co-transporter.

More particularly, the compounds of the invention may be used for treating diabetes, and more particularly type-II diabetes, diabetes-related complications, such as arteritis of the lower extremities, cardiac infarction, renal insufficiency, neuropathy or blindness, hyperglycemia, hyperinsulinemia, obesity, hypertriglyceridemia, X syndrome and arteriosclerosis.

The compounds of the invention may likewise be used as an anti-cancer, anti-infective, anti-viral, anti-thrombotic or anti-inflammatory drug.

The invention likewise relates to the use of a compound of the invention for the manufacture of a drug intended for the treatment of diabetes, and more particularly type-II diabetes, diabetes-related complications, such as arteritis of the lower extremities, cardiac infarction, renal insufficiency, neuropathy or blindness, hyperglycemia, hyperinsulinemia, obesity, hypertriglyceridemia, X syndrome and arteriosclerosis, as well as for the manufacture of an anti-cancer, anti-infective, anti-viral, anti-thrombotic or anti-inflammatory drug.

The invention likewise relates to a method for a treatment against diabetes, and more particularly type-II diabetes, diabetes-related complications, such as arteritis of the lower extremities, cardiac infarction, renal insufficiency, neuropathy or blindness, hyperglycemia, hyperinsulinemia, obesity, hypertriglyceridemia, X syndrome and arteriosclerosis, as well as for an anti-cancer, anti-infective, anti-viral, anti-thrombotic or anti-inflammatory treatment, including the administration of at least one compound of the invention to a patient in need thereof.

Silylated compounds of the present invention, as well as compounds with R=$CH_2$OBn, R1=OBn, R2=OBn and/or R3=OBn, will not be preferred for their use as medicament.

Another object of this invention is a pharmaceutical or cosmetic composition including at least one compound of the invention as defined above and at least one pharmaceutically or cosmetically acceptable vehicle.

In this invention, "cosmetically acceptable" is understood to mean what is useful in the preparation of a cosmetic composition which is generally safe, non-toxic and neither biologically nor otherwise undesirable and which is acceptable for veterinary as well as human cosmetic use.

The compounds according to the invention can be administered orally, sublingually, parenterally, subcutaneously, intramuscularly, intravenously, transdermally, locally or rectally.

In the pharmaceutical compounds of this invention, for oral, sublingual, parenteral, subcutaneous, intramuscular, intravenous, transdermal, local or rectal administration, the active ingredient can be administered in unit forms of administration, mixed together with conventional pharmaceutical carriers, for animals or human beings. Suitable unit forms of administration include oral forms such as tablets, gel capsules, powders, granules and oral solutions or suspensions, sublingual or buccal forms of administration, parenteral, subcutaneous, intramuscular, intravenous, intranasal or intraocular forms of administration and rectal forms of administration.

When a solid composition is prepared in the form of tablets, the principal active ingredient is mixed with a pharmaceutical vehicle such as gelatine, starch, lactose, magnesium stearate, talc, gum arabic or the like. The tablets can be coated with sucrose or other suitable materials or else treated in such a way that they have an extended or delayed activity and continuously release a predetermined amount of active principle.

A gel capsule preparation is obtained by mixing the active ingredient with a diluent and by pouring the mixture obtained into soft or hard capsules.

A preparation in the form of a syrup or elixir can contain the active ingredient in conjunction with a sweetening agent, antiseptic, as well as a flavour-producing agent and appropriate colouring agent.

Powders or granules dispersible in water can contain the active ingredient mixed together with dispersing agents, wetting agents, or suspending agents, as well as with taste correctors or sweetening agents.

For rectal administration, suppositories are used, which are prepared with binding agents melting at rectal temperature, e.g., cocoa butter or polyethylene glycols.

For parenteral, intranasal or intraocular administration, aqueous suspensions are used, isotonic saline solutions or sterile and injectable solutions, which contain pharmacologically compatible dispersing agents and/or wetting agents.

The active principle can also be formulated as microcapsules, possibly with one or more additive carriers.

The compounds of the invention can be used at doses of between 0.01 mg and 1000 mg per day, given in a single dose once a day or administered in several doses throughout the day, e.g., twice daily in equal doses. The daily dose administered is advantageously between 5 mg and 500 mg, even more advantageously between 10 mg and 200 mg. It may be necessary to use doses exceeding these ranges, of which those skilled in the art will themselves be aware.

In one particular embodiment of the invention, the pharmaceutical or cosmetic composition can also be formulated for topical administration. It may be introduced in forms commonly known for this type of administration, i.e., in particular, lotions, foams, gels, dispersions, sprays, shampoos, serums, masks, body milks or creams, for example, with excipients enabling, in particular, penetration of the skin so as to improve the properties and accessibility of the active principle. Besides the composition according to the invention, these compositions generally further contain a physiologically acceptable medium, which generally contains water or a solvent, e.g., alcohols, ethers or glycols. They can also contain surface-active agents, preservatives, stabilizers, emulsifiers, thickeners, other active principles producing a complementary or possibly synergic effect, trace elements, essential oils, perfumes, colouring agents, collagen, chemical or mineral filters, hydrating agents or thermal waters.

In one particular embodiment, the pharmaceutical composition of the invention may include at least one other active principle, in addition to the compound of the invention.

Examples of active principles that can be cited are antidiabetic agents, such as sulfonylurea-type compounds which are hypoglycemic sulfamides which increase insulin secretion like, e.g., chlorpropamide, tolbutamide, tolazamide, glipizide, gliclazide, glibenclamide, gliquidone and glimepiride, biguanides which reduce the hepatic glyconeogenesis and the insulin resistance like metformine, thiazolidinediones (also called glitazones) which increase the sensibility to insulin like rosiglitazone, pioglitazone and ciglitazone, alpha-glucosidases inhibitors which slow down the intestinal absorption of carbohydrates like acarbose, miglitol and voglibose, meglitinides (also called glitinides) which increase insulin pancreatic secretion like repaglinide and nateglinide, incretin mimics like exenatide or dipeptidylpeptidase-4 (DPP4) inhibitors like sitagliptin, vildagliptin and insulin, or antilipidic agents, such as statins which reduce cholesterol by inhibiting the enzyme HMG-CoA reductase like atorvastatin and cerivastatin, fibrates like bezafibrate, gemfibrozil and fenofibrate, or ezetimibe.

Another object of this invention is the cosmetic use of a compound of the invention as defined above, for lightening, bleaching, depigmenting the skin, removing blemishes from the skin, particularly age spots and freckles, or preventing pigmentation of the skin, via topical application in particular.

Another object of this invention is a process for preparing a compound of generic formula (Ia), as defined above, wherein X and R4 represent a hydrogen atom, characterized in that the compound of formula (Ia) is obtained by hydrogenation of the double bond of a compound of generic formula (III):

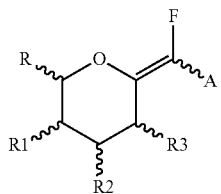

(III)

wherein A, R, R1, R2 and R3 are as defined above.

This hydrogenation occurs under a hydrogen atmosphere, in particular in the presence of palladium on carbon Pd/C.

According to a first alternative, the compound of generic formula (I) defined above can be obtained according to the following steps:

(a1) halogen-metal exchange between a compound of generic formula A-Hal, wherein A is as defined above and Hal represents an halogen atom, advantageously bromine or chlorine, and a $(C_1-C_6)$-alkyl lithium, a $(C_1-C_6)$-alkyl magnesium halide or a di-$(C_1-C_6)$-alkyl magnesium, and (b1) reaction of the compound obtained at the preceding step (a1) with a compound of generic formula (IV):

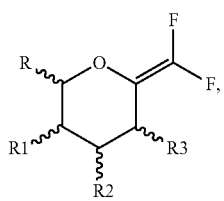

(IV)

wherein R, R1, R2 and R3 are as defined above,
in order to obtain the compound of formula (III).

Preferably, the halogen-metal exchange of step (a1) is carried out with a $(C_1-C_6)$-alkyl lithium.

Advantageously, the $(C_1-C_6)$-alkyl lithium derivative will be n-butyllithium, sec-butyllithium or tert-butyllithium.

The halogen-metal exchange can be also carried out with a $(C_1-C_6)$-alkyl magnesium halide, preferably bromide or chloride, (Grignard reagent) or with a di-$(C_1-C_6)$-alkyl magnesium in place of the $(C_1-C_6)$-alkyl lithium, possibly in the presence of lithium chloride LiCl, in order to accelerate the metalation process. The Grignard reagent is advantageously isopropylmagnesium or sec-butylmagnesium bromide or chloride, and the dialkyl magnesium is advantageously diisopropylmagnesium or di-sec-butylmagnesium.

The halogen-metal exchange reactions are preferably conducted at temperatures varying from –100° C. to 40° C., advantageously in an inert solvent or solvent mixture, e.g., such as diethylether, dioxane, tetrahydrofurane, toluene, hexane, dimethylsulfoxide, dichloromethane.

The lithium or magnesium compounds obtained via halogen-metal exchange may be possibly transmetalated with metal salts such as cerium trichloride (CeCl$_3$), zinc chloride or bromide (ZnCl$_2$, ZnBr$_2$), indium chloride or bromide (InCl$_3$, InBr$_3$) in order to form other organometallic compounds usable in the reaction of step (b1).

Alternatively, the halogen-metal exchange step (a1) could be replaced by a step for inserting a metal into the carbon-halogen bond of the halogen derivative A-Hal. Lithium and magnesium are two metals that can be used for this type of reaction. The insertion can be performed in an inert solvent or solvent mixture, e.g., such as diethylether, dioxane, tetrahydrofurane, toluene, hexane, dimethylsulfoxide, advantageously at a temperature varying from –80° C. to 100° C. In the case where no spontaneous reaction occurs, activation of the metal may be necessary, e.g., by treating with 1,2-dibromoethane, iodine, trimethysilyl chloride, acetic acid, hydrochloric acid and/or via sonication. The addition of the organometallic compound thus obtained to the compound of formula (IV) (corresponding to step (b1)) is advantageously carried out at temperatures varying between –100° C. to 60° C., advantageously in an inert solvent or solvent mixture, such as diethylether, dimethoxyethane, benzene, toluene, methylene chloride, hexane, tetrahydrofurane, dioxane, N-methylpyrrolidinone. These reactions can be conducted in air although an inert atmosphere is preferred, such as a nitrogen or argon atmosphere.

As far as the compound of generic formula (IV) is concerned, it can be obtained according to a process described in literature, in particular by a reaction on a lactone of formula (V) derived from a sugar as defined below:

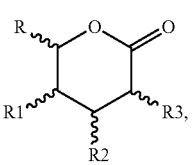

(V)

wherein R, R1, R2 and R3 are as defined above,
in the presence of dibromodifluoromethane CF$_2$Br$_2$, hexamethylphosphotriamide HMPT, and possibly zinc, in a solvent such as tetrahydrofurane (Journal of the Chemical Society, Chemical Communications (1989), 19, 1437-1439; Tetrahedron (1993), 49 (36), 8087-8106; Angewandte Chemie, International Edition (2004), 43 (48), 6680-6683) or according to a procedure as described in J. of. Fluorine Chemistry (2006), 127 (4-5), 637-642).

According to a second alternative, the compound of generic formula (III) is obtained by reacting a compound of formula A-B(OH)$_2$ or A-SnR'$_3$, wherein A is as defined above and R' represents $(C_1-C_6)$-alkyl, with a compound having the following generic formula (VI):

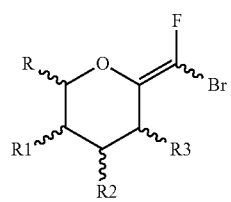

(VI)

wherein R, R1, R2, and R3 are as defined above, in the presence of a palladium catalyst and a base.

The above-described reaction thus consists of a coupling reaction (Suzuki reaction or Stille reaction) between an organoboranic acid (A-B(OH)$_2$) or a stannylated derivative (A-SnR'$_3$) and a halogenated derivative (V) in the presence of a catalyst and a base.

Among the examples of bases used, in particular but not exclusively, are sodium or potassium carbonate and sodium or potassium hydroxide.

Among the examples of catalysts, any palladium catalyst that can be used for Suzuki coupling (in the case of an A-B (OH)₂ compound), or for Stille coupling (in the case of an A-SnR'₃ compound) can be used as tetrakis(triphenylphosphin)palladium Pd(PPh₃)₄, palladium (II) acetate Pd(OAc)₂, Pd(PPh₃)₂Cl₂, Pd₂(dba)₃, PdCl₂(dppf) or PdCl₂(dpph), with "dba" meaning dibenzylideneacetone, "dppf" meaning 1,1'-bis(diphenylphosphino)ferrocen and "dpph" meanind diphenylpicrylhydrazine. Advantageously, the palladium catalyst is tetrakis(triphenylphosphin)palladium Pd(PPh₃)₄, palladium (II) acetate Pd(OAc)₂ or Pd(PPh₃)₂Cl₂.

Among the reaction solvents that can be used, in particular but not exclusively, are tetrahydrofurane (THF), N,N-dimethylformamide (DMF), dimethylsulfoxide (DMSO), toluene, alcohol such as ethanol and water, as well as mixtures of solvents.

The coupling reaction can be carried out at a temperature varying from ambient temperature to 120° C.

By "ambient temperature," it is understood to mean a temperature varying between 20° C. and 35° C., and preferably of around 25° C.

The organoboronic acid (A-B(OH)₂) could be replaced by an organoborane, such as A-9-BBN (9-BBN corresponds to 9-borabicyclo[3.3.1]nonane) or a boronic ester.

Furthermore, the compound of formula (III) could also be obtained via a coupling reaction between the halogenated derivative (VI) and an organometallic derivative obtained from the halogenated compound A-Hal, where Hal represents a halogen, via halogen-metal exchange or insertion of a metal into the carbon-halogen bond, possibly followed by transmetallation as described above.

This coupling can be catalyzed by a palladium or nickel catalyst, such as Pd₂(dba)₃, Pd(PPh₃)₄, PdCl₂(PPh₃)₂ or dmpeNiCl₂ (dmpe meaning (1,2-dimethylphosphino) ethane).

The compound of generic formula (V) can be obtained according to a process described in the patent application WO 2007/128 899, in particular via the reaction of a lactone derived from a sugar with CFBr₃, Et₂Zn and PPh₃, in a solvent such as THF.

Another object of this invention is a process for preparing a compound of generic formula (Ib) below:

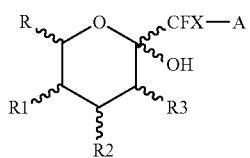
(Ib)

corresponding to a compound of formula (I), as defined above, wherein X represents a hydrogen or a fluorine atom and R4 represents an OH group, according to the following steps:

(a3) placing a compound of formula A-CFXX', wherein X is as defined above, A is as defined previously and X' represents a bromine or chlorine atom, in the presence of a compound of generic formula (V):

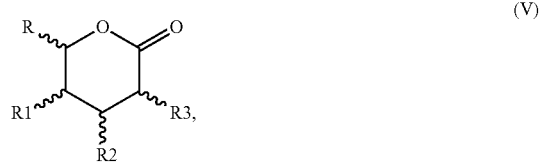
(V)

wherein R, R1, R2 and R3 are as defined previously, and (b3) addition of a (C₁-C₆)-alkyl lithium to the mixture of step (a3), in order to obtain a compound of formula (Ib).

This reaction is thus carried out under Barbier conditions, the (C₁-C₆)-alkyl lithium advantageously being n-butyllithium, sec-butyllithium or tert-butyllithium However, indium could be used also in place of the (C₁-C₆)-alkyl lithium.

According to a first alternative, the compound of formula A-CFXX' is obtained from a compound of formula A-CHO, when X represents a fluorine atom, or from a compound of formula A-CH₂OH or A-CH₂Br, when X represents a hydrogen atom, with A as defined above, via fluorination in the presence of diethylaminosulfur trifluoride (DAST) for A-CHO or A-CH₂OH or tetrabutylammonium fluoride (TBAF) for A-CH₂Br, followed by bromination or chlorination in the presence of N-bromo succinimide (NBS), N-chlorosuccinimide (NCS) or Br₂, under ultraviolet radiation.

Such a process is described, in particular, in Macromolecules (2007), 40 (19), 6799-6809 and Polymer (2007), 48, 1541-1549.

According to a second alternative, when radical A corresponds to a phenyl ring of formula (1) below:

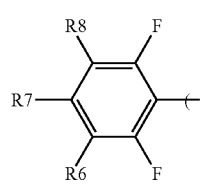
(1)

with R6, R7 and R8 as defined previously,
the compound of formula A-CFXX', wherein X=F and X'=Br, can be prepared from a compound of formula (2) below:

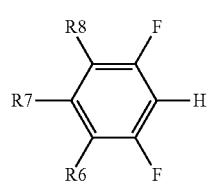
(2)

via deprotonation of compound (2) in the presence of a base such as n-butyllithium, the hydrogen atom torn away being the one situated between the two fluorine atoms, and then the anion thus obtained reacts with CF₂Br₂.

Another object of this invention is a process for preparing a compound of generic formula (Ia) as defined above, wherein:

X represents a hydrogen or a fluorine atom and
R4 represents a OSiR$^a$R$^b$R$^c$, OR$^{11}$, OCOR$^{11}$, OCO₂R$^{11}$, OCONR$^{12}$R$^{13}$ group or R3 and R4, together with the carbon atoms carrying them, form a cyclic acetal having the following formula:

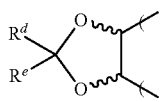

with $R^a$, $R^b$, $R^c$, $R^d$, $R^e$, $R^{11}$, $R^{12}$ and $R^{13}$ as defined above, characterised in that the compound of formula (Ia) is obtained by substitution of the OH group of a compound of formula (Ib) as defined above.

Such a substitution reaction is well known from the person skilled in the art who will know to adapt the reaction conditions.

Compounds or formula (I) wherein R4=OH, obtained in particular by a previous process, can be further involved in one or more additional reaction steps for substituting the hydroxyl group in order to produce similar compounds of formula (I) wherein the OH group of radical R4 has been replaced by an ether ($OR^{11}$), ester ($OCOR^{11}$), carbonate ($OCO_2R^{11}$), carbamate ($OCONR^{12}R^{13}$) or else a silyloxy ($OSiR^aR^bR^c$) group.

When R3 and R4 represent an OH group, a reaction with a ketone can give access to a compound of formula (I) wherein R3 and R4, together with the carbon atoms carrying them, form a cyclic acetal as defined previously.

In the same way, it is possible to convert the preceding OH group in chlorine or bromine in the presence of $SOCl_2$ or $SOBr_2$ and pyridine, to give access thus to compounds of formula (I) in which R4 represents a chlorine or bromine atom, or it is possible to convert this OH group in fluorine in the presence of a fluorinating agent such as DAST.

Starting with a compound of formula (I), wherein R4 represents a halogen atom or a leaving group (e.g., in the form of a mesylate, tosylate or triflate), it is also possible to carry out a substitution reaction with, for example, a hydrogen, an amine ($HNR^{12}R^{13}$) or with an alkyl or alkenyl group in order to give access to compounds of formula (I) wherein R4 represents a hydrogen atom or a $NR^{12}R^{13}$, ($C_1$-$C_6$)-alkyl or ($C_2$-$C_6$)-alkenyl group.

Compounds or formula (I) wherein R4=OH and $R_0$=H, obtained in particular by a previous process, can be also further involved in one or more additional reaction steps such as a concomitant magnesium derivative mediated C-1 reduction and C-5 oxydation using magnesium derivatives such as an alkoxide magnesium halide, a benzylmagnesium halide or an alkylmagnesium halide to lead to compounds of formula (I) wherein $R_0$=OH and R4=H.

By "alkoxide magnesium halide", is meant, in the sense of the present invention, a compound of formula AlkO—Mg-Hal, with Hal representing an halogen atom, such as a bromine atom, and Alk representing a ($C_1$-$C_6$)alkyl group as defined above. It can be in particular tBuOMgBr.

By "benzylmagnesium halide", is meant, in the sense of the present invention, a compound of formula Bn—Mg-Hal, with Hal representing an halogen atom, such as a bromine atom. It is in particular a benzylmagnesium bromide.

By "alkylmagnesium halide", is meant, in the sense of the present invention, a compound of formula Alk-Mg-Hal, with Hal representing an halogen atom, such as a bromine atom, and Alk representing a ($C_1$-$C_6$)alkyl group as defined above.

Furthermore, additional protection/deprotection and/or functionalization steps, well known from the person skilled in the art, can be anticipated in the preceding processes for preparing compounds of formula (I).

Another object of this invention is a process for preparing a compound of generic formula (IIa), characterized in that the compound of formula (IIa) is obtained by fluorination of a compound of the following formula (VII):

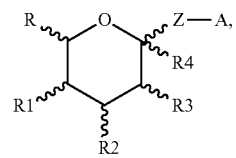

(VII)

wherein A, R, R1, R2, R3 and R4 are as defined above and Z represents a C=O, CHOH or $C(SR^{15})(SR^{16})$ group, with $R^{15}$ and $R^{16}$ representing, independently of each other, a ($C_1$-$C_6$) alkyl group or forming together an hydrocarbon chain of formula —$CH_2$—$(CH_2)_p$—, with p=1 or 2, between the two sulphur atoms.

In the case of a radical Z=C=O or CHOH, the fluorination can be carried out in the presence of a fluorinating compound such as DAST, preferably at a temperature comprised between ambient temperature and 45° C. A solvent such as dichloromethane can be used. The fluorination of a compound of formula (VII) wherein Z=C=O, respectively CHOH, gives access to a compound of formula (Ia) wherein X=F, respectively H.

In the case of a radical Z=$C(SR^{15})(SR^{16})$, the step of fluorination, which is accompanied of an oxidative desulfurization, can be carried out by using an oxidant such as NBS (N-bromosuccinimide), NIS(N-iodosuccinimide), NO+BF4– or DBH (1,3dibromo-5,5-dimethyhydantoin), along with a fluorinating agent such as HF-pyridine, HF-triethylamine, $TBAH_2F_3$ (tetrabutylammonium dihydrogen trifluoride) or DAST, in solvent such as dichloromethane, notably at a temperature ranging from 0° to room temperature (Adv. Synth. Catal. 2001, 343, No 5, 235-250).

Preferably, R4 represents a hydrogen or halogen (e.g. F, Br, Cl) atom or an OH group. When R4=OH, it is possible to modify this radical as previously described in the preceding processes.

When R4=OH, it is preferable to protect it in order to avoid its fluorination, e.g. through the use of a base such as sodium hydride (NaH) and the addition of an electrophile, in particular an alkylhalide (such as methyliodide) or a benzylhalide (such as benzyl bromide). All other classical protecting group known for a person skilled in the art can also be used to achieve protection of R4=OH.

Preferably, A represents a radical:

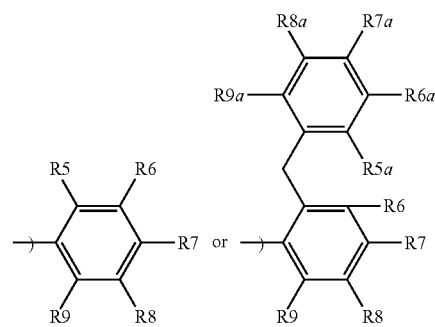

with, R5, R6, R7, R8, R9, R5a, R6a, R7a, R8a and R9a as defined above.

According to a first variant, the compound of formula (VII) can be prepared according to the following steps:

(a4) reaction between a lithio base and the dithiane compound of the following formula (VIII):

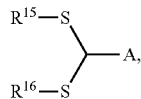

(VIII)

wherein A, R5, R6, R7, R8, R9, $R^{15}$ and $R^{16}$ are as defined above,
to give a lithio derivative of formula (IX):

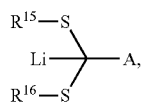

(IX)

wherein A, R5, R6, R7, R8, R9, $R^{15}$ and $R^{16}$ are as defined above, (b4) addition of the previous lithio derivative of formula (IX) obtained in the previous step (a4) onto a lactone of formula (V) as defined above to lead to a compound of formula (VIIa)

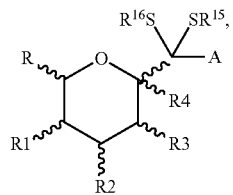

(VIIa)

wherein A, R, R1, R2, R3, R5, R6, R7, R8, R9, $R^{15}$ and $R^{16}$ are as defined above and R1=OH, which corresponds to a compound of formula (VII) wherein Z=C($SR^{15}$)($SR^{16}$) and R4=OH, (c4) hydrolysis of the dithiane moiety of the compound of formula (VIIa) obtained in the previous step (b4) to give a compound of formula (VIIb):

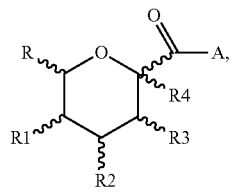

(VIIb)

wherein A, R, R1, R2, R3, R5, R6, R7, R8 and R9 are as defined above and R4=OH, which corresponds to a compound of formula (VII) wherein Z=C=O and R4=OH, (d4) optionally reduction of the compound of formula (VIIb) obtained in the previous step (c4) in order to give the compound of the following formula (VIIc):

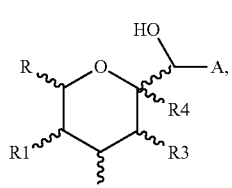

(VIIc)

wherein A, R, R1, R2, R3, R5, R6, R7, R8 and R9 are as defined above and R4=OH or H,
which corresponds to a compound of formula (VII) wherein Z=CHOH and R4=OH or H, and (e4) optionally oxidation of the compound of formula (VIIc) obtained at the previous step (d4) for which R4=H to give a compound of formula (VIIb) for which R4=H,
which corresponds to a compound of formula (VII) wherein Z=C=O and R4=H.

Step (a4) can be carried out by using an appropriate lithio base which can undergo the deprotonation followed by the lithiation of the carbon atom bearing the two sulphur atoms. It can be notably a ($C_1$-$C_6$)-alkyl lithium, such as butyllithium, or lithium diisopropylamide (LDA). If necessary, the reaction can be carried out in the presence of hexamethylphosphoric triamide or tetramethylethylenediamine. The solvent used in this reaction can be advantageously chosen among the ethers, such as tetrahydrofuran.

Dithiane compound of formula (VIII), used in this step (a1), can be obtained easily by a classical condensation of a thiol or a dithiol on the corresponding aldehyde (*J. Org. Chem.* 1978, 43(21) 4172-4177; *J. Org. Chem.* 1979, 44(15), 2804-2805; *Org. Biomol. Chem.* 2003, 1, 306-317).

By "ether", is meant, in the framework of the present invention, a compound of formula $R^{17}$—O—$R^{18}$, with $R^{17}$ and $R^{18}$ representing, independently of each other, a ($C_1$-$C_6$) alkyl group or form together an hydrocarbon chain of formula —$CH_2$—$(CH_2)_p$—, with p=1 or 2, to give a cyclic ether.

Step (b4) will be carried out advantageously in the same solvent as for step (a4), preferably at a temperature of −90° C. to 0° C.

The hydrolysis of step (c4) can be carried out in the presence of an oxidant such as NCS(N-chlorosuccinimide), NBS (N-bromosuccinimide), NIS(N-iodosuccinimide), MeI, $Br_2$ or $I_2$, with a base such as $AgNO_3$ or $CaCO_3$.

This step (c4) can be carried out in a mixture of solvent such as dichloromethane/$H_2O$, acetonitrile/$H_2O$ or $HgCl_2$ in $H_2O$.

The step (d4) of reduction can be carried out by methods well known of the person skilled in the art. For example, a Lewis acid, such as $BF_3$—OEt or TMSOTf (trimethylsilyl trifluoromethanesulfonate), and a reducing agent, such as $Et_3SiH$, can be used, notably in a solvent such as dichloromethane, optionally in mixture with acetonitrile. Preferably the reaction will be carried out at a temperature comprised between −78° C. and 0° C. In this reaction step it is possible to reduce the ketone moiety as well as the OH group of radical R4, or to reduce selectively only the ketone moiety, according to the chosen reaction conditions. In particular, the selective reduction of the ketone moiety can be carried out at lower temperatures such as about −40° C., whereas the reduction of both moieties (ketone and hydroxyle) can be carried out at higher temperatures such as about −20° C.

The step (e4) allows to give access to compounds of formula (VII) in which Z=C=O and R4=H. This oxidation reaction can be carried out in the presence of classical oxidants well known of the person skilled in the art such as by using PCC (pyridinium chlorochromate). In this case, the reaction can be carried out in a solvent such as dichloromethane, advantageously at a temperature comprised between ambient temperature and 45° C.

Moreover, when R4=OH, it is possible to modify this radical as previously described in the preceding processes to give access to other substituents. Such a reaction of modification of the radical R4 can be performed on the all the different intermediates.

According to a second variant, a compound of formula (VIIb) or (VIIc) as defined above can be prepared according to the following steps:

(a5) reaction between an aldehyde of generic formula (XI):

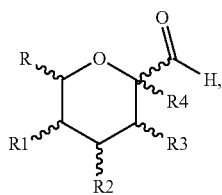
(XI)

wherein R, R1, R2, R3 and R4 are as defined above, and a compound of formula A-M, wherein A is as defined above and M represents lithium or magnesium halide, such as magnesium bromide, to give a compound of formula (VIIc) as defined above, and (b5) optionally, oxidation of the compound of formula (VIIc) obtained at the previous step (a5) to give a compound of formula (VIIb) as defined above.

In this second variant, R4 represents preferably a hydrogen atom.

Step (a5) can be carried out by the addition of the compound of formula A-M onto the aldehyde of formula (XI) according to the conditions described in the publication *Org. Biomol. Chem.* 2007, 5, 2311-2314, in particular in a solvent such as THF and preferably at about −78° C.

Compounds of formula A-M can be obtained from an halogen-metal exchange between the corresponding halide derivative (A-Hal with Hal representing an halogen atom) and a ($C_1$-$C_6$)-alkyl lithium, a ($C_1$-$C_6$)-alkyl magnesium halide or a di-($C_1$-$C_6$)-alkyl magnesium as previously described, or from a reaction between the same halide derivative with magnesium or lithium.

Compounds of formula (XI) can be prepared according to the methods described in the following publications: *Chem. Bio. Chem.* 2006, 7, 1017-1022; *Tetrahedron Lett.* 2004, 45, 7761-7763; *Tetrahedron Lett.* 2002, 43, 7271-7272; *Synlett* 2001, 1, 79-81; and *Synlett* 1994, 9, 705-708.

The oxidation of step (b5) can be carried out by methods well known of the person skilled in the art, such as by using PCC (pyridinium chlorochromate) as oxidant. In this case, the reaction can be carried out in a solvent such as dichloromethane, advantageously at a temperature comprised between ambient temperature and 45° C.

Another object of this invention is a compound of generic formula (III) as below:

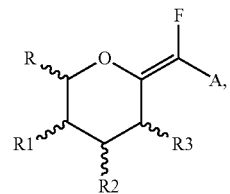
(III)

or a pharmaceutically acceptable salt thereof, a tautomer, an isomer or a mixture of isomers in any proportions, in particular a mixture of enantiomers, and particularly a racemate mixture, wherein:

R represents a hydrogen or a fluorine atom or $CH_3$, $CH_2F$, $CH_2OH$, $CH_2OSiR^aR^bR^c$, $CH_2OR^{11}$, $CH_2OCOR^{11}$, $CH_2OCO_2R^{11}$, $CH_2OCONR^{12}R^{13}$, $CH_2OP(O)(OR^{14})_2$ or $CH_2OSO_3R^{14}$ group;

R1 and R2 and represent, independently from one another, a fluorine atom or an OH, $OSiR^aR^bR^c$, $OR^{11}$, $OCOR^{11}$, $OCO_2R^{11}$ or $OCONR^{12}R^{13}$ group;

R3 represents a hydrogen or fluorine atom or an OH, $OSiR^aR^bR^c$, $OR^{11}$, $OCOR^{11}$, $OCO_2R^{11}$, $OCONR^{12}R^{13}$, $NR^{12}R^{13}$ or $NR^{12}COR^{11}$ group;

or R and R1, together with the carbon atoms carrying them, form a cyclic acetal having the following formula:

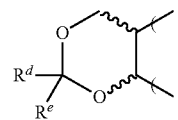

and/or (R2 and R3) or (R1 and R2), together with the carbon atoms carrying them, form a cyclic acetal having the following formula:

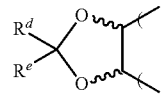

and

A represents an aryl or heteroaryl group, possibly substituted by one or more groups chosen among an halogen atom, a CN, $SO_2$, $SiR^aR^bR^c$, ($C_1$-$C_6$)-alkyl, ($C_2$-$C_6$)-alkenyl, ($C_2$-$C_6$)-alkynyl, ($C_3$-$C_7$)-cycloalkyl, 5 to 7 ring-membered heterocycloalkyl, aryl, heteroaryl, aryl-($C_1$-$C_6$)-alkyl, heteroaryl-($C_1$-$C_6$)-alkyl, ($C_1$-$C_6$)-alkyl-aryl, ($C_1$-$C_6$)-alkyl-heteroaryl, $OR^{11}$, $COR^{11}$, $OCOR^{11}$, $CO_2R^{11}$, $NR^{12}R^{13}$, $NR^{12}COR^{11}$, $CONR^{12}R^{13}$, $SR^{11}$, $SO_2R^{11}$, $CSR^{11}$ and $OSO_3R^{11}$ group, the whole being possibly substituted by one or more groups chosen among an halogen atom, an OH, ($C_1$-$C_6$)-alkyl, ($C_1$-$C_6$)-alkoxy, COOH and CHO group;

with:

$R^{11}$ representing a ($C_1$-$C_6$)-alkyl, ($C_2$-$C_6$)-alkenyl, ($C_2$-$C_6$)-alkynyl, ($C_3$-$C_7$)-cycloalkyl, 5 to 7 ring-membered heterocycloalkyl, aryl, aryl-($C_1$-$C_6$)-alkyl or ($C_1$-$C_6$)-alkyl-aryl, this group being possibly substituted by one or more groups chosen among an halogen atom, an OH, COOH and CHO group;

$R^{12}$ and $R^{13}$ representing, independently from one another, a hydrogen atom or a $(C_1-C_6)$-alkyl or aryl-$(C_1-C_6)$-alkyle group;

$R^{14}$ representing a hydrogen atom or a $(C_1-C_6)$-alkyl group;

$R^a$, $R^b$ and $R^c$ representing, independently from one another, a $(C_1-C_6)$-alkyl, aryl or aryl-$(C_1-C_6)$-alkyl group; and $R^d$ and $R^e$ representing, independently from one another, a hydrogen atom or a $(C_1-C_6)$-alkyl group.

The compounds of formula (III) are useful, in particular, as synthesis intermediates of the compounds of formula (I).

The preceding compounds respond advantageously to the formula (IIIbis) or (IIIter) below:

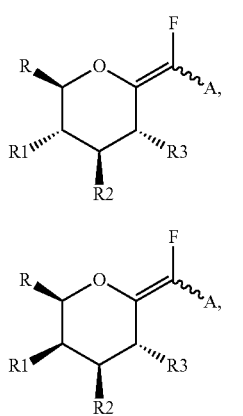

(IIIbis)

(IIIter)

with R, R1, R2, R3 and A as defined previously.

The preceding compounds respond advantageously to the formula (IIIbis).

According to a particular embodiment of the invention, A represents an aryl or heteroaryl group, possibly substituted by one or more groups chosen among an halogen atom, a CN, $SO_2$, $SiR^aR^bR^c$, $(C_1-C_6)$-alkyl, $(C_2-C_6)$-alkenyl, $(C_2-C_6)$-alkynyl, $(C_3-C_7)$-cycloalkyl, 5 to 7 ring-membered heterocycloalkyl, aryl, heteroaryl, aryl-$(C_1-C_6)$-alkyl, heteroaryl-$(C_1-C_6)$-alkyl, $(C_1-C_6)$-alkyl-aryl, $(C_1-C_6)$-alkyl-heteroaryl, $OR^{11}$, $COR^{11}OCOR^{11}$, $CO_2R^{11}$, $NR^{12}R^{13}$, $CONR^{12}R^{13}$, $SR^{11}$, $SO_2R^{11}$, $CSR^{11}$ and $OSO_3R^{11}$ group, the whole being possibly substituted by one or more groups chosen among an halogen atom, an OH, COOH and CHO group, $R^a$, $R^b$, $R^c$, $R^{11}$, $R^{12}$ and $R^{13}$ being as defined above.

The radical A advantageously represents a phenyl group possibly substituted by one or more groups chosen among an halogen atom, a CN, $SO_2$, $SiR^aR^bR^c$, $(C_1-C_6)$-alkyl, $(C_2-C_6)$-alkenyl, $(C_2-C_6)$-alkynyl, $(C_3-C_7)$-cycloalkyl, 5 to 7 ring-membered heterocycloalkyl, aryl, heteroaryl, aryl-$(C_1-C_6)$-alkyl, hetero aryl-$(C_1-C_6)$-alkyl, $(C_1-C_6)$-alkyl-aryl, $(C_1-C_6)$-alkyl-heteroaryl, $OR^{11}$, $COR^{11}$, $OCOR^{11}$, $CO_2R^{11}$, $NR^{12}R^{13}$, $CONR^{12}R^{13}$, $SR^{11}$, $SO_2R^{11}$, $CSR^{11}$ and $OSO_3R^{11}$ group, the whole being possibly substituted by one or more groups chosen among an halogen atom, an OH, $(C_1-C_6)$-alkyl, $(C_1-C_6)$-alkoxy, COOH and CHO group, and notably among an halogen atom, an OH, COOH and CHO group, $R^a$, $R^b$, $R^c$, $R^{11}$, $R^{12}$ and $R^{13}$ being as defined above.

Consequently, according to a first particular embodiment of the invention, a compound of the invention advantageously responds to the following generic formula (IIIa):

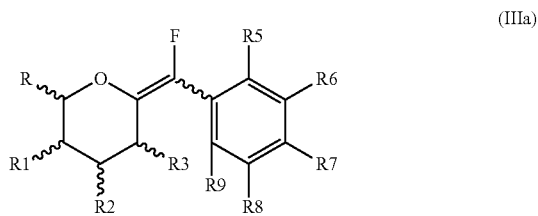

(IIIa)

wherein:

R5, R6, R7, R8 and R9 represent, independently from one another, a hydrogen atom, an halogen atom, a CN, $SO_2$, $SiR^aR^bR^c$, $(C_1-C_6)$-alkyl, $(C_2-C_6)$-alkenyl, $(C_2-C_6)$-alkynyl, $(C_3-C_7)$-cycloalkyl, 5 to 7 ring-membered heterocycloalkyl, aryl, heteroaryl, aryl-$(C_1-C_6)$-alkyl, heteroaryl-$(C_1-C_6)$-alkyl, $(C_1-C_6)$-alkyl-aryl, $(C_1-C_6)$-alkyl-heteroaryl, $OR^{11}$, $COR^{11}$, $OCOR^{11}$, $CO_2R^{11}$, $NR^{12}R^{13}$, $NR^{12}COR^{11}$, $CONR^{12}R^{13}$, $SR^{11}$, $SO_2R^{11}$, $CSR^{11}$ or $OSO_3R^{11}$ group, possibly substituted by one or more groups chosen among an halogen atom, an OH, $(C_1-C_6)$-alkyl, $(C_1-C_6)$-alkoxy, COOH and CHO group, and notably among an halogen atom, an OH, COOH and CHO group; and R, R1, R2, R3, $R^{11}$, $R^{12}$ and $R^{13}$ are as defined above.

Moreover, according to a second particular embodiment of the invention, a compound of the invention is advantageously based on the following generic formula (IIIb):

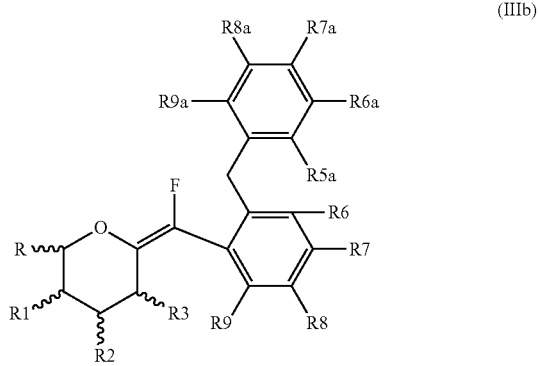

(IIIb)

wherein:

R6, R7, R8, R9, R5a, R6a, R7a, R8a and R9a represent, independently from one another, a hydrogen atom, an halogen atom, a CN, $SO_2$, $SiR^aR^bR^c$, $(C_1-C_6)$-alkyl, $(C_2-C_6)$-alkenyl, $(C_2-C_6)$-alkynyl, $(C_3-C_7)$-cycloalkyl, 5 to 7 ring-membered heterocycloalkyl, aryl, heteroaryl, aryl-$(C_1-C_6)$-alkyl, heteroaryl-$(C_1-C_6)$-alkyl, $(C_1-C_6)$-alkyl-aryl, $(C_1-C_6)$-alkyl-heteroaryl, $OR^{11}$, $COR^{11}$, $OR^{11}$, $CO_2R^{11}$, $NR^{12}R^{13}$, $NR^{12}COR^{11}$, $CONR^{12}R^{13}$, $SR^{11}$, $SO_2R^{11}$, $CSR^{11}$ or $OSO_3R^{11}$ group, the said group being possibly substituted by one or more groups chosen among an halogen atom, an OH, $(C_1-C_6)$-alkyl, $(C_1-C_6)$-alkoxy, COOH and CHO group; and in particular by one or more groups chosen among an halogen atom, an OH, COOH and CHO group, and X, R, R1, R2, R3, $R_0$, $R^{11}$, $R^{12}$ and $R^{13}$ are as defined above.

Preferably, R1, R2 and R3 represent, independently from one another, a fluorine atom or an OH, $OSiR^aR^bR^c$, $OR^{11}$, $OCOR^{11}$, $OCO_2R^{11}$ or $OCONR^{12}R^{13}$ group.

R1, R2 and R3 may advantageously be chosen, independently from one another, among an OH, $OR^{11}$ and $OCOR^{11}$ group with $R^{11}$ as defined above.

Even more advantageously, R1, R2 and R3 may be chosen, independently from one another, among an OH, —O—($C_1$-$C_6$)-alkyl, —O-aryl, —O—($C_1$-$C_6$)-alkyl-aryl and —OCO—($C_1$-$C_6$)-alkyl group.

In particular, R1, R2 and R3 may be chosen, independently from one another, among an OH, $OSiMe_3$ and benzyloxy (OBn) group, and preferably among OH and OBn.

According to a particular embodiment, R1, R2 and R3 are identical.

Advantageously, R represents a hydrogen atom or a $CH_3$, $CH_2OH$, $CH_2OSiR^aR^bR^c$, $CH_2OR^{11}$, $CH_2OCOR^{11}$, $CH_2OP(O)(OH)_2$ or $CH_2OSO_3H$ group, and more advantageously a hydrogen atom or a $CH_3$, $CH_2OH$, $CH_2OR^{11}$, $CH_2OCOR^{11}$, $CH_2OP(O)(OH)_2$ or $CH_2OSO_3H$ group, with $R^a$, $R^b$, $R^c$ and $R^{11}$ as defined above, and with $CH_2OR^{11}$ advantageously representing a —$CH_2$O—($C_1$-$C_6$)-alkyl, —$CH_2$O-aryl and —$CH_2$O—($C_1$-$C_6$)-alkyl-aryl group, and $CH_2OCOR^{11}$ advantageously representing a —$CH_2$OCO—($C_1$-$C_6$)-alkyl group.

Even more advantageously, R represents a $CH_2OH$, $CH_2OSiR^aR^bR^c$, $CH_2OR^{11}$ or $CH_2OCOR^{11}$ group, and more advantageously a $CH_2OH$, $CH_2OR^{11}$ or $CH_2OCOR^{11}$ group, with $R^a$, $R^b$, $R^c$ and $R^{11}$ as defined above.

Even more advantageously, R represents a $CH_2OH$, —$CH_2$O—($C_1$-$C_6$)-alkyl, —$CH_2$O-aryl, —$CH_2$O—($C_1$-$C_6$)-alkyl-aryl and —$CH_2$OCO—($C_1$-$C_6$)-alkyl group.

In particular, R can represent a $CH_2OH$, $CH_2OSiMe_3$ or $CH_2OBn$ group and preferably a $CH_2OH$ or $CH_2OBn$ group.

R5, R6, R7, R8, R9, R5a, R6a, R7a, R8a and R9a can be chosen among a hydrogen atom, an halogen atom, advantageously a chlorine atom, an aryl-($C_1$-$C_6$)-alkyl group, advantageously benzyl, the alkyl group being possibly substituted by an OH group.

Advantageously, R5, R6, R7, R8, R9, R5a, R6a, R7a, R8a and R9a will be chosen, independently from one another, among a hydrogen atom, a halogen atom, advantageously a chlorine or fluorine atom, a CHO group, a 5 to 7 ring-membered heterocycloalkyl group, an aryl-($C_1$-$C_6$)-alkyl, such as benzyl, or aryl-CO—, such as benzoyl, group, the alkyl moiety of said group being possibly substituted by an OH group and the aryl moiety of said group being possibly substituted by an halogen atom, such as fluorine, a ($C_1$-$C_6$)-alkyl or ($C_1$-$C_6$)-alkoxy group.

In particular, the compounds of the invention can be chosen among the following molecules:

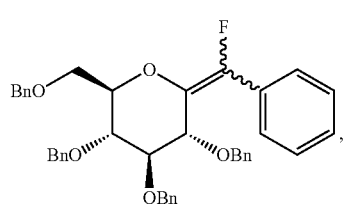

4ad1/4ad2

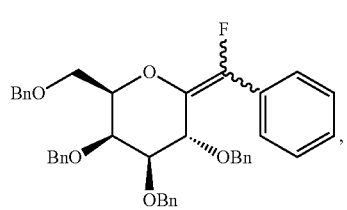

4bd1/4bd2

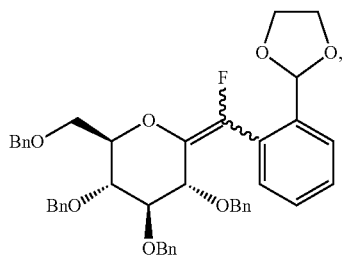

6ad1/6ad2

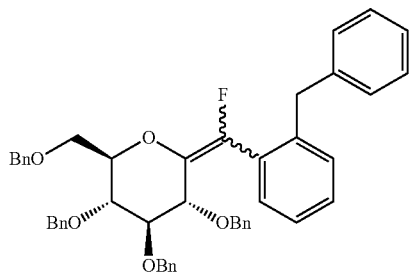

8ad2 and

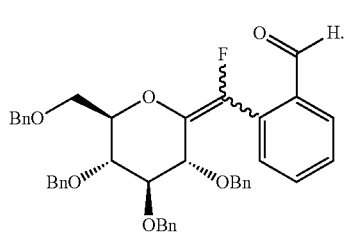

10ad2

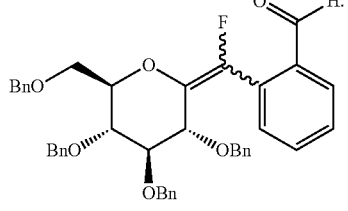

Another object of the present invention is a compound of formula (VII):

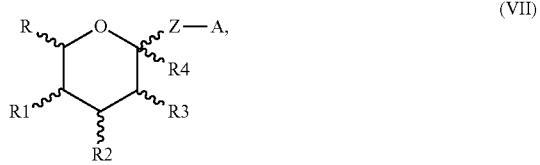

(VII)

or a pharmaceutically acceptable salt thereof, a tautomer, an isomer or a mixture of isomers in any proportions, in particular a mixture of enantiomers, and particularly a racemate mixture wherein A, Z, R, R1, R2, R3 and R4 are as defined above.

The compounds of formula (VII) are useful, in particular, as synthesis intermediates of the compounds of formula (I).

The preceding compounds respond advantageously to the formula (VIIbis) or (VIIter) below:

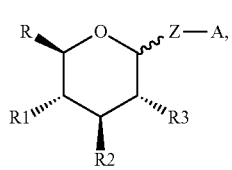

(VIIbis)

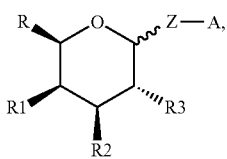
(VIIter)

with R, R1, R2, R3, R4, Z and A as defined previously.
The preceding compounds respond advantageously to the formula (VIIbis).

According to a first particular embodiment of the invention, the compound is advantageously based on the following generic formula (VIIa):

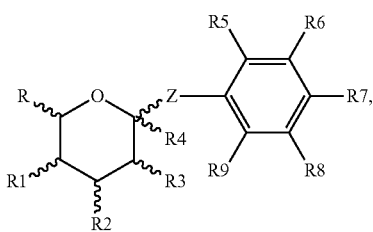
(VIIa)

with R, R1, R2, R3, R4, R5, R6, R7, R8, R9 and Z as defined above.

According to a second particular embodiment of the invention, the compound is advantageously based on the following generic formula (VIIb):

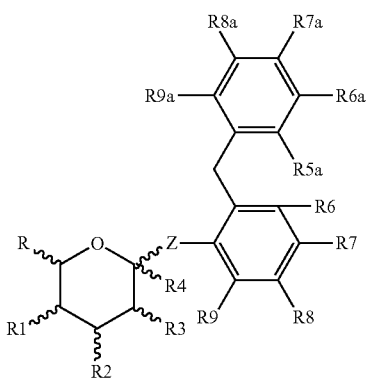
(VIIb)

with R, R1, R2, R3, R4, R6, R7, R8, R9, R5a, R6a, R7a, R8a, R9a and Z as defined above.

Preferably, R1, R2 and R3 represent, independently from one another, a fluorine atom or an OH, $OSiR^aR^bR^c$, $OR^{11}$, $OCOR^{11}$, $OCO_2R^{11}$ or $OCONR^{12}R^{13}$ group.

R1, R2 and R3 may advantageously be chosen, independently from one another, among an OH, $OSiR^aR^bR^c$, $OR^{11}$ and $OCOR^{11}$ group, and even more advantageously among an OH, $OR^{11}$ and $OCOR^{11}$ group, with $R^a$, $R^b$, $R^c$ and $R^{11}$ as defined above.

Even more advantageously, R1, R2 and R3 may be chosen, independently from one another, among an OH, —O—($C_1$-$C_6$)-alkyl, —O-aryl, —O—($C_1$-$C_6$)-alkyl-aryl and —OCO—($C_1$-$C_6$)-alkyl group.

In particular, R1, R2 and R3 may be chosen, independently from one another, among an OH, $OSiMe_3$ and benzyloxy (OBn) group, and preferably among OH and Obn.

According to a particular embodiment, R1, R2 and R3 are identical.

Advantageously, R represents a hydrogen atom or a $CH_3$, $CH_2OH$, $CH_2OSiR^aR^bR^c$, $CH_2OR^{11}$, $CH_2OCOR^{11}$, $CH_2OP(O)(OH)_2$ or $CH_2OSO_3H$ group, with $R^a$, $R^b$, $R^c$ and $R^{11}$ as defined above, and with $CH_2OR^{11}$ advantageously representing a —$CH_2O$—($C_1$-$C_6$)-alkyl, —$CH_2O$-aryl and —$CH_2O$—($C_1$-$C_6$)-alkyl-aryl group, and $CH_2OCOR^{11}$ advantageously representing a —$CH_2OCO$—($C_1$-$C_6$)-alkyl group.

Even more advantageously, R represents a $CH_2OH$, $CH_2OSiR^aR^bR^c$, $CH_2OR^{11}$ or $CH_2OCOR^{11}$ group, with $R^a$, $R^b$, $R^c$ and $R^{11}$ as defined above.

Even more advantageously, R represents a $CH_2OH$, —$CH_2O$—($C_1$-$C_6$)-alkyl, —$CH_2O$-aryl, —$CH_2O$—($C_1$-$C_6$)-alkyl-aryl and —$CH_2OCO$—($C_1$-$C_6$)-alkyl group.

In particular, R can represent a $CH_2OH$, $CH_2OSiMe_3$ or $CH_2OBn$ group, and preferably a $CH_2OH$ or $CH_2OBn$ group.

In the same way, R4 may advantageously represent a hydrogen or halogen atom or an OH or $OR^{11}$ group, and in particular a hydrogen atom or an OH or $OR^{11}$ group, with $R^{11}$ as defined above.

Yet even more advantageously, R4 may represent a hydrogen or halogen atom or an OH, —O—($C_1$-$C_6$)-alkyl, —O-aryl and —O—($C_1$-$C_6$)-alkyl-aryl group, and in particular, a hydrogen atom or an OH, —O—($C_1$-$C_6$)-alkyl, —O-aryl and —O—($C_1$-$C_6$)-alkyl-aryl group.

In particular, R4 can represent a hydrogen or halogen (such as Br, Cl, F) atom or an OH group, and advantageously, a hydrogen atom or an OH group.

Advantageously, R5, R6, R7, R8, R9, R5a, R6a, R7a, R8a and R9a will be chosen, independently from one another, among a hydrogen atom, a halogen atom, advantageously a chlorine or fluorine atom, an aryl-($C_1$-$C_6$)-alkyl, such as benzyl, aryl-($C_1$-$C_6$)-alkyl-O—, such as benzyloxy, or aryl-CO—, such as benzoyl, group, the alkyl moiety of said group being possibly substituted by an OH group and the aryl moiety of said group being possibly substituted by an halogen atom, such as fluorine, an OH, ($C_1$-$C_6$)-alkyl or ($C_1$-$C_6$)-alkoxy group.

In particular, the compounds of formula (II) can be chosen among the following molecules:

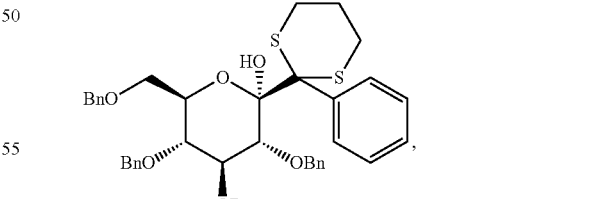
57

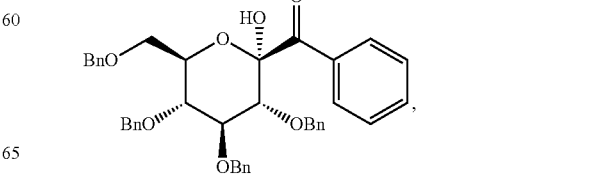
58

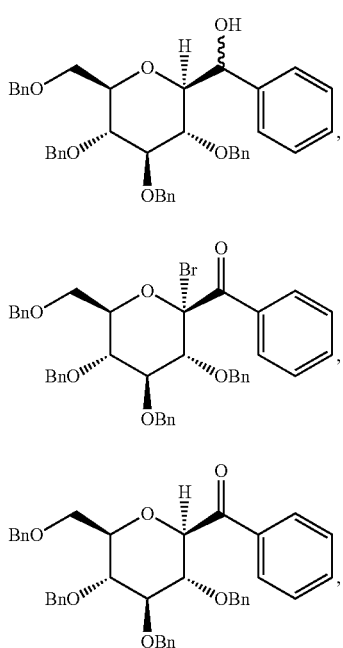
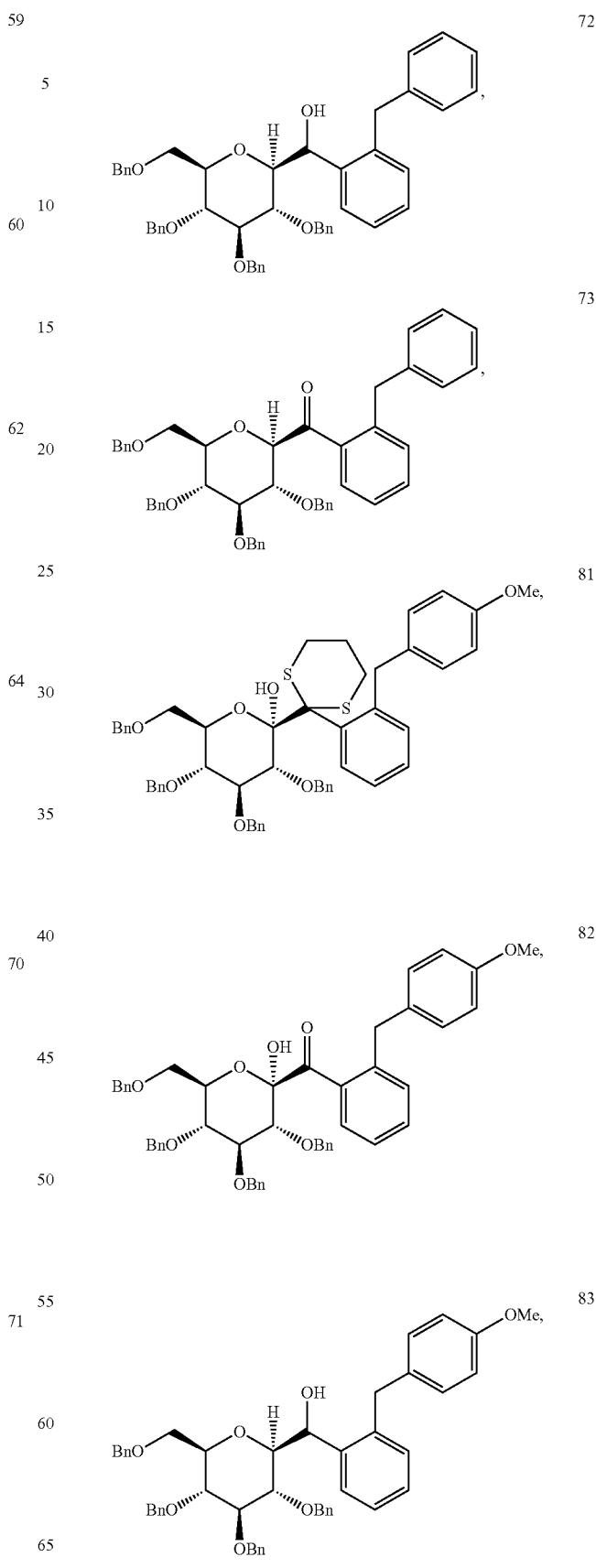

-continued

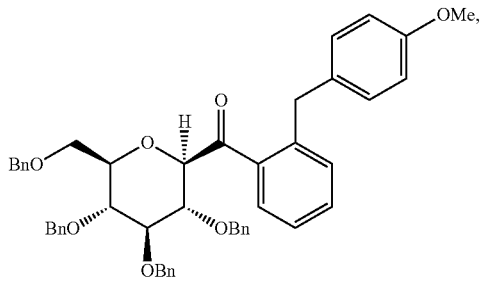
84

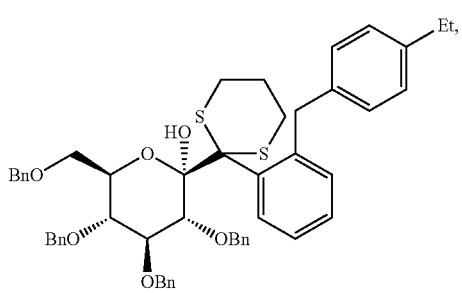
91

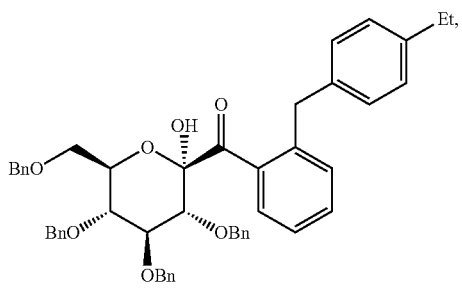
92

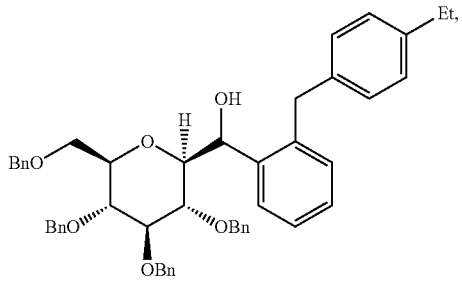
93

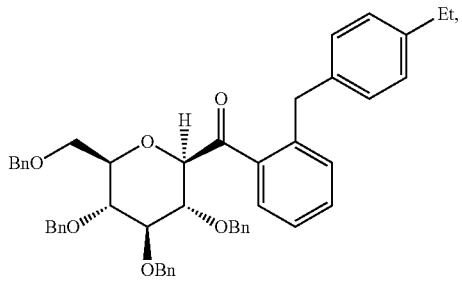
94

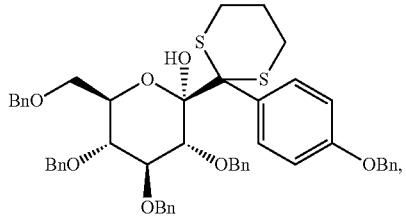
98

-continued

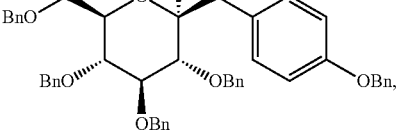
99

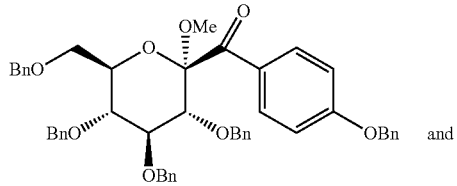
105 and

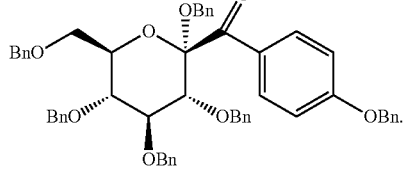
106

The invention will be better understood upon reading the following examples, these examples serving solely to illustrate the invention.

EXAMPLES

1. Preparation of the Compounds of the Invention

The abbreviations encountered are defined as follows:

| | | |
|---|---|---|
| eq.: equivalent | g: gram | Hz: Hertz |
| mg: milligramme | MHz: megahertz | min.: minute |
| mL: millilitre | mmol: millimole | µmol: micromole |
| nmol: nanomole | de: diastereomeric excess | |

The features of the devices used to conduct analyses of all of the compounds described in this application are indicated hereinbelow:

The $^{19}$F NMR spectra were recorded on BRUKER DPX 300 and DPX 600 spectrometers. The internal reference used is fluorotrichloromethane $CFCl_3$. Chemical shifts ($\delta$) are expressed in parts per million (ppm), and coupling constants (J) in Hertz (Hz).

The following abbreviations were used:
s for singlet, bs for broad singlet, d for doublet, t for triplet, qdt for quartet, m for multiplet or massive, dd for doublet of doublet, etc.

The mass spectra were obtained on a spectrophotometer of the Micromass TOF-SPEC E 20 kV, α-cyano type, for MALDI ionization and JEOL AX500, 3 kV, Canon FAB JEOL, Xe, 4 kV, 10 µA limiting current, Gly-NBA 50:50 for FAB ionization.

Separations via column chromatography are carried out under light pressure by following chromatography techniques on Kieselgel 60 silica (230-400 Mesh, Merck).

Follow-up is ensured via thin-layer chromatography (TLC) with Kieselgel 60E-254-0.25-mm plates. The ratio of the migration distance of a compound on a given support to the migration distance of an eluent is called the retardation factor (Rf).

Exemplary compound preparations according to the invention will be described hereinbelow, for non-limiting, illustrative purposes.

The compounds have been numbered by assigning the letter a to the glucose derivatives and b to the galactose derivatives.

Synthesis of Compounds 2a

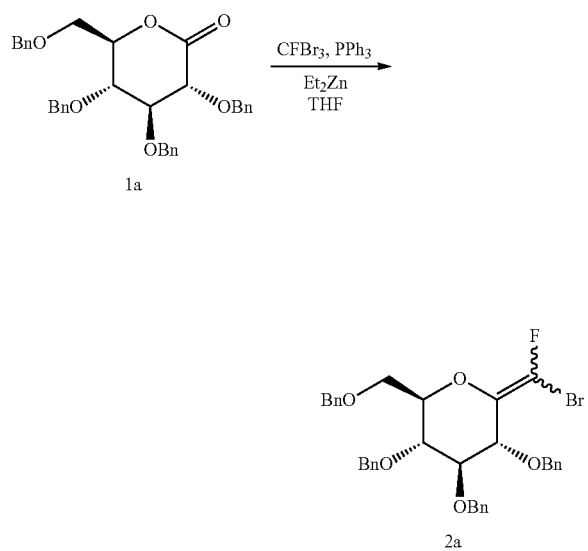

Into a round-bottom flask under an inert atmosphere containing the triphenylphosphin $PPh_3$ (849 mg; 3.2 mmol; 3.4 eq.), the tribromofluoromethane $CFBr_3$ (313 μL; 3.2 mmol; 3.4 eq.) and the lactone 1a (synthesized according to *J. Org. Chem.* 1967, 32 (8) 2531-2534) (500 mg; 0.928 mmol; 1 eq.) in the anhydrous tetrahydrofurane (THF) (15 mL), a solution of diethylzinc $Et_2Zn$ 1 M in hexane or toluene (3.2 mL; 3.2 mmol, 3.4 eq.) is added slowly dropwise over approximately three hours using a syringe driver. The mixture is stirred for 24 hours, and then MeOH is added and the reaction mixture is concentrated. The crude product is then purified on a chromatography column and the compound 2ad1/d2, in the form of a colourless oil containing the 2 diastereomers (d1 and d2), in a ratio of (33/67), is collected together with a 95/5 mixture of cyclohexane/ethyl acetate, and with a yield of 42%.

2ad1/d2: $C_{35}H_{34}BrFO_5$ M=633.54 g·mol$^{-1}$

NMR $^{19}$F (CDCl$_3$, 282.5 MHz):

2ad1: −98.5 (dd, 2 Hz, 0.34F); 2ad2: −119.2 (d, 3 Hz, 0.66F)

Mass: (ESI+): 651 (M+H$_2$O)

Synthesis of Compounds 3a and 3b

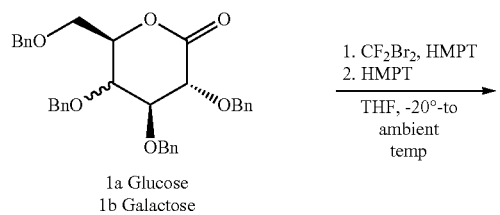

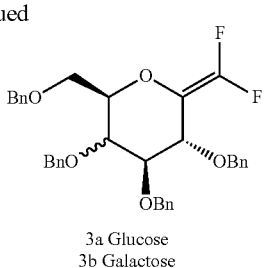

3a Glucose
3b Galactose

Into a round-bottom flask under an inert atmosphere at −20° C. containing the lactone 1a (497 mg; 0.923 mmol; 1 eq.) in tetrahydrofurane THF, the dibromodifluoromethane $CF_2Br_2$ (422 μL; 4.62 mmol; 5 eq.), and hexamethylphosphoramide (HMPT) (847 μL; 4.62 mmol; 5 eq.) are then added. The temperature of the solution is brought back up to 10° C. very slowly (in approximately 30 min) and then the hexamethylphosphoramide HMPT (2.5 mL; 13.8 mmol; 15 eq.) is added at this temperature. The solution is brought back to ambient temperature and stirred for 2 h 30 min. Diethyl ether is added and then the mixture is washed three times with a saturated aqueous copper sulphate solution. The organic phase is dried over magnesium sulphate, filtered, and then concentrated. The crude product thus obtained is chromatographed on silica gel with a (95/5) cyclohexane/ethyl acetate eluent mixture to produce the compound 3a, in the form of a yellow oil, with a yield of 58%.

Compound 3b was obtained in the form of a yellow oil with an isolated yield of 53%, by following the same procedure as above, replacing compound 1a with compound 1b (synthesized according to *J. Org. Chem.* 1967, 32 (8) 2531-2534) having the following formula:

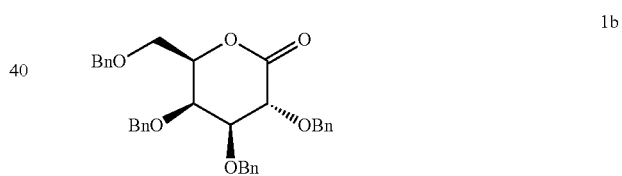

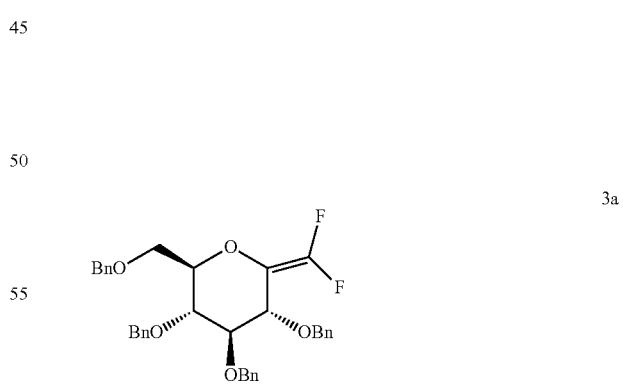

3a: $C_{35}H_{34}F_2O_5$ M=572.64 g·mol$^{-1}$

Rf=0.49 eluent: cyclohexane/ethyl acetate (9/1).

NMR $^{19}$F (CDCl$_3$, 282.5 MHz):

−99.3 (d, J$_{F-F}$=74 Hz, 1F); −116.3 (d, J$_{F-F}$=74 Hz, 1F)

Mass: (ESI+): 590.40 (M+H$_2$O); 595.53 (M+Na); 612.27 (M+K)

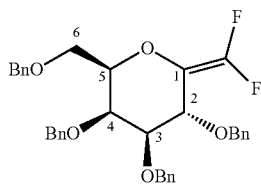

3b: $C_{35}H_{34}F_2O_5$ M=572.64 g·mol$^{-1}$

NMR $^{19}$F (CDCl$_3$, 282.5 MHz):

−97.0 (d, $J_{F-F}$=66 Hz, 1F); −110.9 (s, $J_{F-F}$=61 Hz, 1F).

Mass: (ESI+): 595 (M+Na); 611 (M+K)

Synthesis of Compounds 4ad1/d2 and 4bd1/d2

Compound 4a was synthesized in the form of two isomers, according to two different processes. Compound 4b was synthesized from the second process.

First Process:

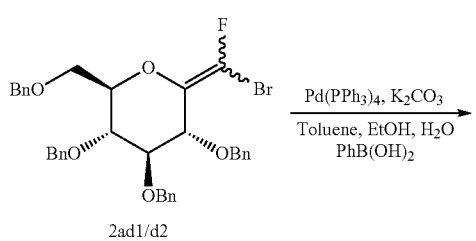

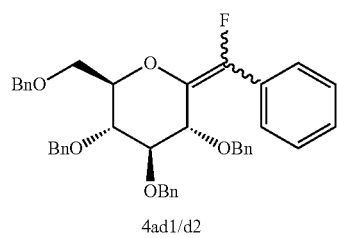

In a two-necked round-bottom flask containing the palladium tetrakis Pd(PPh$_3$)$_4$ (8 mg, 4% polarity), the potassium carbonate K$_2$CO$_3$ (75 mg, 0.54 mmol, 3 eq.) in a mixture of toluene (5.55 mL), ethanol EtOH (540 up and water H$_2$O (540 µL), compound 2ad1/d2 in the form of a mixture of the 2 isomers (in proportions of 33/67) is added and left under stirring at ambient temperature for 15 minutes. Then, the phenylboronic acid PhB(OH)$_2$ is added, and the reaction mixture is refluxed and thus kept under stirring for 3 hours. The reaction mixture is then brought back to ambient temperature, hydrolyzed and extracted three times with ether Et$_2$O. The organic phases are then collected, washed with a saturated sodium chloride solution (NaCl), then dried over magnesium sulphate MgSO$_4$, filtered and evaporated. The crude product containing the 2 isomers in a ratio of 66/34 is then purified on a silica column with a 99/1 cyclohexane/ethyl acetate mixture to produce a mixture of the major diastereomer 4ad2 and of the minor diastereomer 4ad1 with an overall yield of 90% in the form of a light yellow oil, each diastereomer being obtainable separately after purification on the silica column, if necessary.

Second Process:

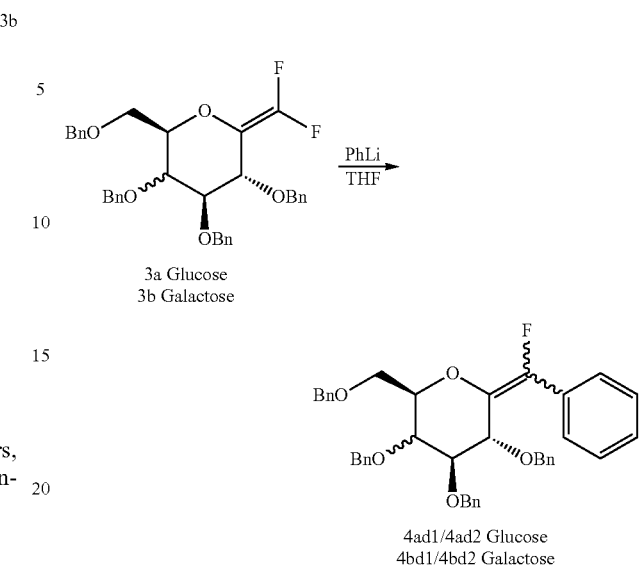

The phenyllithium 2 M (1.8 mL: 3.6 mmol; 3 eq.) is added to a round-bottom flask, under an inert atmosphere and containing compound 3a (689 mg; 1.2 mmol; 1 eq.), dissolved in anhydrous THF at 0° C. The mixture is left under stirring for 3 hours at 0° C., then gradually brought back to ambient temperature and left to stir for 12 hours. The mixture is hydrolyzed with a saturated sodium chloride solution, and dichloromethane is added. The two phases are separated, then the aqueous phase is extracted two more times with dichloromethane. The organic phases are collected, dried over magnesium sulphate, filtered and then evaporated. The crude mixture containing the two diastereomers in a ratio of 62/38 is then purified on a silica column with a 99/1 cyclohexane/ethyl acetate mixture to produce a mixture of the major diastereomer 4ad2 and of the minor diastereomer 4ad1 with an overall yield of 66%, each diastereomer being obtainable separately after purification on the silica column, if necessary.

The reaction is carried out in the same way as for compound 3b, but with 2 eq. of phenyllithium. The reaction is hydrolyzed after one hour at 0° C. and, after purification, produces 2 diastereomers in a ratio of 87/13 (major 4bd2 and minor 4bd1) with an overall yield of 46%.

4ad1 and 4ad2: $C_{41}H_{39}FO_5$ M=630.74 g·mol$^{-1}$

NMR $^{19}$F (CDCl$_3$, 282.5 MHz):

−122.2 (s) 4ad1; −154.3 (d, 2 Hz) 4ad2

Mass: (ESI+): 648 (M+H$_2$O)

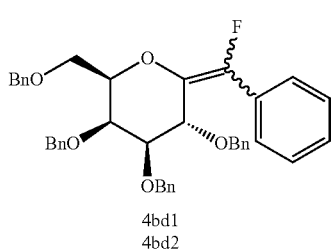

4bd1
4bd2

4bd1/4bd2: $C_{41}H_{39}FO_5$ M=630.74 g·mol$^{-1}$
NMR $^{19}$F (CDCl$_3$, 282.5 MHz):
−114 (s) 4ad1; −145.1 (d, 3 Hz) 4ad2
Mass: (ESI+): 648 (M+H$_2$O)

Synthesis of Compounds 6ad1/6ad2

Compound 6a was synthesized in the form of two isomers 6ad1 and 6ad2, according to two different processes.

First Process:

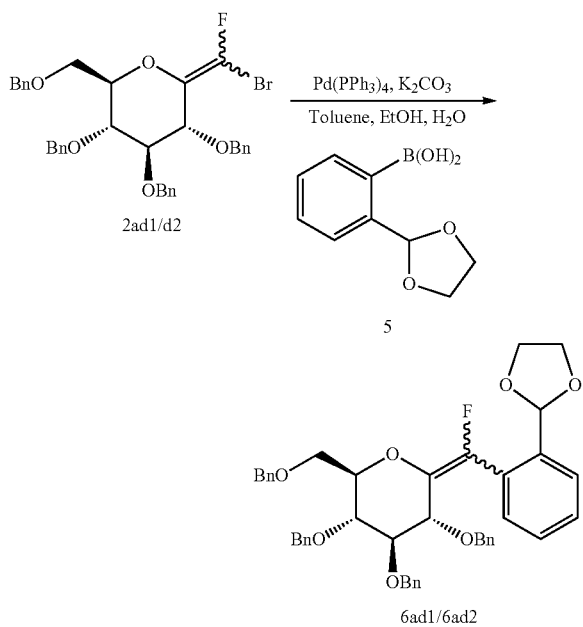

2ad1/d2

5

6ad1/6ad2

Into a round-bottom flask containing the palladium tetrakis Pd(PPh$_3$)$_4$ (8 mg, 4% polarity), the potassium carbonate K$_2$CO$_3$ (70 mg; 0.507 mmol, 3 eq.) in a mixture of toluene (5.55 mL), ethanol EtOH (540 µL) and water H$_2$O (540 mL), compound 2ad1/d2 in the form of a mixture of 2 isomers (33/67) is added and left under stirring at ambient temperature for 15 minutes. Then compound 5 is added (obtained in 2 steps according to procedures described in the Journal of Organic Chemistry (2006), 71 (20), 7840-7845 and Bull. Chem. Soc. Jpn (2002), 2267-2672), and the medium is refluxed and thus kept under stirring for 3 hours. The medium is then brought back to ambient temperature, hydrolyzed and extracted three times with ether Et$_2$O. The organic phases are then collected, washed with a saturated sodium chloride solution (NaCl), then dried over magnesium sulphate MgSO$_4$, filtered and evaporated. The crude product containing the 2 isomers is then purified on a silica column with a 97/3 cyclohexane/ethyl acetate mixture to produce a mixture of the major diastereomer 6ad2 and of the minor diastereomer 6ad1 with an overall yield of 55%, each diastereomer being obtainable separately after purification on the silica column, if necessary.

Second Process:

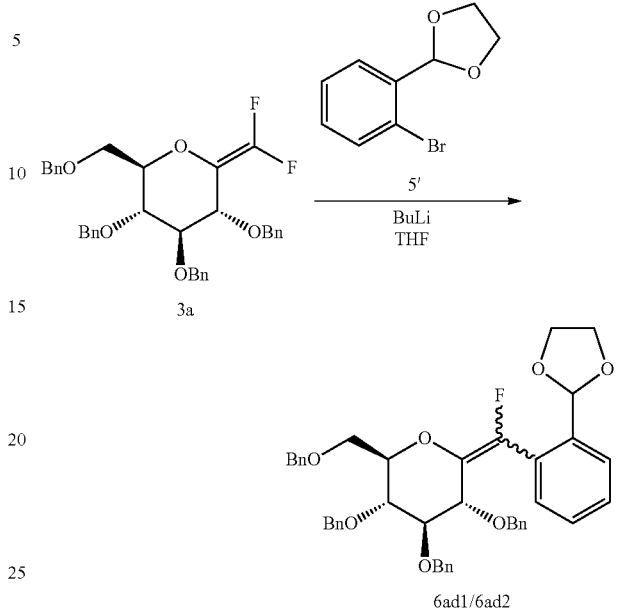

3a

6ad1/6ad2

Into a round-bottom flask, under an inert atmosphere containing compound 3a (900 mg; 1.57 mmol; 1 eq.) dissolved in anhydrous THF (20 mL) at −78° C., compound 5' (synthesized according to *J. Org. Chem.* (2006), 71(20), 7840-7845) (1.07 g; 4.71 mmol; 3 eq.) is added, then the n-butyllithium (BuLi) 1.6 M (2.84 mL, 4.55 mmol, 2.9 eq.). The mixture is left under stirring for 3 hours at −78° C., then allowed to gradually rise back to ambient temperature and left to stir for 12 hours. The mixture is hydrolyzed with a saturated sodium chloride solution, and dichloromethane is added. The two phases are separated, and then the aqueous phase is extracted two more times with dichloromethane. The organic phases are collected, dried over magnesium sulphate, filtered and then evaporated. The crude mixture containing the two diastereomers is then purified on a silica column with a 97/3 cyclohexane/ethyl acetate mixture to produce a mixture of the major diastereomer 6ad2 and of the minor diastereomer 6ad1 with an overall yield of 55%, each diastereomer being obtainable separately after purification on the silica column, if necessary.

6ad1 and 6ad2: $C_{44}H_{43}FO_7$ M=702.81 g·mol$^{-1}$
NMR $^{19}$F (CDCl$_3$, 282.5 MHz):
−136.4 (s) 6ad2; −114.7 (s) 6ad1
Mass: (ESI+): 725 (M+H$_2$O)

Synthesis of Compounds 8ad1/8ad2

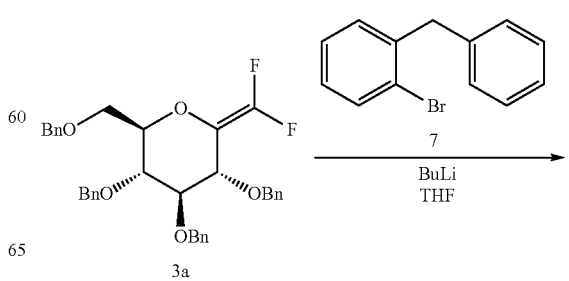

3a

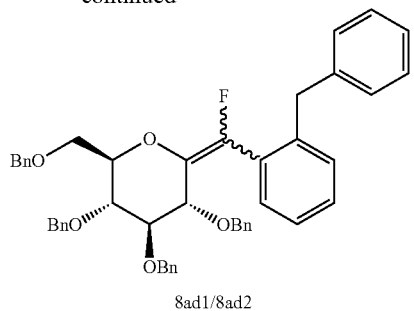

8ad1/8ad2

In to a round-bottom flask containing compound 3a (200 mg; 0.35 mmol; 1 eq.) dissolved in anhydrous THF (2 mL) at −78° C., compound 7 (172 mg; 0.698 mmol; 2 eq.) is added, followed by the n-butyllithium 1.6 M (414 μL, 0.66 mmol, 1.9 eq.). The mixture is left under stirring for 3 hours at −78° C., then allowed to gradually rise back up to ambient temperature and left to stir for 12 hours. The mixture is hydrolyzed with a saturated sodium chloride solution, and dichloromethane is added. The 2 phases are separated, and then the aqueous phase is extracted two more times with dichloromethane. The organic phases are collected, dried over magnesium sulphate, filtered and then evaporated. The crude mixture containing the two diastereomers is then purified on a silica column with a 97/3 cyclohexane/ethyl acetate mixture to produce the major diastereomer 8ad2 with an overall yield of 35%, only traces of compound 8ad1 being present, which do not allow the isolation of this compound.

8ad2: $C_{48}H_{45}FO_5$ M=720.87 g·mol$^{-1}$
NMR $^{19}$F (CDCl$_3$, 282.5 MHz):
−136.9 (s) 8ad2
Mass: (ESI+): 738 (M+H$_2$O)

Synthesis of Compound 9a

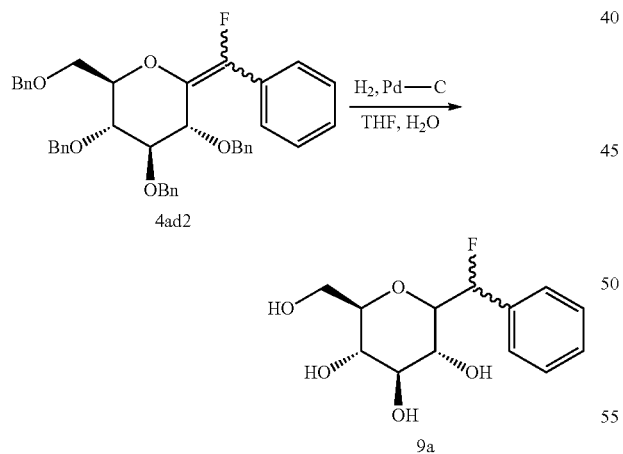

Compound 4ad2 (32.2 mg; mmol; 1 eq.) is placed inside a round-bottom flask and dissolved in a mixture of tetrahydrofurane (1 mL) and water (500 μL), in the presence of a scoopula tip of Pd/C under a hydrogen atmosphere. The mixture is stirred for 24 h, then Millipore-filtered and evaporated to produce compound 9a with a quantitative yield.

9a: $C_{13}H_{17}FO_5$ M=212.27 g·mol$^{-1}$
NMR $^{19}$F (CDCl$_3$, 282.5 MHz):
Mass: (ESI−): 211 (M−H); 246-248 (M+Cl)

Synthesis of Compound 10ad2

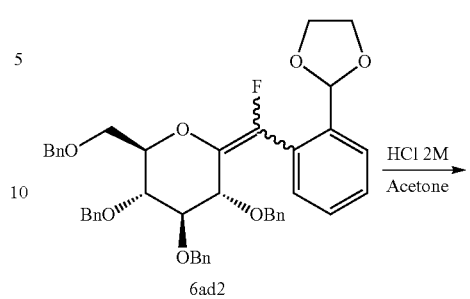

6ad2

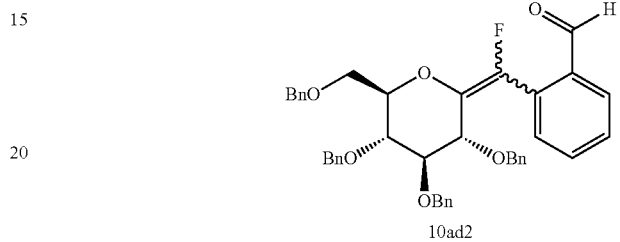

10ad2

Into a round-bottom flask containing compound 6ad2 (20 mg; 0.028 mmol; 1 eq.) in acetone (1 mL), an HCl 2M solution (200 μL; 0.4 mmol; 14 eq.) is added, and then the mixture is kept under stirring for 48 hours. A saturated sodium hydrogencarbonate solution is added, then extracted three times with dichloromethane. The organic phases are collected, dried over magnesium sulphate, filtered and then evaporated to produce compound 10ad2, in the form of a yellow oil, with a yield of 60%.

10ad2: $C_{42}H_{39}FO_6$ M=658.75 g·mol$^{-1}$
NMR $^{19}$F (CDCl$_3$, 282.5 MHz): −139.2 (s)
Mass: (ESI+): 677 (M+H$_2$O); 700 (M+H$_2$O+Na);

Synthesis of Compound 12

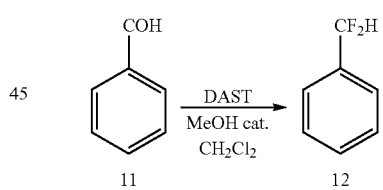

Diethylaminosulfur trifluoride (DAST) (11.8 mL; 95 mmol; 1.7 eq.) is added dropwise into a round-bottom flask under an inert atmosphere containing freshly distilled benzaldehyde 11 (5.67 mL; 56 mmol; 1 eq.) in dichloromethane (20 mL). A drop of anhydrous methanol is then added to the reaction medium in order to catalyze the reaction. The mixture is stirred for 16 h at ambient temperature and then cooled to 0° C., before adding a saturated aqueous sodium bicarbonate solution until the neutral state is reached. The mixture is then extracted with dichloromethane. The organic phase is distilled under low pressure (bp T°=35° C.; P°=61 mBar) to produce compound 12 in the form of a colourless liquid with a yield of 60%.

12: $C_7H_6F_2$ M=128.12 g·mol$^{-1}$
NMR $^{19}$F (CDCl$_3$, 282.5 Mz): −111.0 (d, J=56 Hz, 2F).
Mass: (IE): (M+•) 127-128

Synthesis of Compound 13

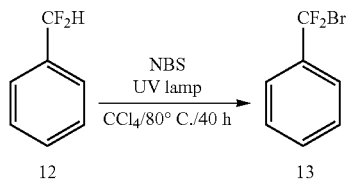

Into a round-bottom flask under an inert atmosphere containing a solution of (difluoromethyl)benzene 12 (1.74 g; 13 mmol; 1 eq.) in carbon tetrachloride (distilled over $P_2O_5$) is added N-bromosuccinimide (NBS) (5.07 g; 28 mmol; 2.1 eq.). The round-bottom flask is then provided with a cooler and the reaction medium is refluxed (80° C.) and irradiated by means of a mercury vapour UV lamp for 40 h. The mixture is then filtered, washed with water and extracted with dichloromethane. The organic phase is dried over magnesium sulphate, filtered, concentrated and then distilled under low pressure (bp T°=47° C.; P°=61 mBar) to produce compound 13 in the form of a colourless liquid, with a yield of 60%.

13: $C_7H_5BrF_2$ M=207.02 g·mol$^{-1}$
NMR $^{19}$F (CDCl$_3$, 282.5 Mz): −43.5 (s, 2F)
Mass: (IE): 206-208 (M+•).

Synthesis of Compound 14a and 14b

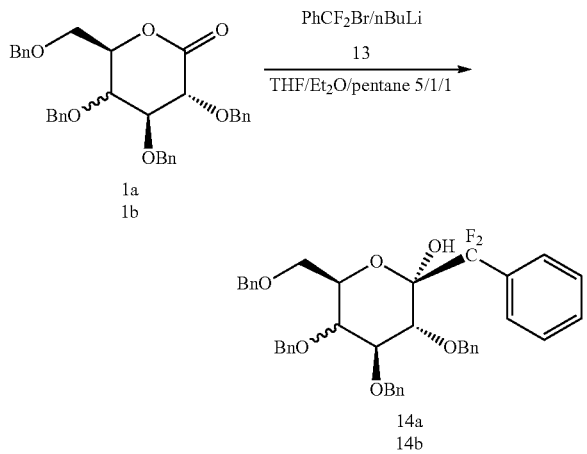

A 1.6 M solution of n-butyllithium in hexane (3.19 mL, 5.10 mmol, 5.5 eq.) is added to a round-bottom flask under an inert atmosphere, which contains a solution of 13 (0.81 mg, 3.71 mmol, 4 eq.) and the lactone 1a (0.50 g, 0.93 mmol, 1 eq.) in THF (10 mL) at −78° C. The cooling bath was removed and the reaction mixture was stirred overnight at ambient temperature. A saturated aqueous ammonium chloride solution is then added. The reaction medium is extracted with ethyl acetate and then dried over magnesium sulphate, prior to being concentrated. The residue is then purified on a chromatography column (95/5 to 90/10 cyclohexane/ethyl acetate eluent) to produce compound 14a, in the form of a white solid, with a yield of 78%.

Compound 14b (0.616 g, 71% yield, white solid) is prepared according to the procedure described above from lactone 1b (0.70 g, 1.30 mmol, 1 eq.), 1-(bromodifluoromethyl)-2-chlorobenzene 13 (1.38 g, 5.20 mmol, 4 eq.), and 1.6 M n-buthyllithium (4.06 mL, 6.50 mmol, 5 eq.).

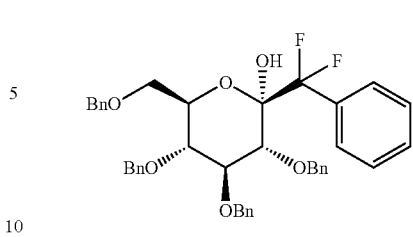

14a: $C_{41}H_{40}F_2O_6$ M=666.75 g·mol$^{-1}$
Rf: 0.41 (cyclohexane/ethyl acetate) 8/2
NMR $^{19}$F (CDCl$_3$, 282.5 Mz): −108.2 (d, J=250 Hz, 1F); −109.1 (d; J=250 Hz, 1F).
Mass: (ESI+): 684.3 (M+H$_2$O); 689.3 (M+Na$^+$); 705.3 (M+K$^+$).

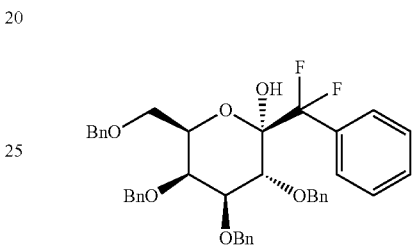

14b: $C_{41}H_{40}F_2O_6$ M=666.75 g·mol$^{-1}$
Rf: 0.41 (cyclohexane/ethyl acetate) 8/2
NMR $^{19}$F (CDCl$_3$, 282.5 MHz): −108.03 (1F, d, J=251 Hz); −109.13 (1F, d, J=252 Hz).
Mass (ESI$^+$): 718.53 (M+H$_2$O).
Anal. Calcd: C, 73.86; H, 6.05. Found: C, 73.84; H, 5.99.

Synthesis of Compound 16

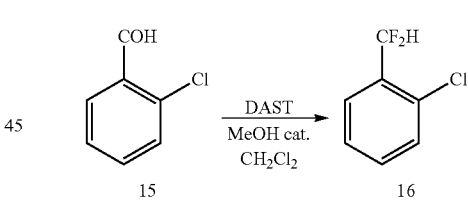

Diethylaminosulfur trifluoride (DAST) (2.97 mL; 24 mmol; 1.7 eq.) is added dropwise into a round-bottom flask under an inert atmosphere containing ortho-chlorobenzaldehyde 15 (2 g; 14 mmol; 1 eq.) in dichloromethane (15 mL). A drop of anhydrous methanol is then added to the reaction medium in order to catalyze the reaction. The mixture is stirred for 16 h at ambient temperature and is then cooled to 0° C. before adding a saturated aqueous sodium bicarbonate solution until the neutral state is reached. The mixture is then extracted with dichloromethane and dried over magnesium sulphate. The organic phase is distilled under low pressure (bp T°=40-48° C.; P°=61 mBar) to produce compound 16 in the form of a colourless liquid, with a yield of 45%.

16: $C_7H_5ClF_2$ M=162.56 g·mol$^{-1}$
NMR $^{19}$F (CDCl$_3$, 282.5 Mz): −115.2 (d, J.=54 Hz, 2F).
Mass: (IES): 161-162-163-164 (M)

Synthesis of Compound 17

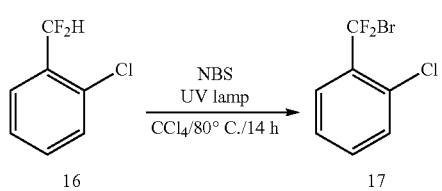

N-bromosuccinimide (0.115 g; 0.6 mmol; 2.1 eq.) is added to a quartz reactor under an inert atmosphere, which is surmounted by a mercury vapour UV lamp provided with a cooling system, and which contains a solution of ortho-chloro (difluoromethyl)benzene 16 (0.05 g; 0.3 mmol; 1 eq.) in carbon tetrachloride (distilled over $P_2O_5$). The reaction medium is refluxed and is irradiated for 14 h. The mixture is then filtered, washed with water and extracted with dichloromethane. The organic phase is dried over magnesium sulphate, filtered and then concentrated to produce compound 17 in the form of a yellow oil, with a conversion rate of 75% ($^{19}$F NMR).

17: $C_7H_4BrClF_2$ M=241.46 g·mol$^{-1}$

NMR $^{19}$F (CDCl$_3$, 282.5 Mz): −45.5 (s, 2F)

Mass: (IE): (M+•) 240-242-244.

Synthesis of Compound 18

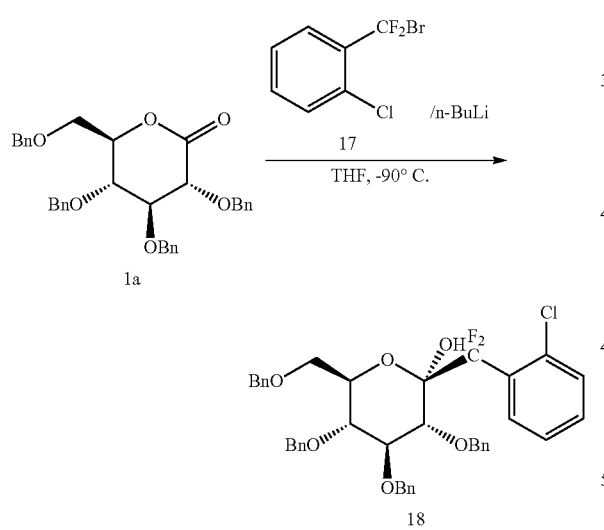

A 1.4 M solution of n-butyllithium in hexane (0.20 mL; 0.29 mmol; 1.5 eq.) is added to a round-bottom flask under an inert atmosphere, which contains the ortho-chloro (bromodifluoromethyl)benzene 17 (46 mg; 0.14 mmol; 0.7 eq.) and the lactone 1a (107 mg; 0.19 mmol; 1 eq.) at −90° C. The mixture is stirred for one hour at this temperature. A saturated aqueous ammonium chloride solution is then added at ambient temperature. The reaction medium is extracted with ethyl acetate and then dried over magnesium sulphate, prior to being concentrated. The residue is then purified on a chromatography column (95/5 cyclohexane/ethyl acetate eluent) to produce compound 18, in the form of a colourless oil, with a yield of 33%.

18: $C_{41}H_{39}F_2O_6$ M=701.19 g·mol$^{-1}$

Rf: 0.35 (cyclohexane/ethyl acetate) 8/2

NMR $^{19}$F (CDCl$_3$, 282.5 Mz): −103.5 (d, J=255 Hz, 1F), −106,7 (d, J=255 Hz, 1F)

Mass: (ESI+): 718.27 (M+H$_2$O); 723.33 (M+Na$^+$)

Synthesis of Compound 20

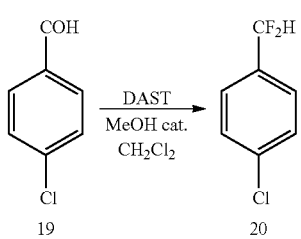

Diethylaminosulfur trifluoride (DAST) (1.48 mL; 12 mmol; 1.7 eq.) is added dropwise into a round-bottom flask under an inert atmosphere containing para-chlorobenzaldehyde 19 (1 g; 7.1 mmol; 1 eq.) in dichloromethane (15 mL). A drop of anhydrous methanol is then added to the reaction medium in order to catalyze the reaction. The mixture is stirred for 16 h at ambient temperature (88% conversion rate determined by gas chromatography (GC)), and then cooled to 0° C., before to add a saturated aqueous sodium bicarbonate solution until the neutral state is reached. The mixture is then extracted with dichloromethane, dried over magnesium sulphate, filtered and distilled under low pressure (bp T°=40-48° C.; P°=61 mBar) to produce compound 20.

20: $C_7H_5ClF_2$ M=162.56 g·mol$^{-1}$

NMR $^{19}$F (CDCl$_3$, 282.5 Mz): −110.79 (d, J=56 Hz, 2F).

Mass: (IE): 161-162-163-164 (M+•).

Synthesis of Compound 21

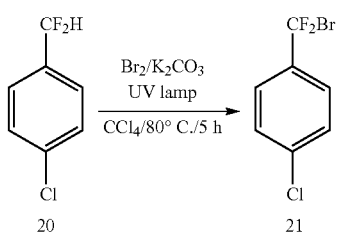

Bromine (17 μL; 0.34 mmol; 1.1 eq.) is added to a quartz reactor under an inert atmosphere, which is surmounted by a mercury vapour UV lamp equipped with a cooling system, and which contains a solution of para-chloro (difluoromethyl)benzene 20 (50 mg; 0.3 mmol; 1 eq.) in carbon tetrachloride (5 mL; distilled over $P_2O_5$) and potassium carbonate (0.212 g; 1.54 mmol; 5 eq.). The reaction medium is refluxed and is irradiated for 5 h (84% conversion rate determined by GC). The mixture is then filtered and concentrated. The product 21 is involved in the following step without purification.

21: $C_7H_4BrClF_2$ M=241.46 g·mol$^{-1}$

NMR $^{19}$F (CDCl$_3$, 282.5 Mz): −43.9 (s, 2F).

Mass: (IE): (M+•) 240-242-244.

Synthesis of Compound 22

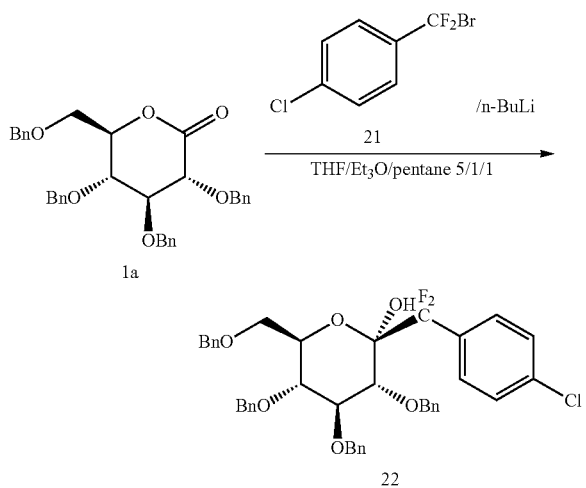

A 1.4 M solution of n-butyllithium in hexane (0.044 mL; 0.06 mmol; 1.5 eq.) is added, at −90° C., to a round-bottom flask under an inert atmosphere, which contains the para-chloro(bromodifluoromethyl)benzene 21 (15 mg; 0.06 mmol; 1.5 eq.) and the lactone 1a (22 mg; 0.04 mmol; 1 eq.) in a mixture of tetrahydrofurane, diethyl ether and pentane, in proportions of 5:1:1 (2.5 mL:0.5 mL:0.5 mL). The mixture is stirred for 1 h 30 min at this temperature. A saturated aqueous ammonium chloride solution is then added at ambient temperature. The reaction medium is then extracted with ethyl acetate and then dried over magnesium sulphate, prior to being concentrated, in order to produce compound 22.

22: $C_{41}H_{39}F_2O_6$ M=701.19 g·mol$^{-1}$
Rf: 0.45 (cyclohexane/ethyl acetate 8/2).
NMR $^{19}$F (CDCl$_3$, 282.5 Mz): −108.8 (s, 1F), −108.8 (s, 1F).
Mass: (ESI+): 719.13 (M+H$_2$O).

Synthesis of Compound 24

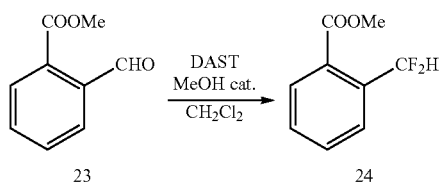

Diethylaminosulfur trifluoride (DAST) (3.8 mL; 31 mmol; 1.7 eq.) is added dropwise into a round-bottom flask under an inert atmosphere, which contains methyl 2-formylbenzoate 23 (3 g; 18 mmol; 1 eq.) in dichloromethane (20 mL). A drop of anhydrous methanol is then added to the reaction medium in order to catalyze the reaction. The mixture is stirred for 16 h at ambient temperature (82% conversion rate determined by GC) and then cooled to 0° C. prior to adding a saturated sodium bicarbonate solution until the neutral state is reached. The mixture is then extracted with dichloromethane, dried over magnesium sulphate and then concentrated. The residue is then purified on a chromatography column (95/5 cyclohexane/ethyl acetate eluent) to produce compound 24, in the form of a yellow oil, with a yield of 66%.

24: $C_9H_8F_2O_2$ M=186.16 g·mol$^{-1}$
Rf: 0.44 (cyclohexane/ethyl acetate) 9/1.
NMR $^{19}$F (CDCl$_3$, 282.5 Mz): −114.2 (d, J=56 Hz, 2F).
Mass: (ESI+): 187.07 (M+H).

Synthesis of Compound 25

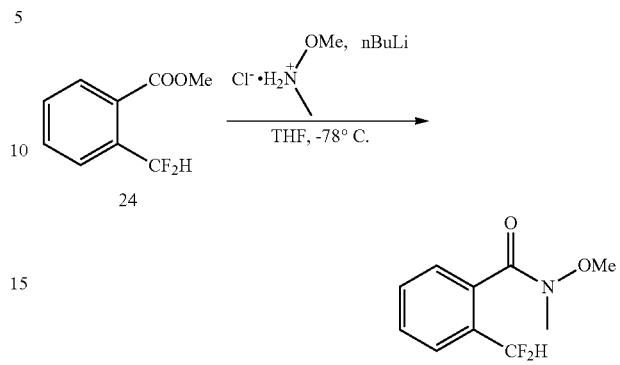

A solution of n-butyllithium 1.5 M (10.9 mL; 16 mmol; 6 eq.) is added, at −78° C., to a round-bottom flask under an inert atmosphere, which contains Weinreb amine (0.786 g; 8.0 mmol; 3 eq.) in anhydrous tetrahydrofurane (20 mL). The mixture is stirred at −78° C. for 10 min. The methyl 2-difluoromethylbenzoate 24 (0.500 g; 2.69 mmol; 1 eq.) in tetrahydrofurane (5 mL) is then added at −78° C. After stirring for 20 min, the mixture can return to ambient temperature and saturated aqueous ammonium chloride solution is added. The reaction medium is then extracted with ethyl acetate, dried over magnesium sulphate and concentrated. The residue is then purified on a chromatography column (8/2 cyclohexane/ethyl acetate eluent) in order to produce compound 25, in the form of a yellowish oil, with a yield of 61%.

25: $C_{10}H_{11}F_2NO_2$ M=215.20 g·mol$^{-1}$
Rf: 0.17 (cyclohexane/ethyl acetate) 8/2.
NMR $^{19}$F (CDCl$_3$, 282.5 Mz): −113.3 (brd, J=50 Hz, 2F).
Mass: (IE): 215 (M+•).

Synthesis of Compound 26

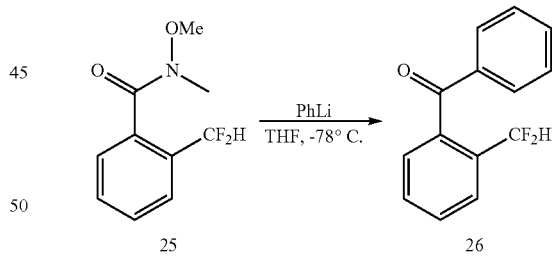

A solution of phenyllithium 1.8 M in diisobutylether (38.0 ml; 67.4 mmol; 2 eq.) is added to a round-bottom flask under an inert atmosphere which contains a solution of compound 25 (7.25 g, 33.7 mmol, 1 eq.) in dry tetrahydrofuran (75 mL) at −78° C. The reaction mixture is stirred for one hour at this temperature. A saturated aqueous ammonium chloride solution is then added at ambient temperature and the reaction medium is extracted with ethyl acetate. The organic phase is then dried over magnesium sulphate and concentrated. The residue is then purified on a chromatography column (9/1 cyclohexane/ethyl acetate eluent) in order to produce compound 26 in the form of a yellow oil, with a yield of 77%.

26: $C_{14}H_{10}F_2O$ M=232.23 g·mol$^{-1}$
Rf: 0.52 (cyclohexane/ethyl acetate) 8/2.

NMR $^{19}$F (CDCl$_3$, 282.5 Mz): −112.2 (d, J=56 Hz, 2F).

Mass: (IE): 232 (M+•).

Synthesis of Compound 27

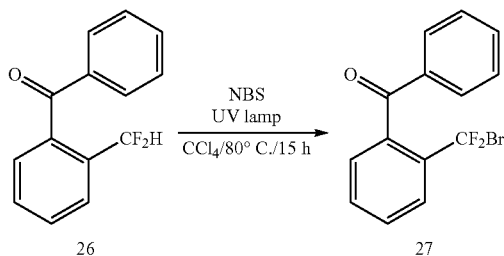

N-bromosuccinimide (0.926 g; 5.2 mmol; 2.1 eq.) is added to a quartz reactor under an inert atmosphere, which is surmounted by a mercury vapour UV lamp provided with a cooling system, and which contains a solution of compound 26 (0.575 g; 2.48 mmol; 1 eq.) in carbon tetrachloride (15 mL; distilled over P$_2$O$_5$). The reaction medium is refluxed and is irradiated for 15 h, making a second addition of N-bromosuccinimide (0.926 g; 5.2 mmol; 2.1 eq.) after 7 h. The mixture is washed with water and extracted with dichloromethane. The organic phase is dried over magnesium sulphate and then concentrated. The residue is then purified via a chromatography column (9/1 cyclohexane/ethyl acetate eluent) in order to produce compound 27, in the form of a colourless oil, with a yield of 45%.

27: C$_{14}$H$_9$BrF$_2$O M=331.12 g·mol$^{-1}$

Rf: 0.45 (cyclohexane/ethyl acetate) 8/2.

NMR $^{19}$F (CDCl$_3$, 282.5 Mz): −40.5 (s, 2F).

Mass: (IE): 331 (M+•).

Synthesis of Compound 28 and 29d1/d2

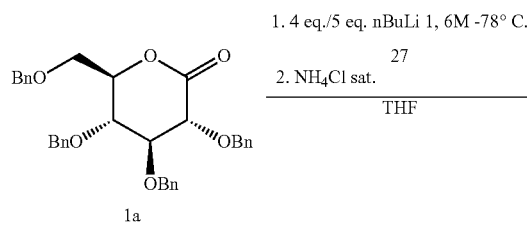

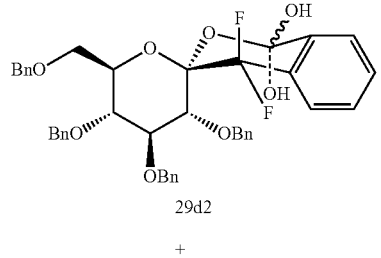

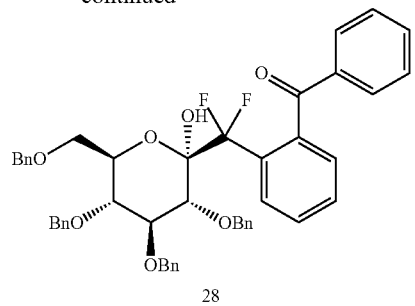

A 1.6 M solution of n-butyllithium in hexane (0.580 mL; 0.93 mmol; 5 eq.) is added to a round-bottom flask under an inert atmosphere, which contains a solution of 27 (0.304 g; 0.74 mmol; 4 eq.) and the lactone 1a (0.100 mg; 0.186 mmol; 1 eq.) in THF (10 mL) at −78° C. The cooling bath was removed and the reaction mixture was stirred overnight. A saturated aqueous ammonium chloride solution is then added at ambient temperature. The reaction medium is extracted with ethyl acetate and then dried over magnesium sulphate, prior to being concentrated. The residue is then purified on a chromatography column (90/10 cyclohexane/ethyl acetate eluent) to produce compound 29d2 and 28 in the form of a colourless oil.

28 et 29d2 C$_{48}$H$_{44}$F$_2$O$_7$ M=770.86 g·mol$^{-1}$

NMR $^{19}$F (CDCl$_3$, 282.5 MHz):

29d2: −93.6 (d, 263 Hz, 1F); −122.8 (d, 263 Hz, 1F)

28: −97.5 (d, 258 Hz, 1F); −101.8 (d, 258 Hz, 1F)

Mass (ESI$^+$): 753.2 (M−H$_2$O+H); 788.2 (M+H$_2$O)

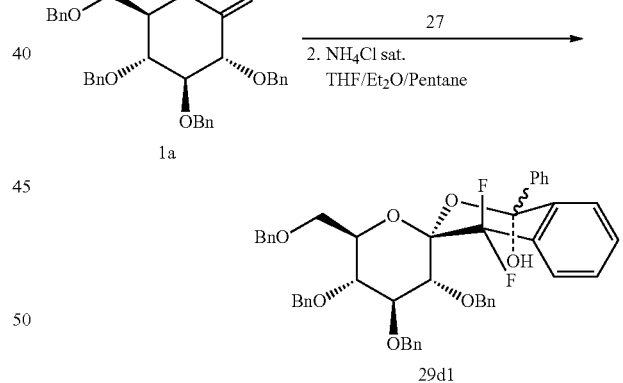

A 1.6 M solution of n-butyllithium in hexane (0.200 mL; 0.32 mmol; 2 eq.) is added to a round-bottom flask under an inert atmosphere, which contains a solution of 27 (100 mg; 0.32 mmol; 2 eq.) and the lactone 1a (0.86 mg; 0.16 mmol; 1 eq.) in a mixture of tetrahydrofuran, diethyl ether and pentane, in proportions of 5/1/1 (3.5 mL) at −90° C. The mixture is stirred for 1 h 30 min at this temperature. A saturated aqueous ammonium chloride solution is then added at ambient temperature. The reaction medium is extracted with ethyl acetate and then dried over magnesium sulphate, prior to being concentrated. The residue is then purified on a chromatography column (95/5 cyclohexane/ethyl acetate eluent) to produce compound 29d1, in the form of colourless oil, with a yield of 21%.

29d1: $C_{48}H_{44}F_2O_7$ M=770.86 g·mol$^{-1}$
NMR $^{19}$F (CDCl$_3$, 282.5 MHz): −92.8 (1F, d, J=259 Hz); −120.2 (1F, d, J=259 Hz).
Mass (ESI$^+$): 753.2 (M−H$_2$O+H); 788.2 (M+H$_2$O).
Synthesis of Compound 30

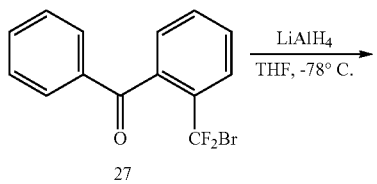

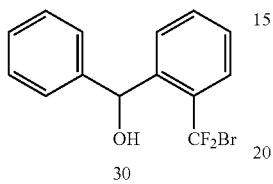

Lithium aluminium hydride (69.0 mg, 1.72 mmol, 1 eq.) is added in small portions, over a period of 15 min into a round-bottom flask under an inert atmosphere which contains a solution of 27 (0.54 g, 1.72 mmol; 1 eq.) in dry THF (17 mL) at −78° C. The solution is stirred for 1 h before a saturated ammonium chloride aqueous solution (a few drops) is added. The solution is filtered through celite and dried over magnesium sulphate, prior to being concentrated. The residue is then purified on a chromatography column (95/5 cyclohexane/ ethyl acetate eluent) to produce compound 30, in the form of a light yellow liquid with a yield of 61%.
30: $C_{14}H_{11}BrF_2O$ M=313.14 g·mol$^{-1}$
NMR $^{19}$F (CDCl$_3$, 282.5 MHz): −42.5 (d, J=160 Hz, 1F); −36.6 (d, J=160 Hz, 1F).
Mass (EI): 231 (M−Br).
Synthesis of Compound 31

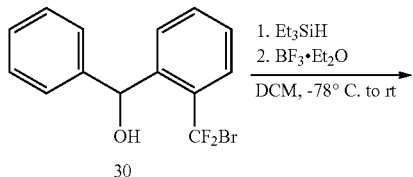

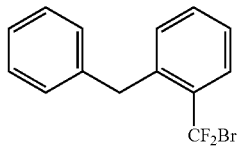

Triethylsilane (1.6 mL, 10.12 mmol, 10 eq.) and boron trifluoride etherate (0.639 mL, 5.06 mmol, 5 eq.) are added successively into a round-bottom flask under an inert atmosphere which contains a solution of 30 (0.317 g, 1.01 mmol, 1 eq.) in dry dichloromethane (DCM) (15 mL) at −78° C. The cooling bath was removed and the reaction mixture was stirred overnight at ambient temperature. A saturated aqueous ammonium chloride solution is then added. The reaction medium is extracted with dichloromethane and then dried over magnesium sulphate, prior to being concentrated. The residue is then purified on a chromatography column (100 cyclohexane eluent) to produce compound 31, in the form of colourless oil, with a yield of 81%.
31: $C_{14}H_{11}BrF_2$ M=297.11 g·mol$^{-1}$
NMR $^{19}$F (CDCl$_3$, 282 MHz): −41.2 (s, 2F).
Mass (EI): 217 (M−Br).
Synthesis of Compound 32

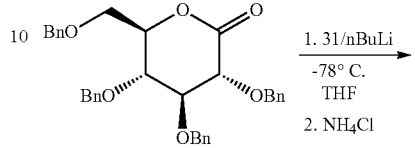

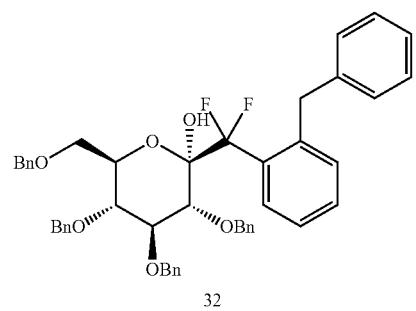

Compound 32 is prepared according to the procedure previously described (synthesis of compound 14a) from lactone 1a (0.100 g, 0.18 mmol, 1 eq.), compound 31 (0.166 g, 0.56 mmol, 3 eq.), and 1.5 M n-buthyllithium (0.37 mL, 0.56 mmol, 3 eq.) to give a colorless oil, with a yield of 28%.
32: $C_{48}H_{46}F_2O_6$ M=756.87 g·mol$^{-1}$
NMR $^{19}$F (CDCl$_3$; 282.5 MHz): −108.9 (d, J=269 Hz, 1F); −101.2 (, d, J=270 Hz, 1F).
Mass (ESI$^+$): 777.33 (M+H$_2$O); 1529.53 (2M+H$_2$O).
Synthesis of Compound 34

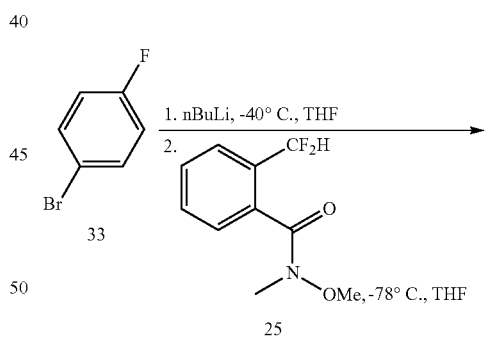

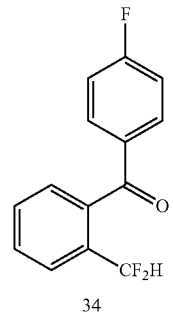

A 1.5M solution of n-butyllithium in hexane (12.9 mL, 19.3 mmol, 2.8 eq.) is added to a round-bottom flask under an inert atmosphere, which contains a solution of 33 (2.3 mL, 20.7 mmol, 3 eq.) in anhydrous THF (50 mL) at −10° C. The mixture is stirred for 2 h at −40° C. The temperature of the solution is brought down to −78° C. and a solution of 25 (1.48 g, 6.90 mmol, 1 eq.) in THF (20 mL) is added at this temperature. The mixture is stirred for an additional 30 min and saturated ammonium chloride aqueous solution is added. The reaction medium is extracted with ethyl acetate and then dried over magnesium sulphate, prior to being concentrated. The residue is then purified on a chromatography column (100/0 to 97/03 cyclohexane/ethyl acetate eluent) to produce compound 34, in the form of a greenish oil, with a yield of 84%.

34: $C_{14}H_9F_3O$ M=250.22 g·mol$^{-1}$

NMR $^{19}$F (CDCl$_3$, 282.5 MHz): −124.4 (d, J=56 Hz, 2F); 103.5 (m, 1F).

Mass (EI): 75-95-123-155-202-230-250.

Synthesis of Compound 35

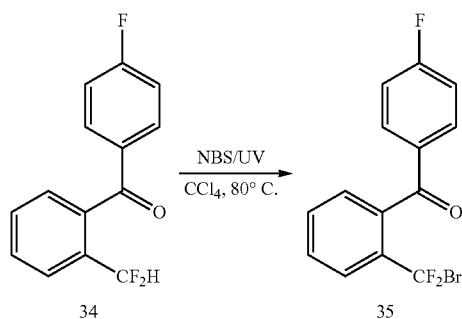

Compound 34 (1.45 g, 5.79 mmol, 1 eq.) was brominated with N-bromosuccinimide (4.33 g, 24.3 mmol, 4.1 eq.) according to the procedure previously described (synthesis of compound 27) to produce compound 35 in the form of a colourless oil, with a yield of 80%.

35: $C_{14}H_8BrF_3O$ M=329.11 g·mol$^{-1}$

NMR $^{19}$F (CDCl$_3$, 282.5 MHz): −103.6 (m, 1F); −40.6 (s).

Mass (EI): 75-95-123-201-229-249 (M−Br).

Synthesis of Compound 37

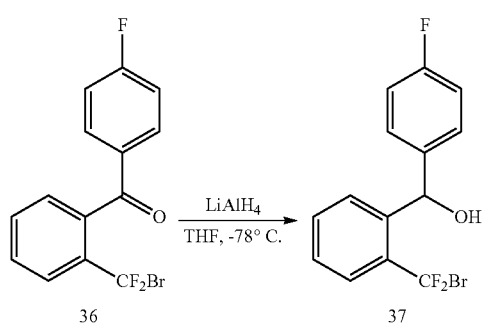

A solution of 36 (0.95 mg, 2.90 mmol, 1 eq.) in dry THF (13 mL) is added to a round-bottom flask under an inert atmosphere which contains a suspension of lithium aluminium hydride (0.11 g, 2.90 mmol, 1 eq.) in dry THF (13 mL) at −78° C. The solution is stirred for 1 h 30 before a saturated ammonium chloride aqueous solution (a few drops) is added. The solution is filtered through celite and dried over magnesium sulphate, prior to being concentrated. The residue is then purified on a chromatography column (98/02 to 80/20 cyclohexane/ethyl acetate eluent) to produce compound r, in the form of an orange oil with a yield of 70%.

37: $C_{14}H_{10}BrF_3O$ M=331.13 g·mol$^{-1}$

NMR $^{19}$F (CDCl$_3$, 282.5 MHz): −36.7 (d, J=159 Hz, 1F); −42.6 (d, J=159 Hz, 1F); −115.1 (m, 1F).

Mass (EI): 77-97-125-127-183-201-211-231-249-330 (M).

Synthesis of Compound 38

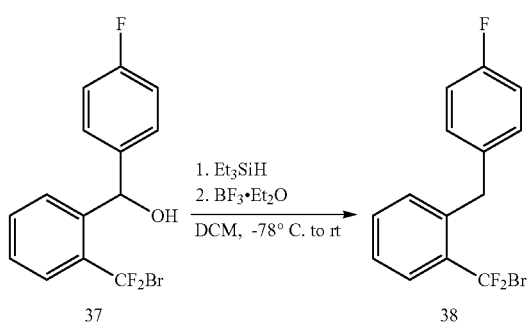

Compound 38 is prepared according to the procedure previously described (synthesis of 31) from compound 37 (0.477 g, 1.44 mmol, 1 eq.), triethylsilane (2.3 mL, 14.4 mmol, 10 eq.) and boron trifluoride etherate (0.91 mL, 7.20 mmol, 5 eq.), to give a yellowish liquid, with a yield of 100%.

38: $C_{14}H_{10}BrF_3$ M=315.13 g·mol$^{-1}$

NMR $^{19}$F (CDCl$_3$, 282.5 MHz): −41.3 (s, 2F); −116.0 (m, 1F).

Mass (EI): 109-183-215-235-314-316 (M)

Synthesis of Compound 39

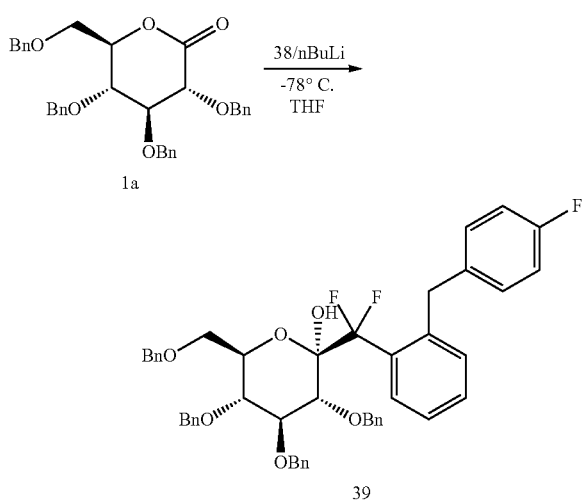

Compound 39 is prepared according to the procedure previously described (synthesis of 14a) from lactone 1a (0.097 g, 0.18 mmol, 1 eq.), compound 38 (0.295 g, 0.72 mmol, 4 eq.), and n-buthyllithium 1.5 M (0.66 mL, 0.44 mmol, 5.5 eq.) to give a yellow oil, with a yield of 66%.

39: $C_{48}H_{45}F_3O_6$ M=774.86 g·mol$^{-1}$

NMR $^{19}$F (CDCl$_3$; 282.5 MHz): −102.9 (d, J=254 Hz, 1F); −101.6 (d, J=254 Hz, 1F); −118.1 (m, 1F).

Mass (ESI$^+$): 792.33 (M+H$_2$O).

Synthesis of Compound 40

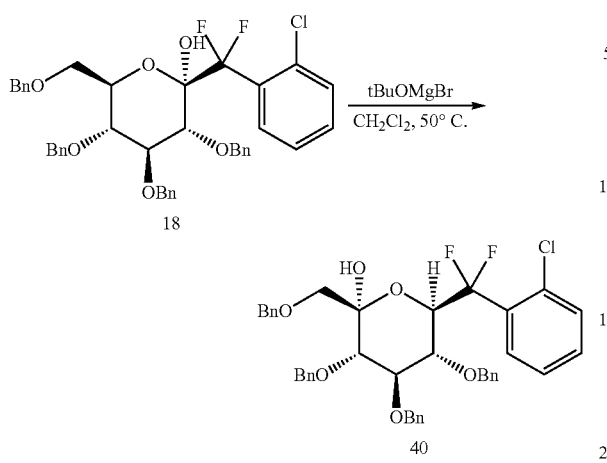

A 3M solution of ethylmagnesium bromide in diethyl ether (0.133 mL, 0.40 mmol, 5 eq.) is slowly added to a solution of tent-butanol (0.038 mL, 0.40 mmol; 5 eq.) in diethyl ether (1 mL). The mixture is stirred for 15 min at ambient temperature. A solution of 18 (0.056 g, 0.079 mmol, 1 eq) in dichloromethane (0.5 mL) is then slowly added. The mixture is warmed to 50° C. and stirred at this temperature for 3 days. A 1N aqueous solution of hydrochloric acid is then added at ambient temperature. The reaction medium is extracted with dichloromethane and then dried over magnesium sulphate, prior to being concentrated to produce compound 40 (no further purification) in the form of a colourless oil.

40: $C_{41}H_{39}ClF_2O_6$ M=700.24 g·mol$^{-1}$

NMR $^{19}$F (CD$_3$OD), 282.5 MHz: −98.4 (dd, J1=277 Hz, J2=7 Hz, 1F); −108.7 (dd, J1=272 Hz, J2=22 Hz, 1F).

Mass (ESI$^+$): 718.20 (M+H$_2$O); 1417.73 (2M+H$_2$O).

Synthesis of Compound 41

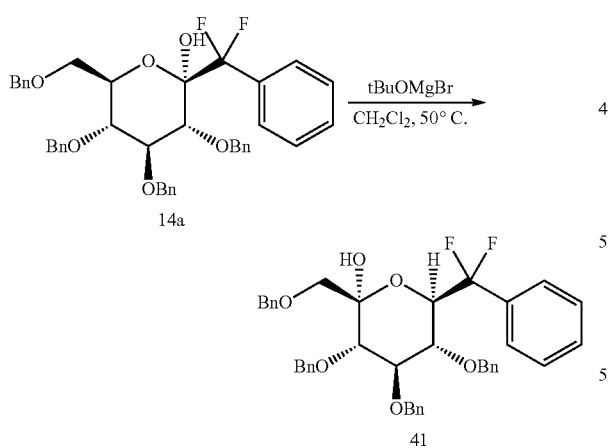

Compound 41 is prepared according to the procedure previously described (synthesis of compound 40) from compound 14a (0.200 g, 0.3 mmol, 1 eq.), a 3M solution of ethylmagnesium bromide in diethyl ether (0.50 mL, 1.5 mmol, 5 eq.) and tent-butanol (0.142 mL, 1.5 mmol, 5 eq.). The residue is purified on a chromatography column (98/2 to 85/15 cyclohexane/ethyl acetate eluent) to produce compound 41 in the form of a colourless oil with a yield of 34%

41: $C_{41}H_{40}F_2O_6$ M=666.75 g·mol$^{-1}$

Rf: 0.28 (cyclohexane/ethyl acetate 8/2).

NMR $^{19}$F (CDCl$_3$, 282.5 MHz): −96.4 (dd, J1=255 Hz, J2=5 Hz, 1F); −110.0 (dd, J1=254 Hz, J2=17 Hz, 1F).

Mass (ESI+): 684.13 (M+H$_2$O).

Synthesis of Compound 42

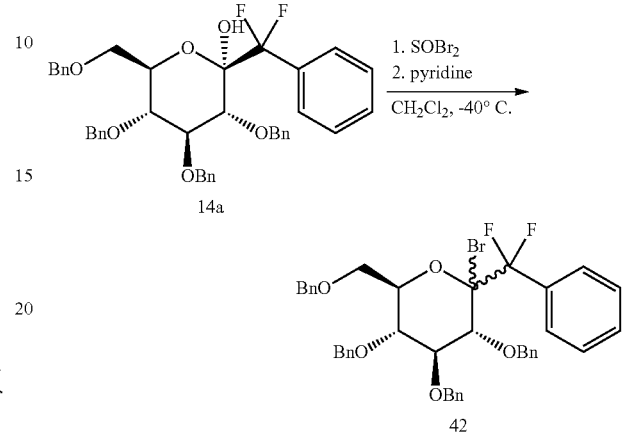

Thionyl bromide (0.018 mL, 0.23 mmol, 1.5 eq.) is added to a round-bottom flask under inert atmosphere which contains a solution of 14a (0.101 g, 0.15 mmol, 1 eq.) in dichloromethane at −40° C. The mixture is stirred for 2 h at this temperature before pyridine (0.018 g, 0.23 mmol, 1.5 eq.) is added. The solution is stirred for an additional period of 30 min at this temperature. The solution is then brought back to ambient temperature and a 1N aqueous solution of hydrochloric acid is added. The reaction medium is extracted with dichloromethane and then dried over magnesium sulphate, prior to being concentrated. The residue is then purified on a preparative thin layer chromatography (85/15 cyclohexane/ethyl acetate eluent) to produce compound 42, in the form of white crystals, with a yield of 13%.

41: $C_{41}H_{39}BrF_2O_5$ M=729.65 g·mol$^{-1}$

NMR $^{19}$F (CDCl$_2$, 282.5 MHz): −100.3 (d, J=247 Hz, 1F); −101.2 (d, J=248 Hz, 1F).

Mass (ESI$^+$): 746.07-747.93 (M+H$_2$O); 769.00 (M+K).

Synthesis of Compound 43

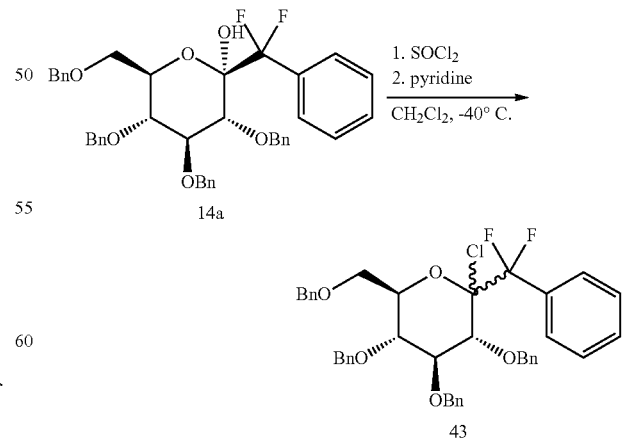

Thionyl chloride (0.037 mL, 0.51 mmol, 1.5 eq.) is added dropwise to a round-bottom flask under inert atmosphere which contains a solution of 14a (0.226 g, 0.34 mmol, 1 eq.) in dichloromethane (3.3 mL) at −30° C. The mixture is stirred for 30 min at this temperature before pyridine (0.041 mL, 0.51 mmol, 1.5 eq) is added. The solution is stirred for an additional period of 30 min at this temperature. The solution is then brought back to ambient temperature and a 2N aqueous solution of hydrochloric acid is added. The reaction medium is extracted with dichloromethane, washed with brine and then dried over magnesium sulphate, prior to being concentrated. The residue is then purified on a chromatography column (98/2 to 90/10 cyclohexane/ethyl acetate eluent) to produce compound 43 as a mixture of 2 anomers (60/40), in the form of an orange oil, with a yield of 77%.

43: $C_{41}H_{39}ClF_2O_5$ M=685.2 g·mol$^{-1}$

NMR $^{19}$F (CDCl$_2$), 282.5 MHz: −98.2 (d, J=250 Hz, 1F); −101.5 (d, J=250 Hz, 1F); −102.5 (d, J=248 Hz, 1F); −104.4 (d, J=249 Hz, 1F).

Mass (ESI$^+$): 666.4 (M−HCl+H$_2$O); 671.47 (M−HCl+Na); 1314.13 ((2(M−HCl)+H$_2$O); 1318.80 (2(M−HCl)+Na).

Synthesis of Compound 44d1/44d2

First Process:

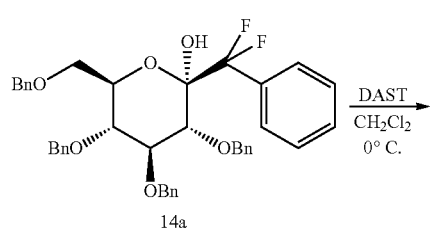

14a

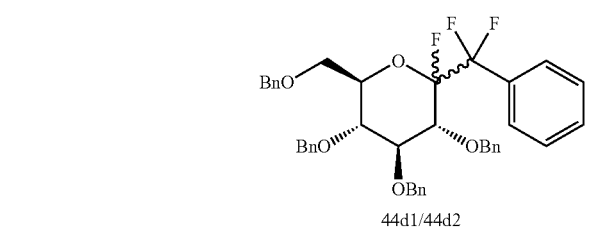

44d1/44d2

Diethylaminosulfur trifluoride (DAST) (0.28 mL, 2.27 mmol, 2 eq.) is added into a round-bottom flask under an inert atmosphere which contains a solution of 14a (0.757 g, 1.14 mmol, 1 eq.) in dichloromethane (12 mL) at 0° C. The mixture is stirred for 1 h at this temperature and overnight at room temperature. The reaction mixture is cooled to 0° C. and methanol and solid sodium bicarbonate are carefully added at this temperature. Water id added and the reaction medium is extracted with dichloromethane, washed with water and brine and then dried over magnesium sulphate, prior to being concentrated. The residue is then purified on a preparative thin layer chromatography (80/20 cyclohexane/ethyl acetate eluent) to produce 44d1 and 44d2 as a mixture of two diastereomers in 40/60 proportion, in the form of a colourless oil, with a yield of 54%.

Second Process:

Synthesis of Compound 44d1/44d2

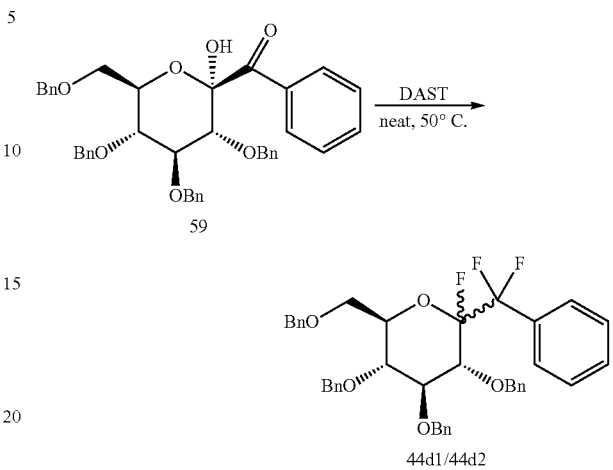

A solution of compound 59 (see below for the preparation of compound 59) (0.032 g, 0.049 mmol, 1 eq.) in diethylaminosulfur trifluoride (0.061 mL, 0.49 mmol, 10 eq.) neat is stirred overnight at 50° C. in a round-bottom flask under an inert atmosphere. Solid sodium bicarbonate and water are then carefully added at 0° C. The reaction medium is extracted with dichloromethane, washed with brine then dried over magnesium sulphate prior to being concentrated. The residue is then purified on a preparative thin layer chromatography (80/15 cyclohexane/ethyl acetate eluent) in order to produce compound 63 in the form of a colourless oil which slowly crystallizes, with a yield of 30%.

44d1/44d2: $C_{41}H_{40}F_3O_5$ M=668.74 g·mol$^{-1}$

NMR $^{19}$F (CDCl$_3$, 282.5 MHz): 44d1: −106.2 (m, 1F); −107.2 (m, 2F).

44d2: −108.4 (m, 2F); −140.5 (m, 1F).

Mass (ESI$^+$): 686.20 (M+H$_2$O).

Synthesis of Compound 46

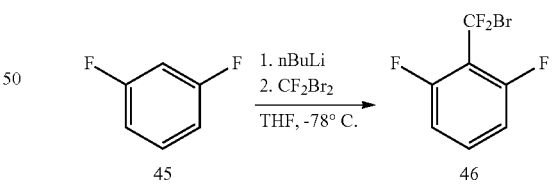

A solution of n-butyllithium 1.4 M in hexane (0.310 mL; 0.44 mmol; 1 eq.) is added dropwise into a round-bottom flask under an inert atmosphere, which contains the difluorobenzene 29 (0.05 g; 0.44 mmol; 1 eq.) in tetrahydrofurane (5 mL) at −78° C. After stirring for 1 h at this temperature, the dibromodifluoromethane (0.080 mL; 0.88 mmol; 2 eq.) is added. The reaction mixture is stirred for 1 additional h at −78° C. and then a saturated aqueous ammonium chloride solution is added at ambient temperature. The mixture is extracted with ethyl acetate, dried over magnesium sulphate, filtered and concentrated in order to produce compound 30.

30: $C_7H_3BrF_4$ M=243.00 g·mol$^{-1}$
NMR $^{19}$F (CDCl$_3$, 282.5 Mz): −40.70 (t, J=30 Hz, 2F).
Mass: (ESI+): 163 (M−Br)

Synthesis of Compound 47-A and 47-B

First Process:

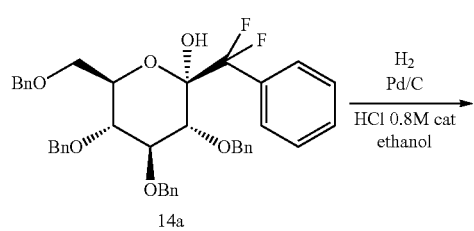

14a

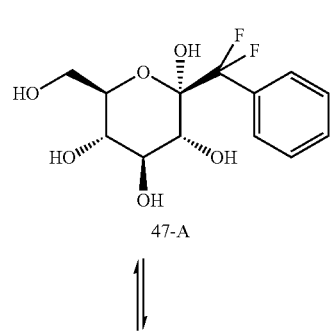

47-A

⇅

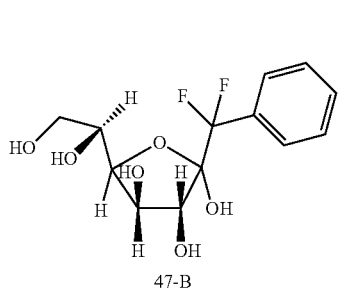

47-B

Compound 14a (0.319 g, 0.48 mmol, 1 eq.) is placed inside a round-bottom flask and dissolved in a mixture of ethanol (4 mL) and 0.8M aqueous hydrochloric acid solution (two drops), in the presence of a spatula tip of Pd/C under a hydrogen atmosphere. The mixture is stirred for 48 h, then Millipore-filtered and evaporated to produce compound 47-A/47-B in the form of a white powder with a quantitative yield.

Second Process:

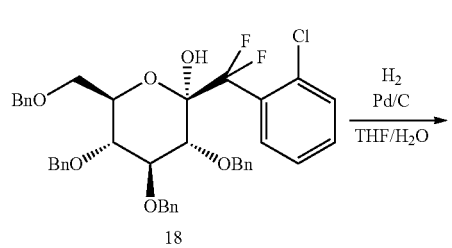

18

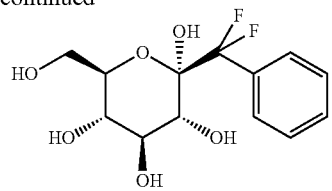

47-A

⇅

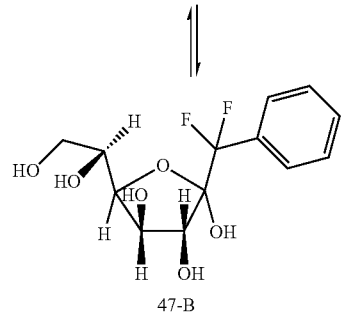

47-B

Compound 18 (41.3 mg; 0.059 mmol; 1 eq.) is deprotected according to the procedure previously described (synthesis of compound 9a) to produce compound 47-A and 47-B in the form of a white powder with a quantitative yield.

47-A/47-B: $C_{13}H_{16}F_2O_6$ M=306.26 g·mol$^{-1}$
NMR $^{19}$F (D$_2$O, 282.5 MHz): 47-A: −109.7 (d, J=251 Hz, 1F); −107.2 (d, J=251 Hz, 1F); 47-B: −110.4 (d, J=250 MHz, 1F); −108.9 (d, J=253 Hz, 1F).
Mass: (ESI−): 305 (M−H); 341-343 (M+Cl).

Synthesis of Compound 48-A and 48-B

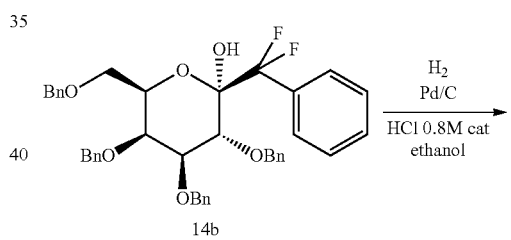

14b

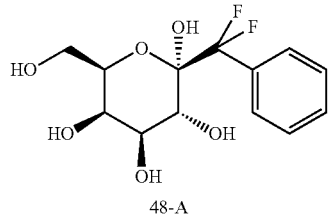

48-A

⇅

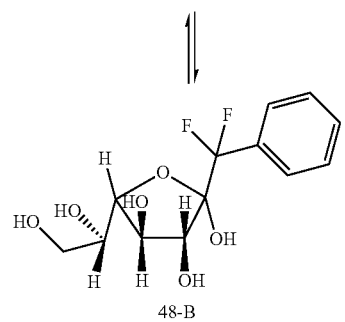

48-B

Compound 14b (167 mg, 0.25 mmol, 1 eq.) is deprotected according to the procedure described previously (synthesis of 47A-47-B, first process) to produce compound 48-A and 48-B in the form of a white powder with a quantitative yield.

48-A/48-B: $C_{13}H_{16}F_2O_6$ M=306.26 g·mol$^{-1}$ $^{19}$F NMR (D$_2$O, 282.5 MHz):

48-B: −112.4 (d, J=253 Hz, 1F); −114.2 (d, J=253 Hz, 1F).

48-A: −109.5 (d, J=252 Hz, 1F); −112.5 (d, J=250.6 Hz).

Mass (ESI$^-$): 304.8 (M−H); 340.8 (M+Cl).

Synthesis of Compound 49-A and 49-B

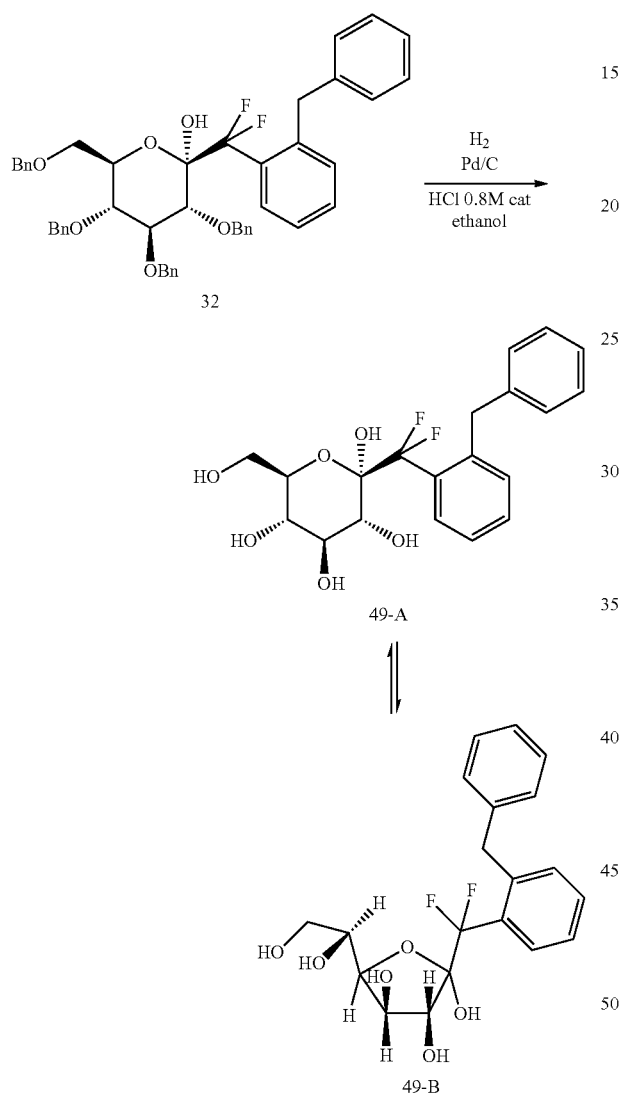

Compound 32 (39 mg, 0.05 mmol, 1 eq.) is deprotected according to the procedure described previously (synthesis of 47A-47-B, first process) to produce compound 49-A and 49-B in the form of a white powder with a quantitative yield.

49-A/49-B: $C_{48}H_{22}F_2O_6$ M=396.38 g·mol$^{-1}$

NMR $^{19}$F (CD$_3$OD, 282.5 MHz):

49-A: −100.7 (d, J=258 Hz, 1F); −104.9 (d, J=258 Hz, 1F)

49-B: −102.8 (d, J=258 Hz, 1F); −104.0 (d, J=259 Hz, 1F)

Mass (ESI$^-$): 395.33 (M−H); 431.33 (M+Cl); 791.40 (2M−H).

Synthesis of Compound 50-A and 50-B

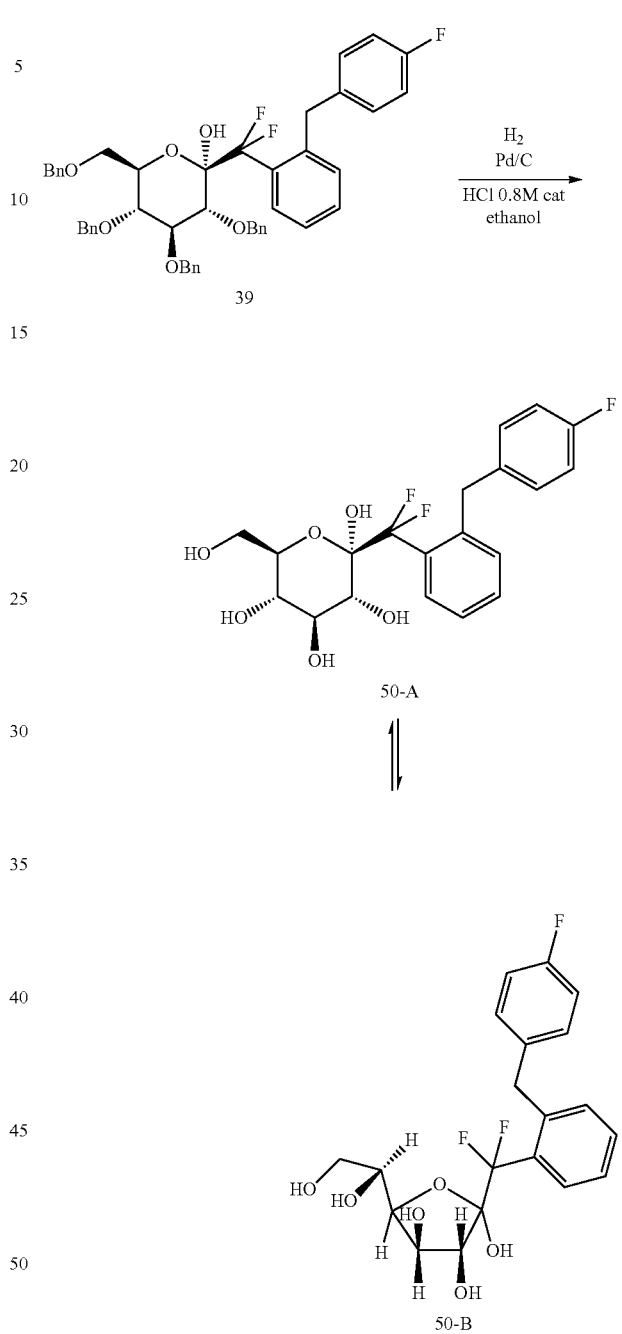

Compound 39 (59 mg, 0.07 mmol, 1 eq.) is deprotected according to the procedure described previously (synthesis of 47A-47-B, first process) to produce compound 50-A and 50-B in the form of a white powder with a 78% yield.

50-A/50-B: $C_{20}H_{21}F_3O_6$ M=414.37 g·mol$^{-1}$

RMN $^{19}$F (CD$_3$OD, 282.5 MHz):

Major form 50-A: −100.8 (d, J=258 Hz, 1F); −104.0 (d, J=259 Hz, 1F); −120.3 (dddd, 1F)

Minor form 50-B: −102.0 (d, J=258 Hz, 1F); −104.1 (d, J=259 Hz, 1F); −120.2 (dddd, 1F)

Mass (ESI$^-$): 413.29 (M−H).

Synthesis of Compound 51

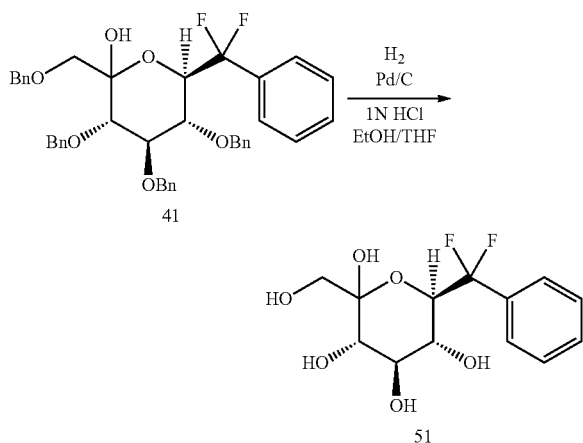

Compound 41 (45.2 mg, 0.06 mmol, 1 eq.) is placed in a round-bottom flask and dissolved in a mixture of ethanol (1 mL), tetrahydrofuran (1 mL) and 1M hydrochloric acid solution (two drops) in the presence of a spatula tip of Pd/C, under a hydrogen atmosphere. The mixture is stirred for 48 h, then Millipore-filtered and evaporated in order to produce compound 51, in the form of a white solid, with 96% yield.

51: $C_{14}H_{20}F_2O_6$ M=322.30 g·mol$^{-1}$

NMR $^{19}$F (CDCl$_3$, 282.5 MHz): −98.7 (dd, J1=255 Hz, J2=7 Hz, 1F); −107.7 (dd, J1=255 Hz; J2=13 Hz, 1F).

Mass (ESI−): 304.9 (M−H), 340.9 (M+Cl).

Synthesis of Compound 52

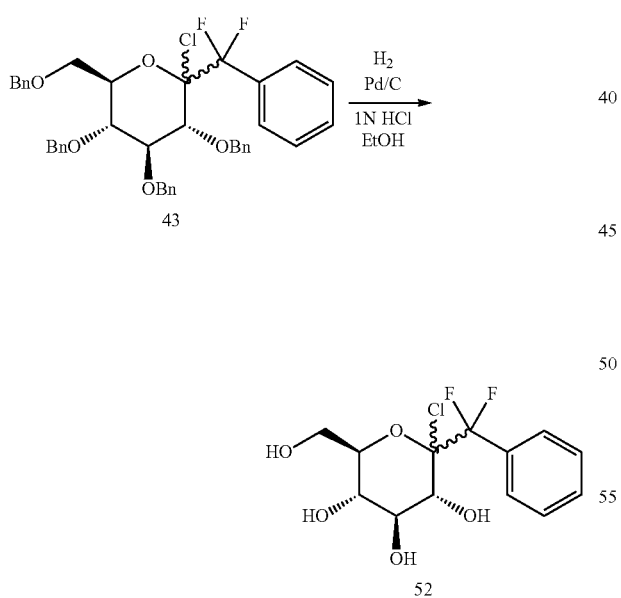

Compound 43 (44.3 mg, 0.07 mmol, 1 eq.) is deprotected according to the procedure described previously (synthesis of 47A-47-B, first process) to produce compound 52 in the form of a white solid, with 86% yield.

52: $C_{13}H_{15}ClF_2O_5$ M=324.71 g·mol$^{-1}$

Mass (ESI−): 358.9 (M+Cl).

Synthesis of Compound 54

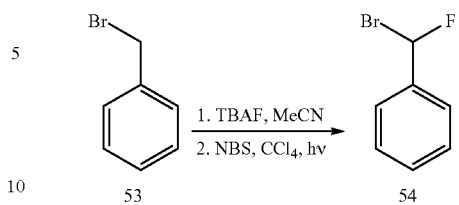

Benzyl bromide (2.4 mL, 20.0 mmol, 1 eq.) is added dropwise to a round-bottom flask under an inert atmosphere which contains a solution of tetra-n-butylammonium fluoride (12.62 g, 40.0 mmol, 2 eq.) in dry acetonitrile (40 mL) at ambient temperature. The reaction is stirred overnight at this temperature. Water is added (30 mL) and the reaction medium is extracted with pentane, and then dried over magnesium sulphate, prior to being concentrated to produce fluoro-methyl benzene with no further purification. Fluoro-methyl benzene (1.37 g, 12.4 mmol, 1 eq.) is then added into a reactor under an inert atmosphere which contains a suspension of N-bromosuccinimide (2.21 g, 12.4 mmol, 1 eq.) in carbon tetrachloride (40 mL), surmounted by a mercury vapour UV lamp. The reaction mixture is irradiated overnight at ambient temperature. The mixture is then filtered, extracted with dichloromethane, washed with water, dried over magnesium sulphate, filtered and then concentrated. The residue is then purified on a chromatography column (100% cyclohexane eluent) to produce compound 54 in the form of a colourless oil, with a 24% overall yield.

54: $C_7H_6BrF$ M=189.02 g·mol$^{-1}$

NMR $^{19}$F (CDCl$_3$, 282.5 MHz): −130.1 (d, J=49 Hz, 1F).

Mass (CI+): 109 (M+H—Br)

Synthesis of Compound 56

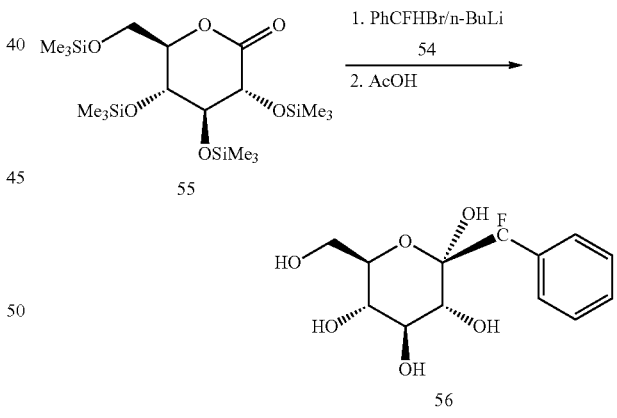

A 1.5 M solution of n-butyllithium in hexane (0.85 mL, 1.24 mmol, 5.5 eq.) is added to a round-bottom flask under an inert atmosphere, which contains a solution of compound 54 (0.170 mg, 0.40 mmol, 4 eq.) and lactone 55 (0.105 g, 0.22 mmol, 1 eq.) in dry tetrahydrofuran (3 mL) at −90° C. The mixture is stirred for 2 hours at this temperature. A 1% aqueous acetic acid solution is added at this temperature and the mixture is brought back to ambient temperature. The reaction medium is extracted with diethyl ether, washed with brine and then dried over magnesium sulphate, prior to being concentrated. The residue is then diluted in methanol and a 1% aqueous solution of acetic acid (5 mL) is added. The mixture is stirred overnight at ambient temperature. The solvent is removed and the reaction medium is extracted with ethyl acetate and then dried over magnesium sulphate, prior to being concentrated. The residue is then purified on a chromatography column (100/0 to 90/10 dichloromethane/methanol eluent) to produce compound 56 as a mixture of two diastereomers in 80/20 proportion, in the form of a colourless oil, with a yield of 4%.

56: $C_{13}H_{17}FO_6$ M=288.27 g·mol$^{-1}$

NMR $^{19}F$ (MeOD, 282.5 MHz): −187.3 (d, J=45 Hz, 1F); −200.0 (d, J=45 Hz, 1F).

Mass (ESI+): 306.1 (M+H$_2$O); 311.0 (M+Na); 327.1 (M+K).

Synthesis of Compound 57

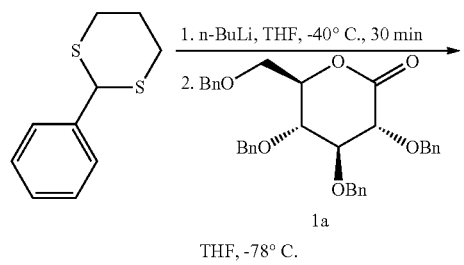

1a

THF, −78° C.

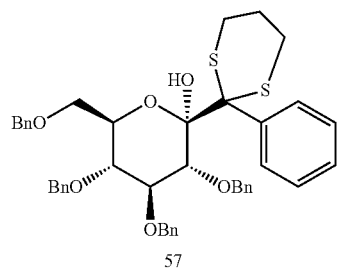

57

A 1.6 M solution of n-butyllithium in hexane (45.6 mL, 73.0 mmol, 4.5 eq.) is added dropwise to a round-bottom flask under an inert atmosphere which contains a solution of 2-phenyl-1,3-dithiane (14.04 g, 71 mmol, 4.4 eq.) in dry tetrahydrofuran at −40° C. The mixture is stirred at −40° C. for 30 min before being cooled to −78° C. A solution of lactone 1a (8.75 g, 16 mmol, 1 eq.) in tetrahydrofuran (10 mL) cooled at −78° C. is added dropwise to the reaction mixture. At the end of the addition, the cooling bath is removed and saturated aqueous ammonium chloride solution (2 mL) is added. The reaction medium is extracted with diethyl ether, washed with brine and then dried over magnesium sulphate, prior to being concentrated. The residue is then purified on chromatography column (95/5 cylohexane/ethyl acetate eluent) to produce 57 in the form of a white solid with a yield of 57%. The product can be recristallised from acetonitrile to give colourless crystals.

57: $C_{44}H_{46}O_6S_2$ M=734.96 g·mol$^{-1}$

Rf: 0.45 (cyclohexane/ethyl acetate 8/2).

Mass (ESI+): 752.20 (M+H$_2$O); 1487.07 (2M+H$_2$O); 1507.87 (2M+K).

Synthesis of Compound 58

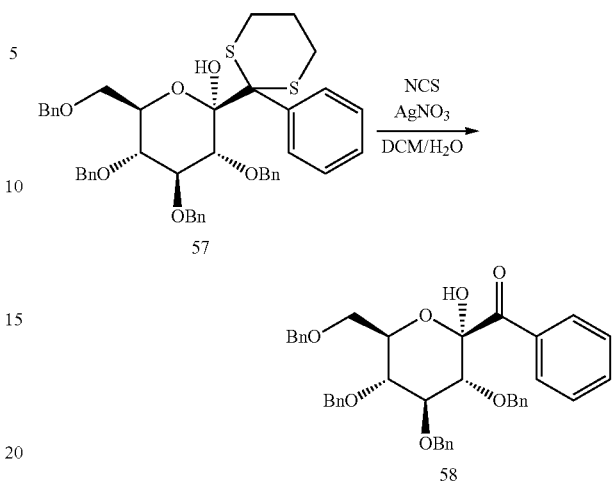

A solution of 57 (1.75 g, 2.38 mmol; 1 eq.) in dichloromethane (4 mL) is quickly added to a round-bottom flask which contains N-chlorosuccinimide (1.27 g, 9.51 mmol, 4 eq.) and silver nitrate (1.82 g, 10.7 mmol, 4.5 eq.) in a mixture of dichloromethane and water in proportions of 8/2 (50 mL) at ambient temperature. The mixture is vigorously stirred for 15 min. The reaction medium is extracted with dichloromethane and then washed with a saturated aqueous solution of sodium sulfite (2 mL), sodium carbonate (2 mL) and brine (2 mL) then dried over magnesium sulphate, prior to being concentrated The residue is then purified on chromatography column (90/10 cylohexane/ethyl acetate eluent) to produce 58 in the form of a colourless oil with a yield of 79%.

58: $C_{41}H_{40}O_7$ M=644.75 g·mol$^{-1}$

Rf: 0.42 (cyclohexane/ethyl acetate 8/2).

Mass (ESI$^+$): 662.33 (M+H$_2$O).

Synthesis of Compound 59

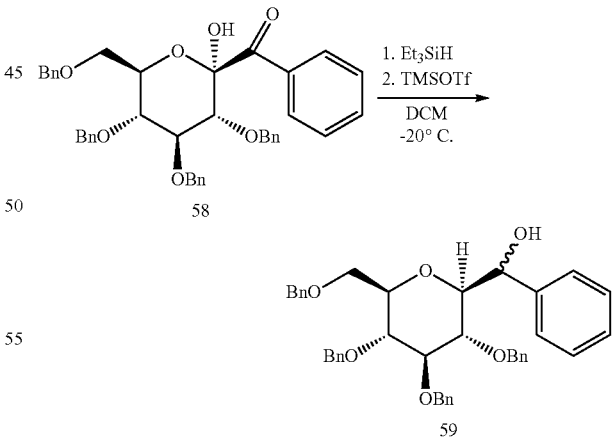

Triethylsilane (0.200 mL, 0.124 mmol, 8 eq.) and trimethylsilyl trifluoromethanesulfonate (0.028 mL, 0.15 mmol, 1 eq.) are successively added, to a round-bottom flask under an inert atmosphere which contains a solution of 58 (0.100 g, 0.15 mmol, 1 eq.) in dry dichloromethane (3 mL) at −20° C. The mixture is stirred at this temperature for 7 h. A saturated aqueous sodium carbonate solution is then added at ambient temperature and the reaction medium is extracted with dichloromethane, washed with brine then dried over magnesium sulphate prior to being concentrated. The residue is then purified on a chromatography column (10/0 to 8/2 cyclohexane/ethyl acetate eluent) in order to produce compound 59 in the form of a white solid, with a yield of 22%.

59: $C_{41}H_{40}O_6$ M=628.76 g·mol$^{-1}$

Rf: 0.27 (cyclohexane/ethyl acetate 8/2).

Mass (ESI$^+$): 629.27 (M+H); 646.20 (M+H$_2$O); 1274.13 (2M+H$_2$O); 1278.93 (2M+Na).

Synthesis of Compound 60

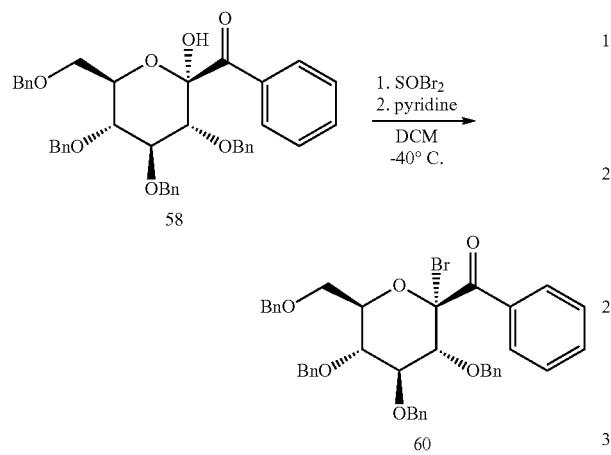

Compound 60 was prepared according to the procedure previously described (synthesis of compound 42) from compound 58 (0.100 g, 0.155 mmol, 1 eq.), thionyl bromide (0.018 mL, 0.132 mmol, 1.5 eq) and pyridine (0.019 mL, 0.232 mmol, 1.5 eq.) to give a colourless oil with a 51% yield.

60: $C_{41}H_{39}BrO_6$ M=707.66 g·mol$^{-1}$

Mass (ESI$^+$): 729.27-731.27-732.27 (M+Na); 745.27-747.20-747.93-749.07 (M+K).

Synthesis of Compound 61

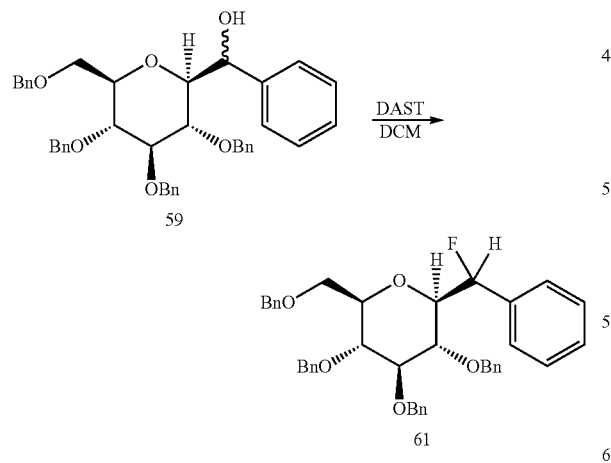

Compound 61 was prepared according to the procedure previously described (synthesis of compound 44d1/44d2) from compound 59 (0.055 g, 0.088 mmol, 1 eq.) and diethylaminosulfur trifluoride (0.018 mL, 0.15 mmol, 1.7 eq.), as a mixture of two diastereomers in 58/42 proportion, in the form of colourless crystals.

61: $C_{41}H_{40}F_3O_5$ M=632.76 g·mol$^{-1}$

NMR $^{19}$F (CDCl$_3$, 282.5 MHz):
−183.4 (dd, J=44.3 Hz, J2=14.4 Hz, 1F);
−197.2 (dd, J1=45.4 Hz, J2=27.8 Hz, 1F).

Mass (ESI$^+$): 650.20 (M+H$_2$O).

Synthesis of Compound 62

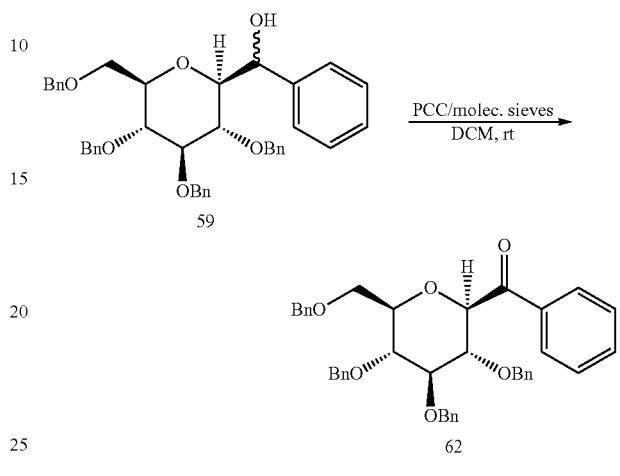

Pyridinium chlorochromate (0.01 mg, 0.05 mmol, 1.7 eq) is added to a round-bottomed flask under inert atmosphere, which contains a solution of compound 59 (0.020 g, 0.03 mmol, 1 eq.) in dry dichloromethane (2 mL) and molecular sieves. The mixture is stirred at ambient temperature overnight before another portion of PCC (1 eq.) is added. The mixture is stirred at ambient temperature for 5 h and then filtered. Solvent is removed and the residue is purified on preparative thin layer chromatography (8/2 cyclohexane/ethyl acetate eluent) in order to produce compound a in the form of a white solid, with a yield of 58%.

62: $C_{41}H_{40}O_6$ M=628.76 g·mol$^{-1}$

Rf: 0.39 (cyclohexane/ethyl acetate 8/2).

Mass (ESI$^+$): 629.27 (M+H); 646.20 (M+H$_2$O); 1274.13 (2M+H$_2$O); 1278.9 (2M+Na).

Synthesis of Compound 63

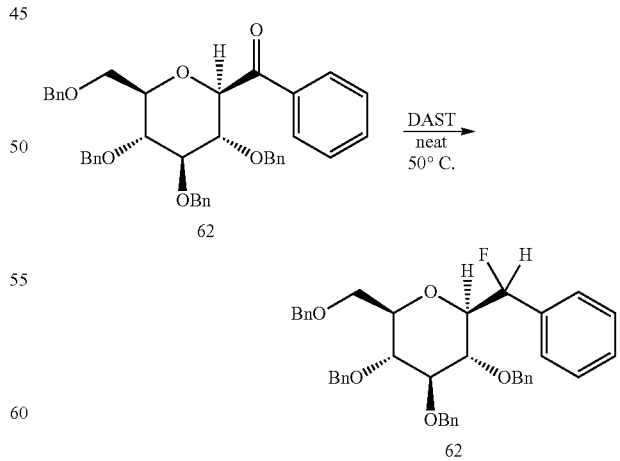

A solution of compound 62 (70.5 mg, 0.11 mmol, 1 eq.) in diethylaminosulfur trifluoride (0.300 mL) neat is stirred overnight at 50° C. in a round-bottom flask under an inert atmosphere. Additional diethylaminosulfur trifluoride (0.100 mL)

is then added at ambient temperature and the mixture is stirred at 50° C. for an additional 24 h. Solid sodium bicarbonate and water are then carefully added at 0° C. The reaction medium is extracted with dichloromethane, washed with brine then dried over magnesium sulphate prior to being concentrated. The residue is then purified on a chromatography column (90/10 to 85/15 cyclohexane/ethyl acetate eluent) in order to produce compound 63 in the form of a colourless oil which slowly crystallizes, with a yield of 30%.

63: $C_{41}H_{40}F_2O_5$ M=650.75 g·mol$^{-1}$

Rf: 0.48 (cyclohexane/ethyl acetate 8/2).

NMR $^{19}$F (CDCl$_3$, 282.5 MHz): −97.9 (dd, J1=4.12 Hz, J2=260.9 Hz, 1F); −109.4 (dd, J1=15 Hz, J2=257 Hz, 1F).

Mass (ESI$^+$): 668.20 (M+H$_2$O).

Synthesis of Compound 64

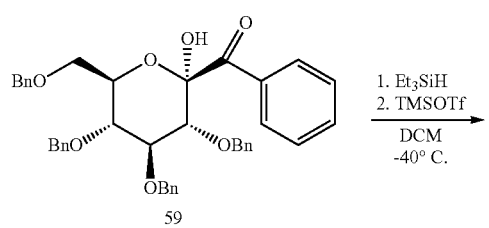

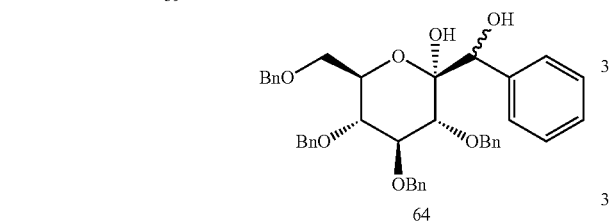

Triethylsilane (0.050 mL, 0.31 mmol, 4 eq.) and trimethylsilyl trifluoromethanesulfonate (TMSOTf) (0.035 mL, 0.19 mmol, 2.5 eq.) are successively added, to a round-bottom flask under an inert atmosphere which contains a solution of 59 (0.05 g, 0.077 mmol, 1 eq.) in dry dichloromethane (1.5 mL) at −40° C. The mixture is stirred at this temperature for 1 h. A saturated aqueous sodium carbonate solution is then added at ambient temperature and the reaction medium is extracted with dichloromethane, washed with brine then dried over magnesium sulphate prior to being concentrated. The residue is then purified on a chromatography column (10/0 to 80/20 cyclohexane/ethyl acetate eluent) in order to produce compound 64 in the form of a white solid, with a yield of 45%.

64: $C_{41}H_{42}O_7$ M=646.78 g·mol$^{-1}$

Mass (ESI$^+$): 644.27 (M+H$_2$O); 1311.07 (2M+H$_2$O).

Synthesis of Compound 65

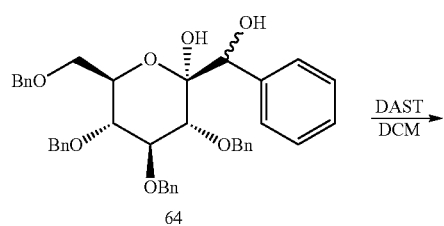

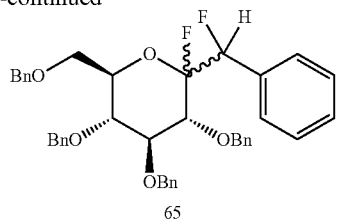

Compound 65 was prepared according to the procedure previously described (synthesis of compound 44d1/44d2) from compound 64 (0.022 g, 0.035 mmol, 1 eq.) and diethylaminosulfur trifluoride (0.017 mL, 0.14 mmol, 4 eq.) as a mixture of 4 diastereomers in 33/33/25/5 proportion, in the form of a colourless oil, with a 41% yield.

65: $C_{41}H_{40}F_2O_5$ M=650.75 g·mol$^{-1}$

NMR $^{19}$F (CDCl$_3$, 282.5 MHz):

−134.5 (ddd, J1=24 Hz, J2=18 Hz, J3=6.2 Hz, 1F); −192.0 (dd, J1=45 Hz, J2=17.5 Hz, 1F);

−135.9 (dd, J1=23 Hz, J2=5 Hz, 1F); −190.50 (dapp, J1=44 Hz, J2=5 Hz, 1F)

−115.3 (m, 1F); 189.3 (dd, J1=44 Hz, J2=17 Hz, 1F)

−111.9 (m, 1F); −189.8 (dd, J1=42 Hz, J2=9 Hz, 1F)

Mass (ESI$^+$): 650.20 (M+H$_2$O).

Synthesis of Compound 67

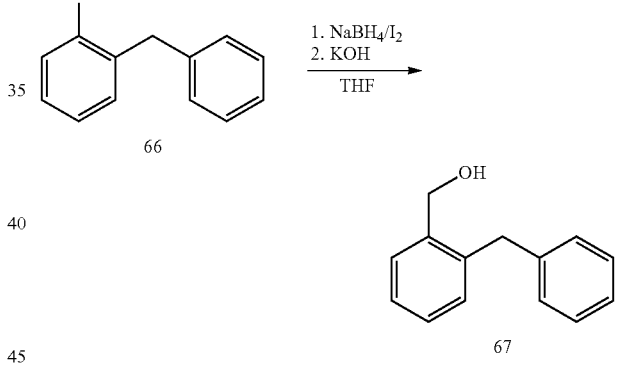

A solution of iodine (8.37 g, 33.0 mmol, 1 eq.) in dry tetrahydrofuran (60 mL) is added dropwise to a round-bottom flask under an inert atmosphere which contains a suspension of sodium borohydride (3.0 g, 79.0 mmol, 2.4 eq.) in dry tetrahydrofuran (60 mL) at 0° C. The mixture is stirred 5 min at this temperature and compound 66 is added. The mixture is refluxed overnight before being cooled to 0° C. Methanol (50 mL) is then added dropwise and the resulting mixture is stirred at ambient temperature for a further 30 min. Solvents are removed and a 20% potassium hydroxide aqueous solution (150 mL) is added to the residue. The solution is stirred for 4 h at ambient temperature. The reaction medium is extracted with dichloromethane and dried over magnesium sulphate prior to being concentrated to produce compound 67 in the form of a yellow oil, with a yield of 92%. The compound can be involved in the next step without any further purification.

67: $C_{14}H_{14}O$ M=198.26 g·mol$^{-1}$

Rf: 0.23 (dichloromethane).

Mass (CI+): 181 (M−H$_2$O+H).

Synthesis of Compound 68

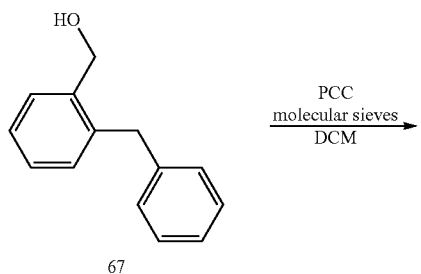

Pyridinium chlorochromate (PCC) (4.56 g, 21 mmol, 1.4 eq.) is added to a round-bottom flask under inert atmosphere, which contains 67 (3.00 g, 15.0 mmol, 1 eq.) in dry dichloromethane (150 mL) and molecular sieves. The mixture is stirred overnight at ambient temperature and filtered through celite (dichloromethane eluent). Solvent is removed and the residue is purified on a chromatography column (90/10 cyclohexane/ethyl acetate eluent) in order to produce compound 68 in the form of a white solid, with a yield of 67%.

68: $C_{14}H_{12}O$ M=196.24 g·mol$^{-1}$

Rf: 0.87 (cyclohexane/ethyl acetate 7/3).

Mass (ESI+): 213.92 (M+H$_2$O).

Synthesis of Compound 69

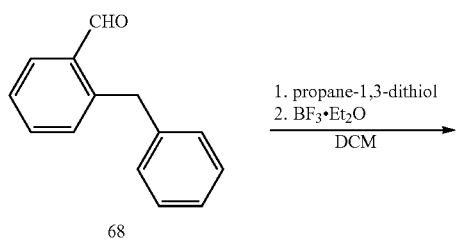

Propane-1,3-dithiol (1.50 mL, 15.12 mmol, 1.5 eq.) is added in a round-bottom flask under an inert atmosphere which contains a solution of compound 68 (1.48 g, 10.1 mmol, 1 eq.) in dichloromethane (30 mL) at 0° C. Boron trifluoride etherate (0.25 mL, 1.98 mmol, 0.2 eq.) is added dropwise at this temperature. The mixture is stirred at 0° C. for 15 min and overnight at room temperature. The reaction medium is extracted with dichloromethane, washed with a 5% sodium hydroxide aqueous solution, water and dried over magnesium sulphate prior to being concentrated. The residue is recristallized from acetonitrile to produce compound 69 in the form of a white solid, with a yield of 81%.

69: $C_{17}H_{18}S_2$ M=286.45 g·mol$^{-1}$

Rf: 0.55 (cyclohexane/ethyl acetate 9/1).

Mass (ESI+): 287 (M+H).

Synthesis of Compound 70

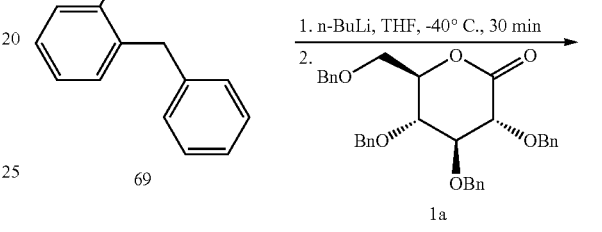

Compound 70 is prepared according to the procedure previously described (synthesis of compound 57) from compound 69 (2.23 g, 2.78 mmol, 2.1 eq.), 1.5M solution of n-butyllithium in hexane (5.4 mL, 8.15 mmol, 2.2 eq.) and lactone 1a (1.99 g, 3.70 mmol, 1 eq.) to give a white solid.

70: $C_{51}H_{52}O_6S_2$ M=825.08 g·mol$^{-1}$

Rf: 0.51 (cyclohexane/ethyl acetate 75/25).

Mass (ESI+): 842.27 (M+H$_2$O).

Synthesis of Compound 71

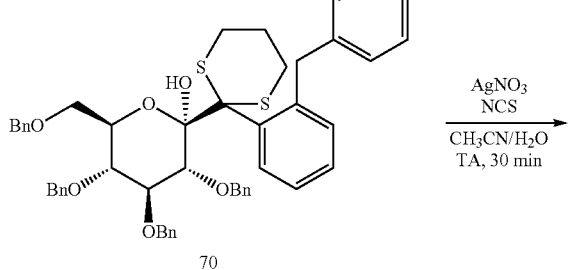

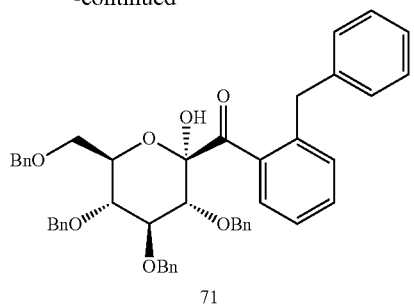

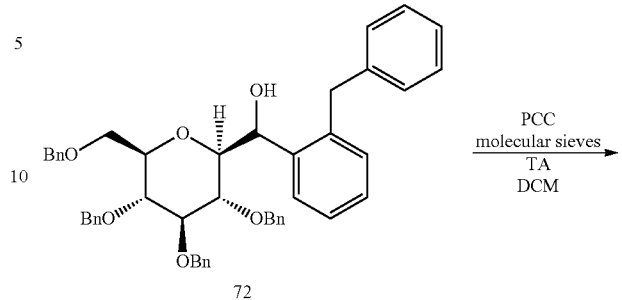

A solution of 70 (1.21 g, 1.57 mmol; 1 eq.) in acetonitrile (3 mL) is quickly added to a round-bottom flask which contains N-chlorosuccinimide (0.84 g, 6.28 mmol; 4 eq.) and silver nitrate (1.12 g, 6.60 mmol, 4.5 eq.) in a mixture of acetonitrile and water in proportions of 8:2 (30 mL) at room temperature. The mixture is vigorously stirred for 30 min. Saturated sodium sulfite aqueous solution (2 mL), saturated sodium carbonate aqueous solution (2 mL), brine (2 mL) and cyclohexane (80 mL) are successively added to the reaction mixture. The reaction medium is filtered through celite, dried over magnesium sulfate prior to being concentrated The residue is then purified on chromatography column (100/0 to 60/40 cylohexane/ethyl acetate eluent) to produce 71 in the form of a white solid with a yield of 47%.

71: $C_{48}H_{46}O_7$ M=734.87 g·mol$^{-1}$
Rf: 0.49 (cyclohexane/ethyl acetate 8/2).
Mass (ESI+): 752.27 (M+H$_2$O); 1486.00 (2M+H$_2$O).

Synthesis of Compound 72

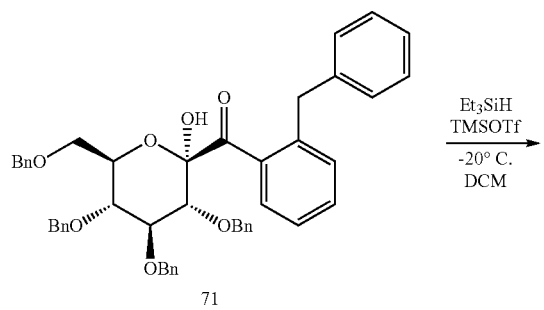

Compound 72 is prepared according to the procedure previously described (synthesis of compound 59) from triethylsilane (0.088 mL; 0.54 mmol, 4 eq.) and trimethylsilyl trifluoromethanesulfonate (0.025 mL, 0.14 mmol, 1 eq.) in the form of a white solid, with a yield of 18%.

72: $C_{48}H_{48}O_6$ M=720.89 g·mol$^{-1}$
Rf: 0.24 (cyclohexane/ethyl acetate 85/15).
Mass (ESI+): 738.20 (M+H$_2$O); 1457.67 (2M+H$_2$O).

Synthesis of Compound 73

Compound 73 is prepared according to the procedure previously described (synthesis of compound 62) at temperature ambient (TA) from compound 72 (0.016 g, 0.02 mmol) and pyridinium chlorochromate (0.01 mg, 0.05 mmol, 2 eq.) to give a white solid, with a yield of 55%.

73: $C_{48}H_{46}O_6$ M=718.88 g·mol$^{-1}$
Rf: 0.35 (cyclohexane/ethyl acetate 8/2).
Mass (ESI+): 736.27 (M+H$_2$O).

Synthesis of Compound 74

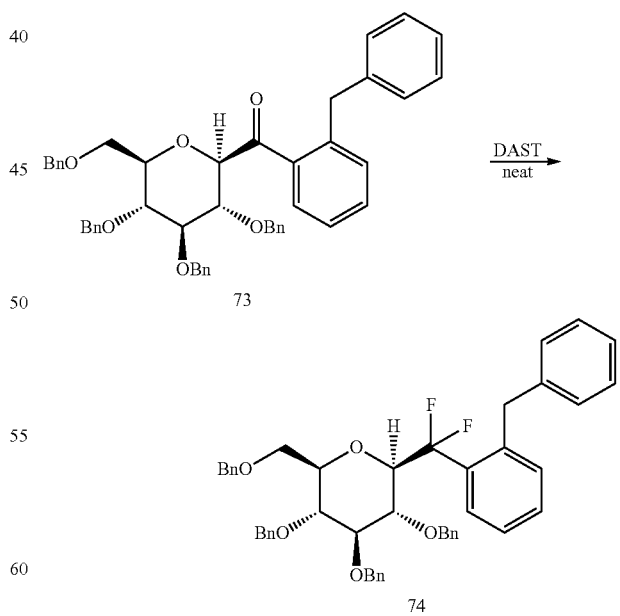

Compound 73 is fluorinated 3 times with diethylaminosulfur trifluoride (0.3 mL) neat by stirring overnight at 70° C. in a round-bottom flask under an inert atmosphere according to the procedure previously described (synthesis of compound 63). Between each time, the residue needs to be purified on a chromatography column (80/20 cyclohexane/ethyl acetate eluent) to remove diethylaminosulfur trifluoride residues before being reintroduced in a fluorination reaction. The residue is purified on preparative HPLC (Kromasil 100-5C18, 15 cm*21.2 mm id, 100% acetonitrile, 254 nm).

74: $C_{48}H_{46}F_2O_5$ M=740.87 g·mol$^{-1}$

Rf: 0.5 (cyclohexane/ethyl acetate 8/2).

NMR $^{19}$F (CDCl$_3$, 282.5 MHz): −95.3 (d, J=259 Hz, 1F); −105.2 (dd, J1=19 Hz, J2=259 Hz, 1F).

Synthesis of Compound 76

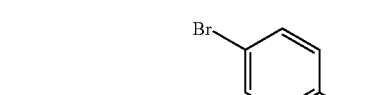

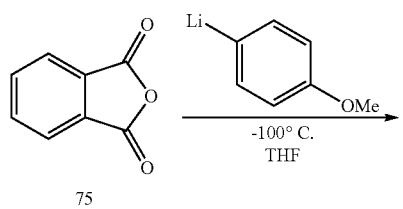

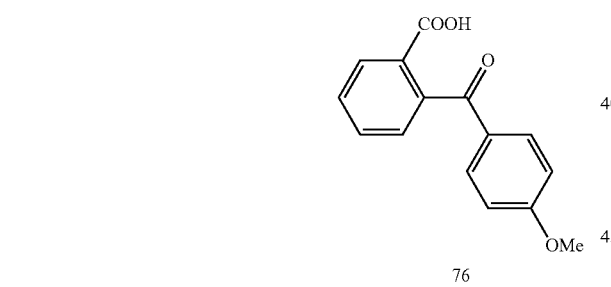

A 2.5 M solution of n-butyllithium in hexane (13.5 mL, 33.8 mmol, 1 eq.) is added dropwise to a round-bottom flask under an inert atmosphere which contains 1-Bromo-4-methoxy-benzene (4.7 mL, 37.1 mmol, 1.1 eq.) in dry tetrahydrofuran (100 mL) at −78° C. The mixture is stirred at this temperature for 1 h before being quickly added to a solution of 75 (10.0 g, 67.5 mmol, 2 eq.) in tetrahydrofuran (10 mL) at −100° C. The mixture is stirred 1 h at this temperature and 2 h at ambient temperature. The mixture is concentrated and then diluted in diethyl ether. Water and then a 1N hydrochloric acid aqueous solution are added. The organic layer is washed with a saturated sodium carbonate solution and the aqueous layer is acidified with concentrated hydrochloric acid. The precipitate is filtered and dried to produce compound 76 in the form of a white solid with a yield of 35%.

76: $C_{15}H_{12}O_4$ M=256.25 g·mol$^{-1}$

Rf: 0.27 (cyclohexane/ethyl acetate 3/7).

Mass (ESI+): 257.03 (M+H); 273.80 (M+H$_2$O).

Synthesis of Compound 77

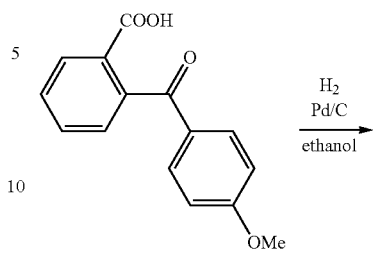

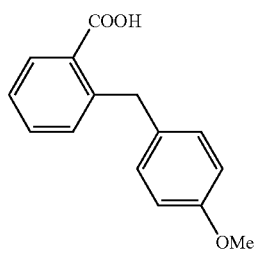

Compound 76 (2.98 g, 11.63 mmol, 1 eq.) is placed inside a round-bottom flask and dissolved in ethanol (115 mL) in the presence of a spatula tip of Pd/C under a hydrogen atmosphere. The mixture is stirred for 6 days, then Millipore-filtered and evaporated to produce compound 77 in the form of a white powder with a yield of 97%.

77: $C_{15}H_{14}O_3$ M=242.27 g·mol$^{-1}$

Rf: 0.3 (cyclohexane/ethyl acetate 3/7).

Mass (ESI−): 241.38 (M−H); 482.94 (2M−H).

Synthesis of Compound 78

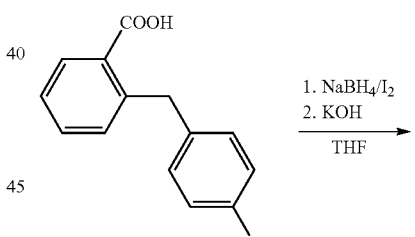

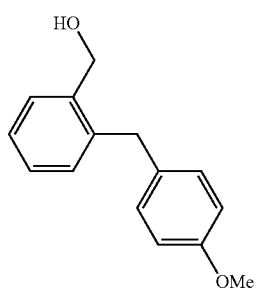

Compound 78 was prepared according to the procedure previously described (synthesis of compound 67) from compound 77 (13.83 g, 57.1 mmol, 1 eq.) sodium borohydride (5.20 g, 137.0 mmol, 2.4 eq.) and iodine (14.5 g, 57.1 mmol, 1 eq.) in the form of a yellow oil with a quantitative yield.

78: $C_{15}H_{16}O_2$ M=228.29 g·mol$^{-1}$
Rf: 0.28 (cyclohexane/ethyl acetate 7/3).
Mass (CI+): 228 (M)

Synthesis of Compound 79

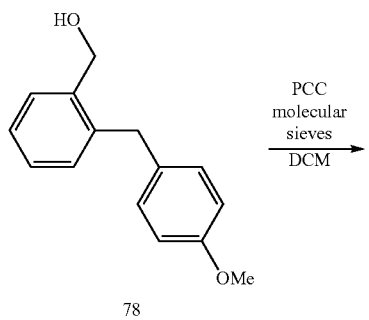

Compound 79 was prepared according to the procedure previously described (synthesis of compound 68) from compound 78 (13.0 g, 56.9 mmol, 1 eq.) and pyridinium chlorochromate (17.2 g, 79.7 mmol, 1.4 eq.) to give a yellow oil with a yield of 81%.

79: $C_{15}H_{14}O_2$ M=226.27 g·mol$^{-1}$
Rf: 0.14 (cyclohexane/ethyl acetate 95/5).
Mass (CI+): 227 (M+H).

Synthesis of Compound 80

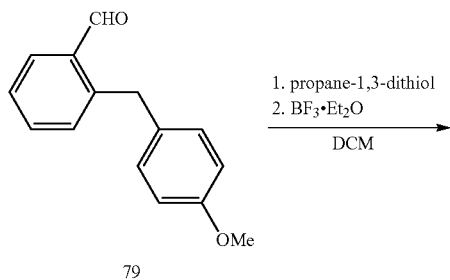

Compound 80 was prepared according to the procedure previously described (synthesis of compound 69) from compound 79 (1.76 g, 7.78 mmol, 1 eq.), propane-1,3-dithiol (1.20 mL, 11.7 mmol, 1.5 eq.) and boron trifluoride etherate (0.20 mL, 1.56 mmol, 0.2 eq.) to give a white solid with a yield of 94%.

80: $C_{18}H_{20}OS_2$ M=316.48 g·mol$^{-1}$
Rf: 0.55 (cyclohexane/ethyl acetate 9/1).
Mass (CI+): 317 (M+H).

Synthesis of Compound 81

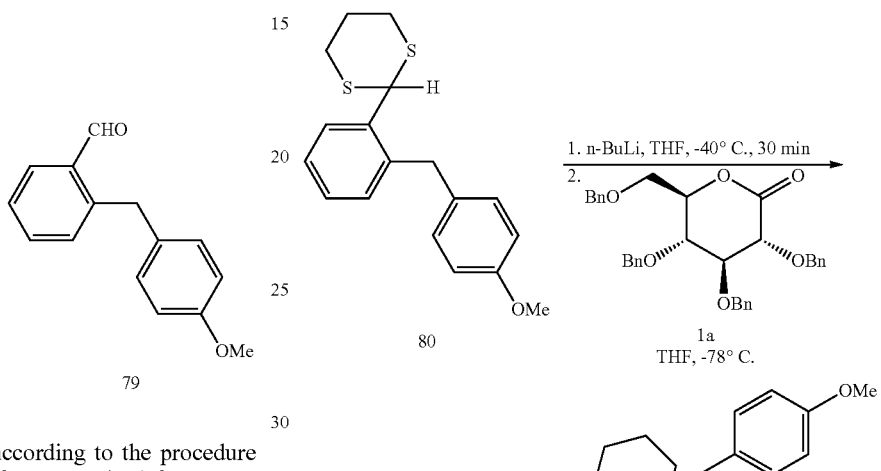

Compound 81 is prepared according to the procedure previously described (synthesis of compound 57) from compound 80 (2.19 g, 6.91 mmol, 2.1 eq.), 1.4M solution of n-butyllithium in hexane (5.17 mL, 7.24 mmol, 2.2 eq) and lactone 1a (1.77 g, 3.29 mmol, 1 eq.) to give a white solid.

81: $C_{52}H_{54}O_7S_2$ M=855.11 g·mol$^{-1}$
Rf: 0.22 (cyclohexane/ethyl acetate 8/2).
Mass (ESI+): 872.20 (M+H$_2$O)

Synthesis of Compound 82

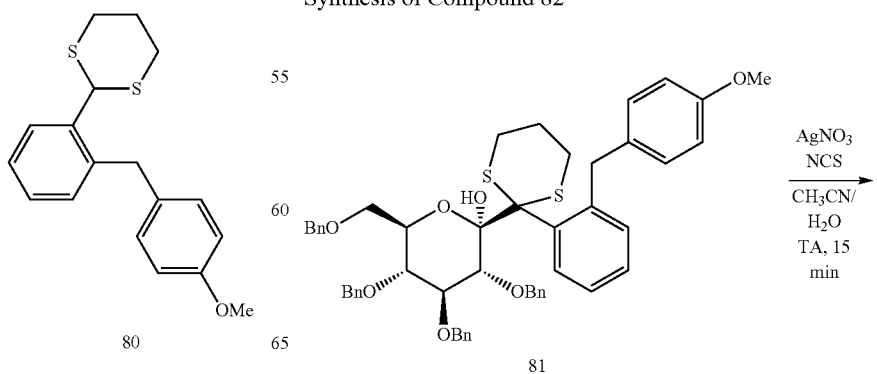

83

-continued

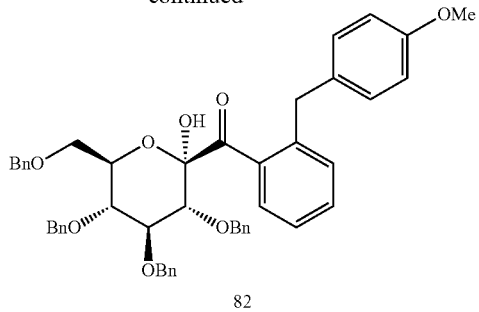

82

Compound 82 is prepared according to the procedure previously described (synthesis of compound 71) from compound 81 (1.29 g, 1.50 mmol, 1 eq.), N-chlorosuccinimide (0.80 g, 6.00 mmol; 4 eq.) and silver nitrate (1.15 g, 6.76 mmol, 4.5 eq.) to give a white solid with a yield of 56%.

82: $C_{49}H_{48}O_8$ M=764.90 g·mol$^{-1}$

Rf: 0.46 (cyclohexane/ethyl acetate 75/25).

Mass (ESI+): 782.20 (M+H); 1546.13 (M+H$_2$O).

Synthesis of Compound 83

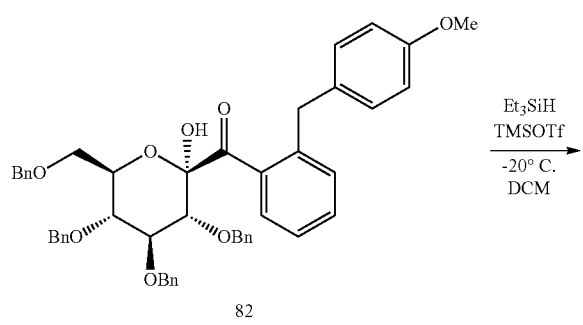

82

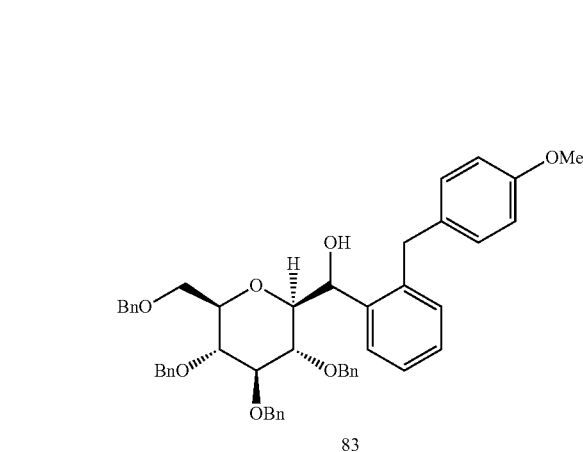

83

Compound 83 is prepared according to the procedure previously described (synthesis of compound 59) from triethylsilane (0.087 mL; 0.54 mmol, 4 eq.) and trimethylsilyl trifluoromethanesulfonate (0.025 mL, 0.14 mmol, 1 eq.) in the form of a white solid, with a yield of 17%.

83: $C_{49}H_{50}O_7$ M=750.92 g·mol$^{-1}$

Rf: 0.25 (cyclohexane/ethyl acetate 8/2).

Mass (ESI+): 768.27 (M+H$_2$O); 1518.20 (2M+H$_2$O).

84

Synthesis of Compound 84

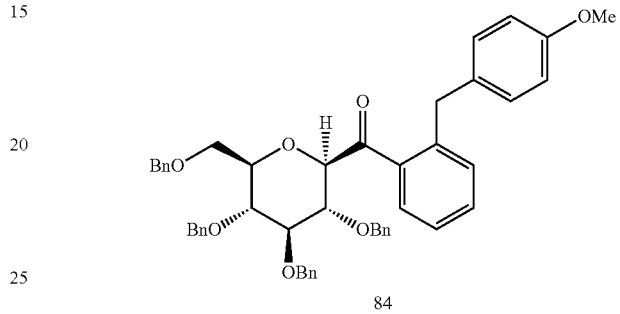

83

84

Compound 84 is prepared according to the procedure previously described (synthesis of compound 62) from compound 83 (0.015 g, 0.02 mmol) and pyridinium chlorochromate (0.008 mg, 0.04 mmol, 2 eq) to give a white solid, with a yield of 56%.

84: $C_{49}H_{48}O_7$ M=748.90 g·mol$^{-1}$

Rf: 0.43 (cyclohexane/ethyl acetate 8/2).

Mass (ESI+): 766.20 (M+H$_2$O); 1514.73 (2M+H$_2$O).

Synthesis of Compound 85

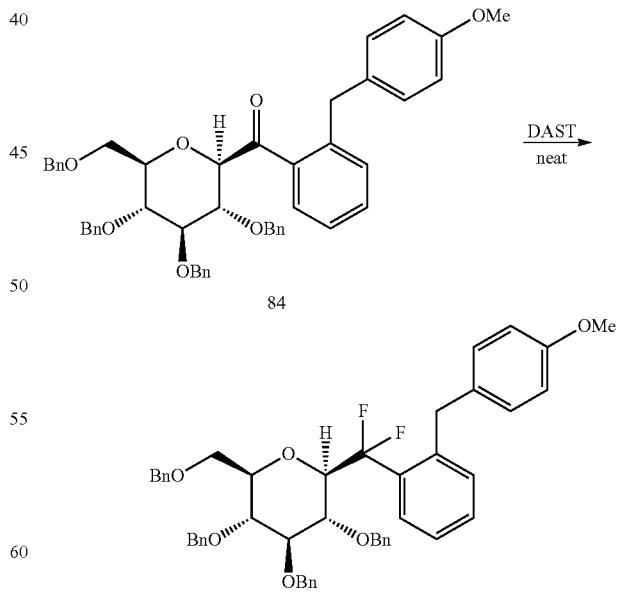

84

85

Compound 84 is fluorinated 3 times with diethylaminosulfur trifluoride (0.3 mL) neat by stirring overnight at 70° C. in a round-bottom flask under an inert atmosphere according to the procedure previously described (synthesis of compound 63). Between each time, the residue needs to be purified on a chromatography column (80/20 cyclohexane/ethyl acetate eluent) to remove diethylaminosulfur trifluoride residues before being reintroduced in a fluorination reaction. The residue is purified on preparative HPLC (Kromasil 100-5C18, 15 cm*21.2 mm id, 100% acetonitrile, 254 nm).

85: $C_{49}H_{48}F_2O_6$ M=770.90 g·mol$^{-1}$
Rf: 0.48 (cyclohexane/ethyl acetate 8/2).
NMR $^{19}$F (CDCl$_3$, 282.5 MHz): −95.2 (d, J=259 Hz, 1F); −105.2 (dd, J1=19 Hz, J2=258 Hz).

Synthesis of Compound 86

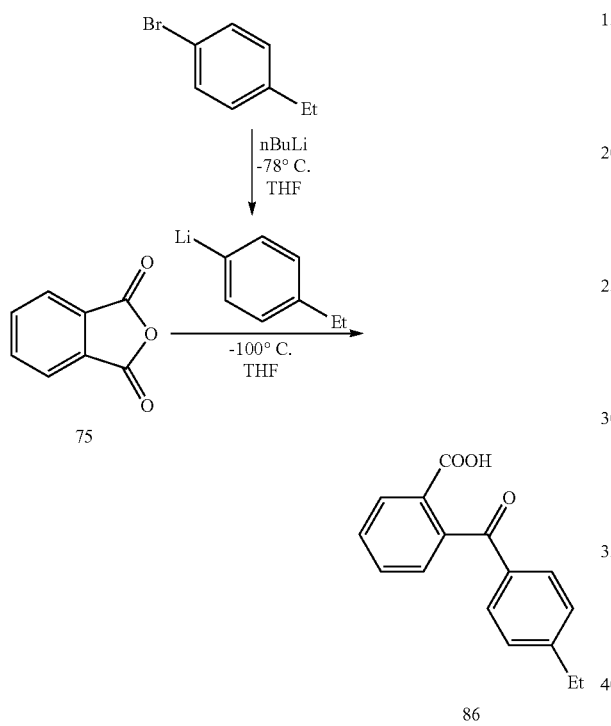

Compound 86 was prepared according to the procedure previously described (synthesis of compound 76) from compound 75 (10.0 g, 67.5 mmol, 2 eq.), 2.5M solution of n-butyllithium in hexane (13.5 mL, 33.8 mmol, 1 eq.) and 1-Bromo-4-ethyl-benzene (5.1 mL, 37.1 mmol, 1.1 eq.) to give a white solid with a yield of 40%.

86: $C_{16}H_{14}O_3$ M=254.28 g·mol$^{-1}$
Rf: 0.24 (cyclohexane/ethyl acetate 5/5).
Mass (ESI+): 255.10 (M+H); 271.93 (M+H$_2$O).

Synthesis of Compound 87

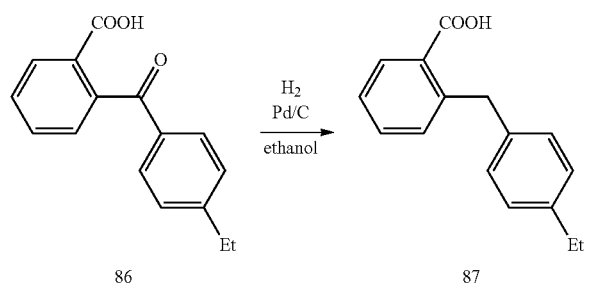 [SMILES: CCc1ccc(C(=O)c2ccccc2C(=O)O)cc1 ; CCc1ccc(Cc2ccccc2C(=O)O)cc1]

Compound 86 was deprotected according to the procedure previously described (synthesis of compound 77) in 48 h, to give a white solid with a quantitative yield.

87: $C_{16}H_{16}O_2$ M=240.30 g·mol$^{-1}$
Rf: 0.61 (cyclohexane/ethyl acetate 5/5).
Mass (ESI−): 239.27 (M−H).

Synthesis of Compound 88

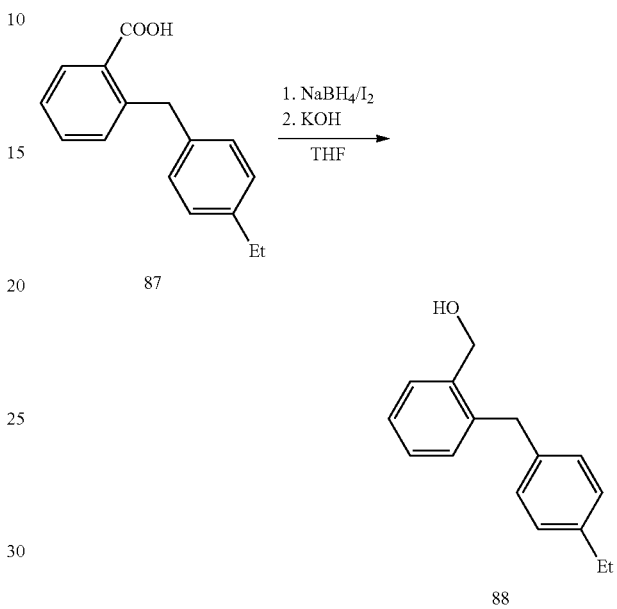

Compound 88 was prepared according to the procedure previously described (synthesis of compound 67) from compound 87 (22.7 g, 36.0 mmol, 1 eq.), sodium borohydride (8.51 g, 225 mmol, 2.4 eq.) and iodine (23.8 g, 93.6 mmol, 1 eq.) to give a colourless oil with a quantitative yield.

88: $C_{16}H_{18}O$ M=226.31 g·mol$^{-1}$
Rf: 0.53 (cyclohexane/ethyl acetate 7/3).
Mass (ESI+): 243.99 (M+H$_2$O).

Synthesis of Compound 89

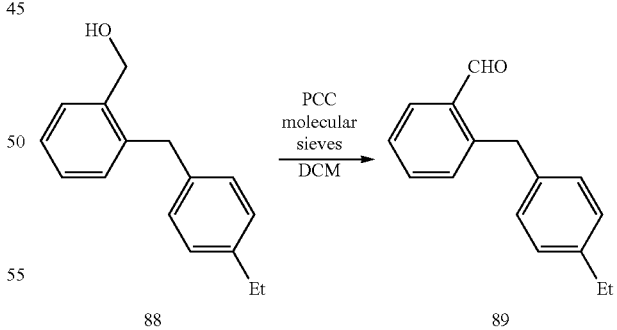

Compound 89 was prepared according to the procedure previously described (synthesis of compound 68) from compound 88 (21.2 g, 93.6 mmol, 1 eq.) and pyridinium chlorochromate (28.25 g, 131.0 mmol, 1.4 eq.) to give a yellow oil with a yield of 81%.

89: $C_{16}H_{16}O$ M=224.30 g·mol$^{-1}$
Rf: 0.39 (cyclohexane/ethyl acetate 95/5).
Mass (CI+): 225 (M+H).

Synthesis of Compound 90

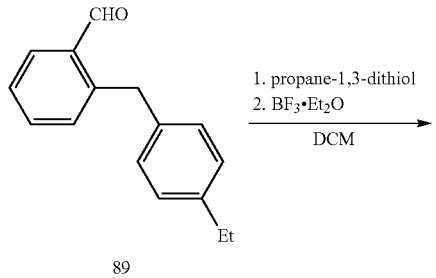

89

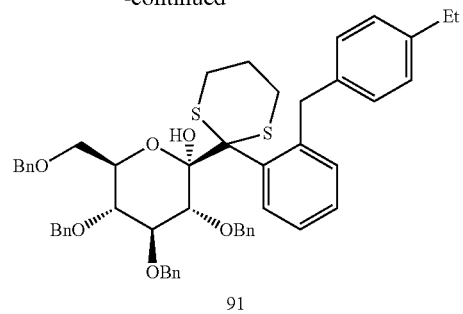

91

Compound 91 is prepared according to the procedure previously described (synthesis of compound 57) from compound 90 (2.79 g, 8.87 mmol, 4.4 eq.), 1.4M solution of n-butyllithium in hexane (6.4 mL, 9.09 mmol, 4.5 eq) and lactone 1a (1.09 g, 2.02 mmol, 1 eq.) in the form of a yellow oil.

91: $C_{53}H_{56}O_6S_2$ M=853.14 g·mol$^{-1}$

Rf: 027 (cyclohexane/ethyl acetate 8/2).

Mass (ESI+): 870.07 (M+H$_2$O).

Synthesis of Compound 92

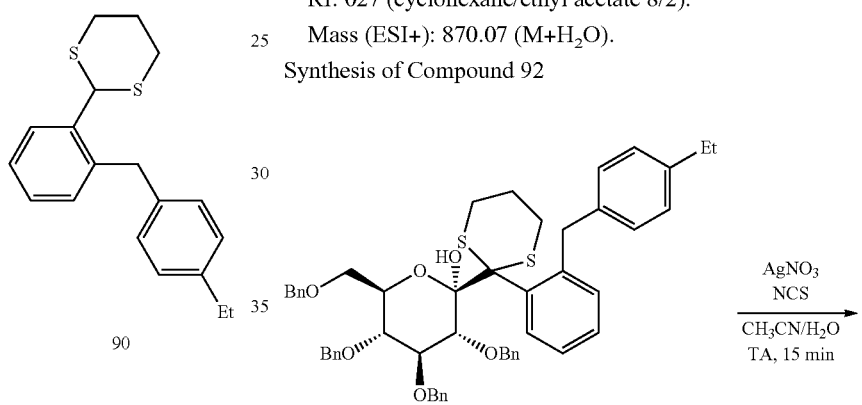

91

90

Compound 90 was prepared according to the procedure previously described (synthesis of compound 69) from compound 89 (2.39 g, 10.7 mmol, 1 eq.), propane-1,3-dithiol (1.6 mL, 15.5 mmol, 1.5 eq.) and boron trifluoride etherate (0.27 mL, 2.13 mmol, 0.2 eq.) in the form of a white solid with a yield of 82%.

90: $C_{19}H_{22}S_2$ M=314.51 g·mol$^{-1}$

Rf: 0.63 (cyclohexane/ethyl acetate 9/1).

Mass (ESI+): 315 (M+H).

Synthesis of Compound 91

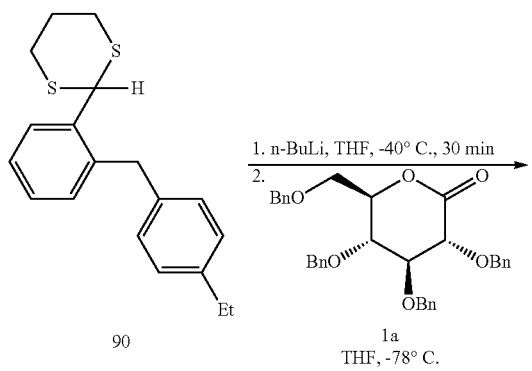

92

Compound 92 is prepared according to the procedure previously described (synthesis of compound 71) from compound 91 (0.67 g, 0.79 mmol, 1 eq.), N-chlorosuccinimide (0.42 g, 3.14 mmol; 4 eq.) and silver nitrate (0.60 g, 3.53 mmol, 4.5 eq.) to give a white solid with a yield of 48%.

92: $C_{50}H_{50}F_2O_7$ M=762.93 g·mol$^{-1}$

Rf: 0.48 (cyclohexane/ethyl acetate 8/2).

Synthesis of Compound 93

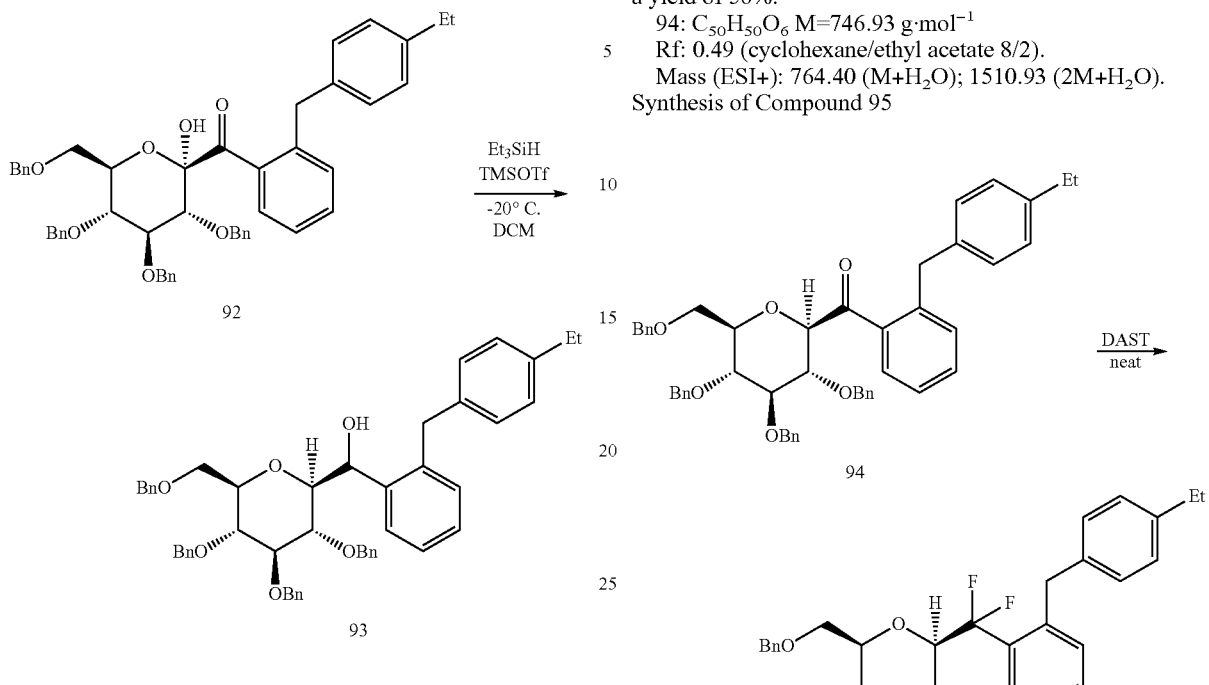

Compound 93 is prepared according to the procedure previously described (synthesis of compound 59) from triethylsilane (0.238 mL; 1.47 mmol, 4 eq.) and trimethylsilyl trifluoromethanesulfonate (0.067 mL, 0.37 mmol, 1 eq.) to give a white solid, with a yield of 19%.

93: $C_{50}H_{52}O_6$ M=748.94 g·mol$^{-1}$
Rf: 0.30 (cyclohexane/ethyl acetate 8/2).
Mass (ESI+): 766.20 (M+H$_2$O); 1514.93 (2M+H$_2$O)

Synthesis of Compound 94

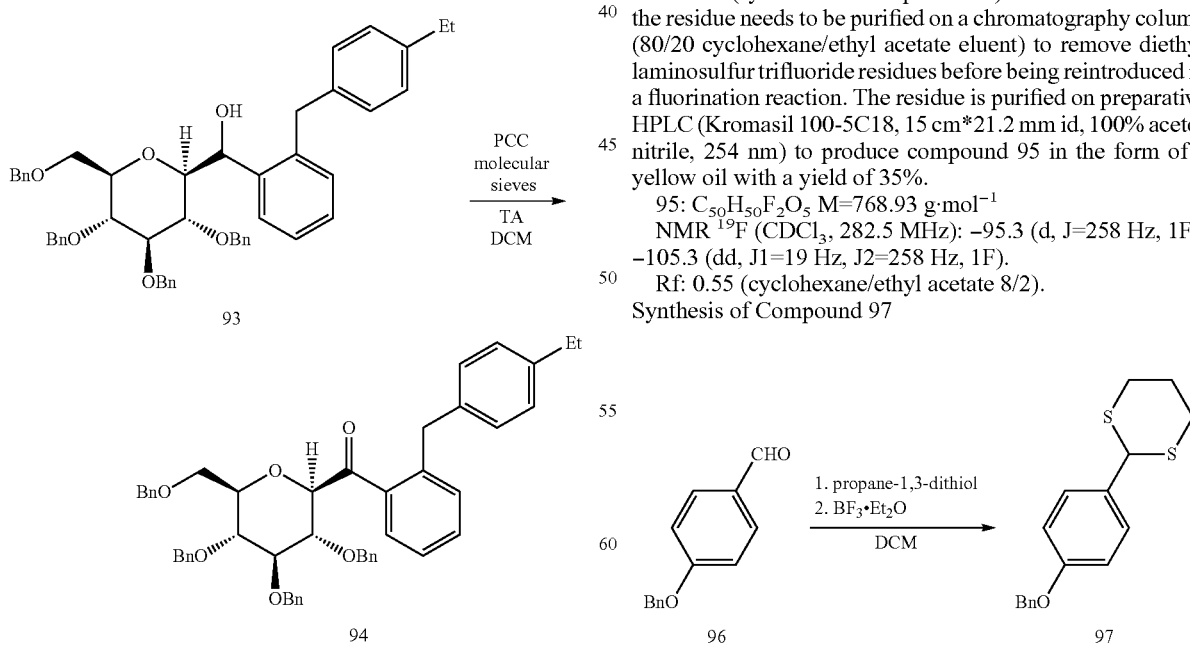

Compound 94 is prepared according to the procedure previously described (synthesis of compound 62) from compound 93 (0.052 g, 0.07 mmol) and pyridinium chlorochromate (0.030 mg, 0.14 mmol, 2 eq.) to give a white solid, with a yield of 56%.

94: $C_{50}H_{50}O_6$ M=746.93 g·mol$^{-1}$
Rf: 0.49 (cyclohexane/ethyl acetate 8/2).
Mass (ESI+): 764.40 (M+H$_2$O); 1510.93 (2M+H$_2$O).

Synthesis of Compound 95

Compound 94 (0.033 g, 0.04 mmol, 1 eq.) is fluorinated 3 times with diethylaminosulfur trifluoride (0.300 mL) neat by stirring overnight at 70° C. in a round-bottom flask under an inert atmosphere according to the procedure previously described (synthesis of compound 63). Between each time, the residue needs to be purified on a chromatography column (80/20 cyclohexane/ethyl acetate eluent) to remove diethylaminosulfur trifluoride residues before being reintroduced in a fluorination reaction. The residue is purified on preparative HPLC (Kromasil 100-5C18, 15 cm*21.2 mm id, 100% acetonitrile, 254 nm) to produce compound 95 in the form of a yellow oil with a yield of 35%.

95: $C_{50}H_{50}F_2O_5$ M=768.93 g·mol$^{-1}$
NMR $^{19}$F (CDCl$_3$, 282.5 MHz): −95.3 (d, J=258 Hz, 1F); −105.3 (dd, J1=19 Hz, J2=258 Hz, 1F).
Rf: 0.55 (cyclohexane/ethyl acetate 8/2).

Synthesis of Compound 97

Compound 97 is prepared according to the procedure previously described (synthesis of compound 69) from compound 96 (10 g, 47.1 mmol, 1 eq.), 1,3-propanedithiol (7.15 mL; 70.7 mmol; 1.5 eq.) and boron trifluoride etherate (0.70 mL; 5.54 mmol; 0.1 eq.) to give white crystals with a yield of 89%.

97: $C_{17}H_{18}OS_2$ M=302.45 g·mol$^{-1}$

Mass (EI): 302 (M)

Synthesis of Compound 98

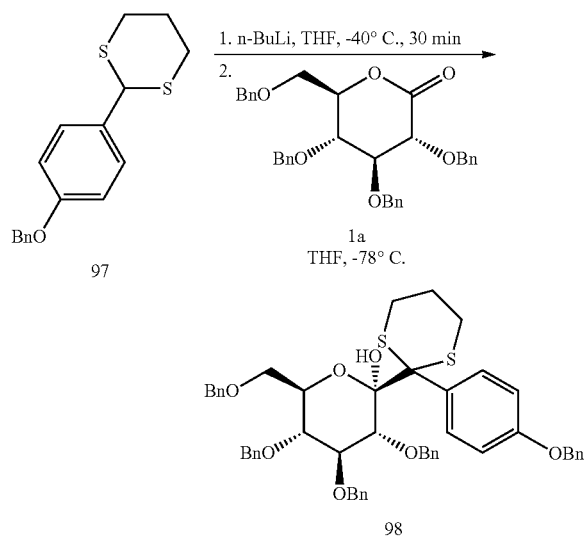

Compound 98 is prepared according to the procedure previously described (synthesis of compound 57) from compound 97 (3.54 g, 11.7 mmol, 2.1 eq.), 2.5M solution of n-Butyllithium in hexane (4.8 mL, 12.0 mmol, 2.2 eq.) and lactone 1a (3.00 g, 5.57 mmol, 1 eq.) to give a white solid with a yield of 59%.

98: $C_{51}H_{52}O_7S_2$ M=841.08 g·mol$^{-1}$

Rf: 0.33 (cyclohexane/ethyl acetate 8/2).

Mass (ESI+): 858.07 (M+H$_2$O)

Synthesis of Compound 99

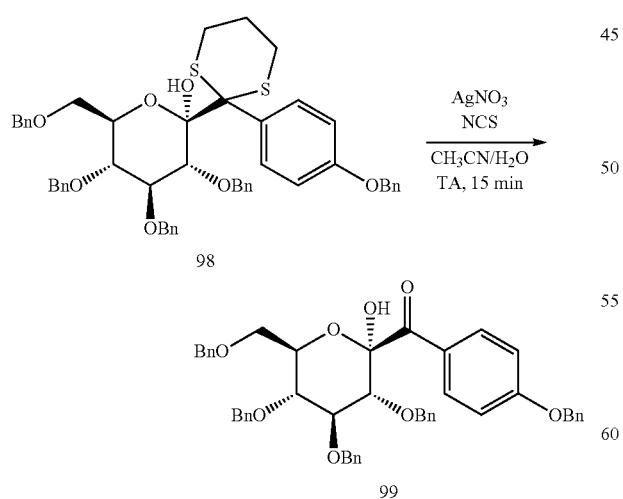

Compound 99 is prepared according to the procedure previously described (synthesis of compound 71) from compound 98 (4.00 g, 4.76 mmol, 1 eq.), N-chlorosuccinimide (2.66 g, 19.0 mmol, 4 eq.) and silver nitrate (3.64 g, 21.0 mmol, 4.5 eq.) to give a colourless oil which slowly crystallizes with a yield of 84%.

99: $C_{48}H_{46}O_8$ M=750.87 g·mol$^{-1}$

Rf: 0.32 (cyclohexane/ethyl acetate 8/2).

Mass (ESI+): 768.13 (M+H$_2$O).

Synthesis of Compound 100

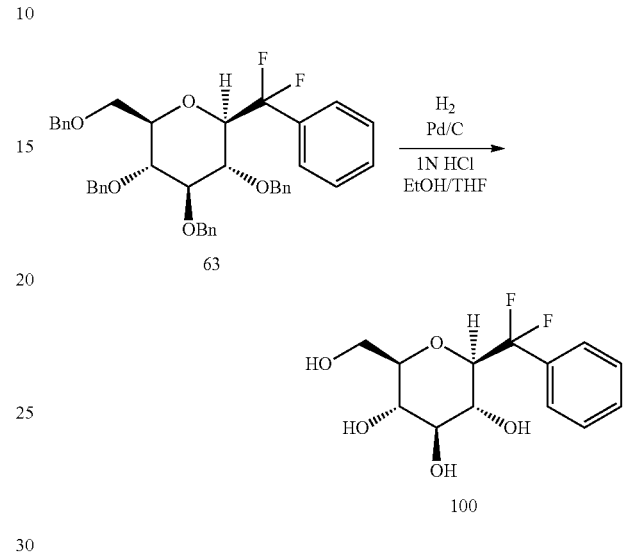

Compound 63 (19.3 mg, 0.03 mmol, 1 eq.) is deprotected according to the procedure described previously (synthesis of 51) to afford compound 100 in the form of a white solid, with a 87% yield.

100: $C_{13}H_{16}F_2O_5$ M=290.26 g·mol$^{-1}$

NMR $^{19}$F (MeOD, 282.5 MHz): −98.4 (dd, J1=260 Hz, J2=6 Hz, 1F); −107.2 (dd, J1=261 Hz, J2=11 Hz, 1F).

Mass (ESI−): 325.0 (M+Cl).

Synthesis of Compound 101d1/101d2

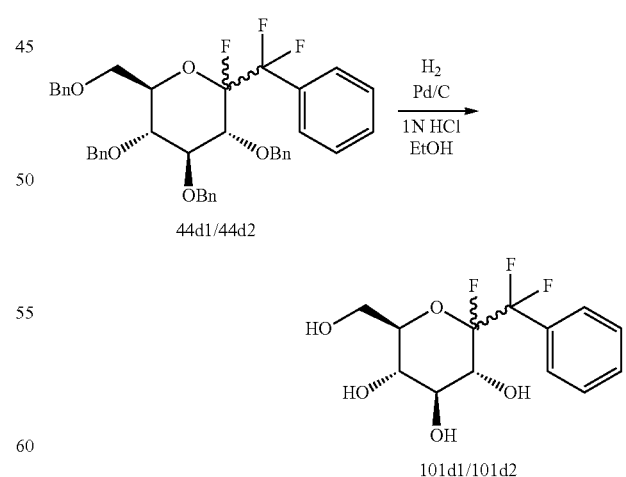

Compound 44d1 (40.6 mg, 60.8 mmol, 1 eq.) is deprotected according to the procedure described previously (synthesis of 51) to afford compound 101d1 in the form of a white solid, with a quantitative yield.

Compound 44d2 (47.2 mg, 70.6 mmol, 1 eq.) is deprotected according to the procedure described previously (synthesis of 51) to afford compound 101d2 in the form of a white solid, with a quantitative yield.

101d1/101d2: $C_{13}H_{15}F_3O_5$ M=308.25 g·mol$^{-1}$

NMR $^{19}$F (D$_2$O, 282.5 MHz):

101d1: −108.4 (dd, J1=5 Hz, J2=259 Hz, 1F); −109.4 (d, J=259 Hz, 1F); −142.9 (dd, J1=5 Hz, J2=23 Hz, 1F).

101d2: −102.0 (dd, J1=8 Hz, J2=264 Hz, 1F); −107.2 (dd, J1=9 Hz, J2=264 Hz, 1F); −113.0 (brd, J=9 Hz, 1F).

Mass (ESI+): 326.07 (M+H$_2$O); 331.13 (M+Na) 101d1.

326.07 (M+H$_2$O); 331.03 (M+Na) 101d2.

Synthesis of Compound 102

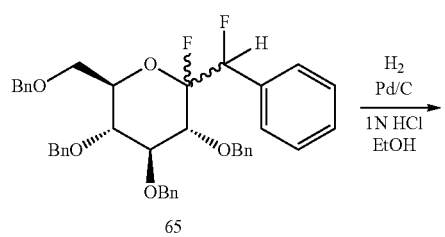

65

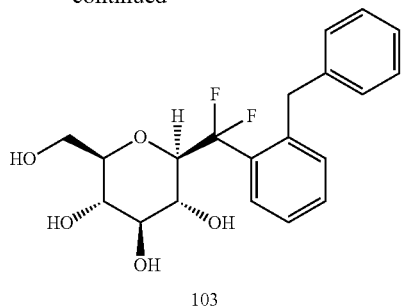

102

Compound 65 (36.4 mg, 0.06 mmol, 1 eq.) is deprotected according to the procedure described previously (synthesis of 51) to afford compound 102 in the form of a yellow oil, with a quantitative yield.

102: $C_{13}H_{16}F_2O_5$ M=290.26 g·mol$^{-1}$

Mass (ESI−): 287.0-289.0-291.0 (M−H); 323.0-325.0-327.0 (M+Cl).

Synthesis of Compound 103

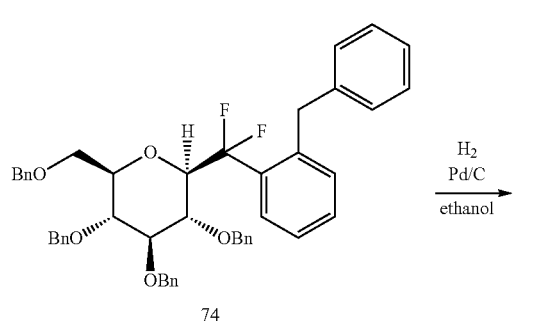

74

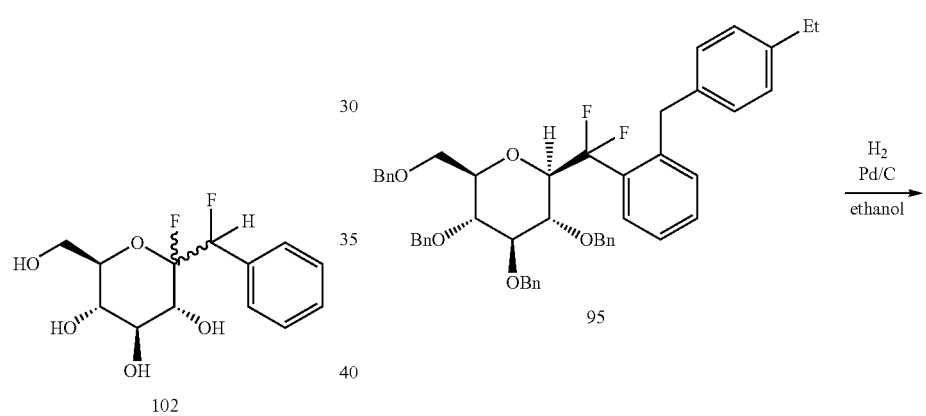

Compound 74 (5.70 mg, 0.008 mmol, 1 eq.) is deprotected according to the procedure described previously (synthesis of 47A-47-B, first process) to afford compound 103 in the form of a colourless oil with a yield of 50%.

103: $C_{20}H_{22}F_2O_5$ M=380.38 g·mol$^{-1}$

NMR $^{19}$F (MeOD, 282.5 MHz): −95.6 (dd, J1=5 Hz, J2=262 Hz, 1F); −104.5 (dd, J1=14 Hz, J2=263 Hz, 1F).

Mass (ESI−): 379.0 (M−H); 415.1 (M+Cl).

Synthesis of Compound 104

Compound 95 (0.011 mg, 0.01 mmol, 1 eq.) is deprotected according to the procedure described previously (synthesis of 47A-47-B, first process) to afford compound 104 in the form of a colourless oil with a yield of 30%.

105: $C_{22}H_{26}F_2O_5$ M=408.44 g·mol$^{-1}$

NMR $^{19}$F (MeOD, 282.5 MHz): −95.6 (d, J=262 Hz, 1F); −104.8 (dd, J1=14 Hz, J2=262 Hz, 1F).

Mass (ESI−): 407.1 (M−H); 443.1 (M+Cl).

Synthesis of Compound 105

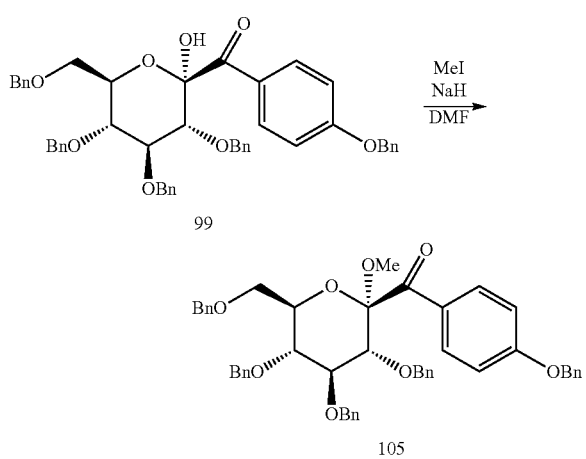

Methyliodide (0.028 mL; 0.45 mmol; 1.5 eq.) is added to a solution of compound 99 (225 mg; 0.30 mmol; 1 eq.) in dimethylformamide (DMF) (2 mL). NaH 95% (38.0 mg; 1.50 mmol; 5 eq.) is added in one portion, and the media is stirred at room temperature during 30 minutes. A solution of chlorhydric acid 1M is then slowly added. Ethylacetate is then added and the organic phase is washed three times with water, then with brine. The organic layer is dried on MgSO$_4$, filtered and then concentrated. The residue is then purified on chromatography column (98/2 to 80/20 cylohexane/ethyl acetate eluent) to produce 105 in the form of a colourless oil with a yield of 89%.

105: $C_{49}H_{48}O_8$ M=764.90 g·mol$^{-1}$
Mass (ESI+): 787.40 (M+Na); 1552.00 (2M+Na)

Synthesis of Compound 106

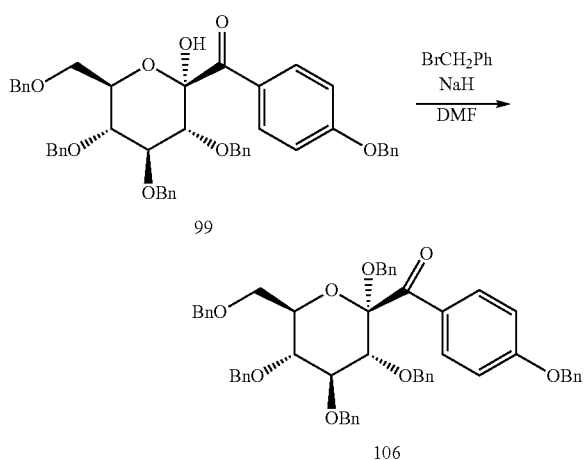

Benzyl bromide (0.054 mL; 0.45 mmol; 1.5 eq.) is added to a solution of compound 99 (228 mg; 0.30 mmol; 1 eq.) in DMF (2 mL). NaH 95% (36.4 mg; 1.52 mmol; 5 eq.) is added in one portion, and the media is stirred at room temperature during 10 minutes. A solution of chlorhydric acid 1M is then slowly added. Ethylacetate is then added and the organic phase is washed three times with water, then with brine. The organic layer is dried on MgSO$_4$, filtered and then concentrated. The residue is then purified on chromatography column (98/2 to 80/20 cylohexane/ethyl acetate eluent) to produce 106 in the form of a colorless oil.

106: $C_{55}H_{52}O_8$ M=841.00 g·mol$^{-1}$
Mass (ESI+): 863.40 (M+Na); 1703.27 (2M+Na)

2. Biological Activity

The compounds of the invention have been tested for their ability to inhibit Human Sodium Glucose Co-Transporter 2 (Human SGLT2) according to the following protocol:

1. Preparation of Human SGLT1 and Human SGLT2 Expression Vectors:

Human SGLT1 (Genbank M24847) cDNA was cloned from a pCMV6 vector containing the full length human SGLT1 gene (Origene NM 000343, Cat. #: RC221312) and Human SGLT2 (Genbank M95549) cDNA was cloned from a pCMV6 vector containing the full length human SGLT2 gene (Origene NM_003041, Cat. #: RC224822). The full cDNAs were subcloned independently into mammalian cell expression plasmid pSPI1 and sequenced to verify the integrity of the construct.

2. Preparation of CHO-K1 Cells Stably Expressing Human SGLT1 and Human SGLT2:

Transfection of CHO-K$^1$ cells was performed using 2.5 ug of pSPI1-SGLT1 or pSPI1-SGLT2 plasmid with about 6 ul of Lipofectamin 2000 (Invitrogen, Cat. #: 11668-019) in about 1.5×10$^5$ CHO-K1 cells using 12-well cell culture plate (Becton Dickinson, Cat. #: 353003) in the presence of DMEM medium (Dulbecco's Modified Eagle Medium) (Gibco, Cat. #: 11885-092) containing 10% FBS (Sigma, Cat. #: F1051-500mL). Transfectants were then selected in the presence of the antibiotic G418 (GIBCO, Cat. #: 11811-031) at final concentration of 750 ug/ml. Individual clones for both SGLT1 and SGLT2 were then characterized using the functional cell-based assay described below.

3. Cell-Based Assay for Inhibition of Uptake of methyl-α-D-glucopyranoside by Human SGLT1 and Human SGLT2:

Selected cell lines stably expressing human SGLT1 or human SGLT2 were then used for functional analysis of sodium dependent glucose uptake. Sodium-dependent D-glucose transport was determined by measuring the uptake of 14C-methyl-α-D-glucopyranoside (14C-AMG) with a specific activity of 250-350mCi (9.25-13.0 GBq)/mmol (PerkinElmer, Cat. #: NEC 659250UC). The assay buffer used to assess sodium-dependent D-glucose transport was Krebs-Ringer-Henseleit (KRH) solution containing 4.7 mM KCl, 1.2 mM MgCl$_2$, 2.2 mM CaCl$_2$, 10 mM Hepes pH 7.4 with Tris (Sigma). For sodium (Na$^+$) conditions the Assay Buffer containing 120 mM NaCl (Na$^+$) was used to assess sodium-dependent D-glucose transport (KRH-Na$^+$). For sodium free conditions, KRH solution containing 120 mM N-methyl-glucamine (NMG) instead of NaCl (Na$^+$) was used to assess sodium-independent D-glucose transport (KRH-NMG). All buffer chemicals were purchased from Sigma.

In brief, the cells were plated at a density of 40,000 cells per well in a 96-well plate in DMEM media and allowed to grow for 24 hours. Cells were subsequently washed twice (2×100 μL) with KRH buffer cells containing NMG. Cells in each well were incubated with KRH-Na$^+$ or KRH-NMG buffer containing 5 μCi 14C-AMG, 50 μM AMG and treated with compounds and then incubated for 1 hour at 37° C. in a CO$_2$ incubator. After 1 hour the labeled cells were washed two times with KRH-Na or KRH-NMG containing 50 μM AMG. After aspiration, cells in each well were solubilized with 50 μL of lysis buffer by placing the 96-wellplate on a plate shaker for 5 min. Scintillation cocktail (1004) was added and the 14C-AMG radioisotope counted in a MicroBeta Trilux (PerkinElmer).

The results obtained are shown on the following tables:

| SGLT1 Data | |
|---|---|
| Compound | % Inhibition |
| Control | 0 |
| 100 μM 104 | 48 |
| 100 μM 100 | 46 |
| 10 μM 47 | 11 |
| 100 μM 47 | 40 |

| SGLT2 Data | |
|---|---|
| Compound | % Inhibition |
| Control | 0 |
| 10 μM 104 | 40 |
| 100 μM 104 | 56 |
| 10 μM 100 | 30 |
| 100 μM 100 | 79 |
| 10 μM 47 | 22 |
| 100 μM 47 | 58 |

The invention claimed is:

1. A compound of formula (I):

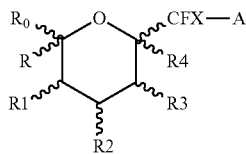

(I)

or a pharmaceutically acceptable addition salt thereof with organic and inorganic acid, a tautomer, an isomer or a mixture of isomers in any proportion,
wherein:
  X represents a fluorine atom;
  R represents $CH_2OH$;
  R1, R2 and R3 represent OH;
  R4 represents a hydrogen atom, an halogen atom or an OH or $OR^{11}$ group;
  $R_0$ represents a hydrogen atom or OH; and
  A represents an aryl or aryl-$(C_1-C_6)$-alkyl-aryl group, optionally substituted with one or more groups chosen among an halogen atom, a CN, $SO_2$, $SiR^aR^bR^c$, $(C_1-C_6)$-alkyl, $(C_1-C_6)$-alkenyl, $(C_2-C_6)$-alkynyl, $(C_3-C_7)$-cycloalkyl, 5 to 7 ring-membered heterocycloalkyl, aryl, heteroaryl, aryl-$(C_1-C_6)$-alkyl, heteroaryl-$(C_1-C_6)$-alkyl, $(C_1-C_6)$-alkyl-aryl, $(C_1-C_6)$-alkyl-heteroaryl, $OR^{11}$, $COR^{11}$, $OCOR^{11}$, $CO_2R^{11}$, $NR^{12}R^{13}$, $NR^{12}COR^{11}$, $CONR^{12}R^{13}$, $SR^{11}$, $SO_2R^{11}$, $CSR^{11}$ and $OSO_3R^{11}$ group,
  the whole being optionally substituted with one or more groups chosen among an halogen atom, an OH, $(C_1-C_6)$-alkyl, $(C_1-C_6)$-alkoxy, COOH and CHO group;
with:
  $R^{11}$ representing a $(C_1-C_6)$-alkyl, $(C_2-C_6)$-alkenyl, $(C_2-C_6)$-alkynyl, $(C_3-C_7)$-cycloalkyl, 5 to 7 ring-membered heterocycloalkyl, aryl, aryl-$(C_1-C_6)$-alkyl or $(C_1-C_6)$-alkyl-aryl group, this group being optionally substituted with one or more groups chosen among an halogen atom, an OH, COOH and CHO group;
  $R^{12}$ and $R^{13}$ representing, independently from one another, a hydrogen atom or a $(C_1-C_6)$-alkyl or aryl-$(C_1-C_6)$-alkyl group; and
  $R^a$, $R^b$ and $R^c$ representing, independently from one another, a $(C_1-C_6)$-alkyl, aryl or aryl-$(C_1-C_6)$-alkyl group;
with the proviso that when $R_0$ is different from a hydrogen atom, then R4 represents a hydrogen atom.

2. The compound according to claim 1, having the following formula (II) or (IIbis):

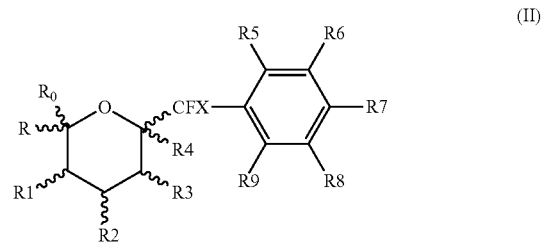

(II)

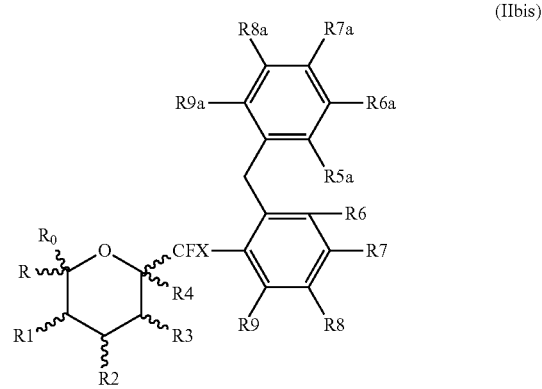

(IIbis)

wherein:
  R5, R6, R7, R8, R9, R5a, R6a, R7a, R8a and R9a represent, independently from one another, a hydrogen atom, an halogen atom, a CN, $SO_2$, $SiR^aR^bR^c$, $(C_1-C_6)$-alkyl, $(C_2-C_6)$-alkenyl, $(C_2-C_6)$-alkynyl, $(C_3-C_7)$-cycloalkyl, 5 to 7 ring-membered heterocycloalkyl, aryl, heteroaryl, aryl-$(C_1-C_6)$-alkyl, heteroaryl-$(C_1-C_6)$-alkyl, $(C_1-C_6)$-alkyl-aryl, $(C_1-C_6)$-alkyl-heteroaryl, $OR^{11}$, $COR^{11}$, $OCOR^{11}$, $CO_2R^{11}$, $NR^{12}R^{13}$, $NR^{12}COR^{11}$, $CONR^{12}R^{13}$, $SR^{11}$, $SO_2R^{11}$, $CSR^{11}$ or $OSO_3R^{11}$ group, the said group being optionally substituted with one or more groups chosen among an halogen atom, an OH, $(C_1-C_6)$-alkyl, $(C_1-C_6)$-alkoxy, COOH and CHO group, and
  X, R, R1, R2, R3, R4, $R_0$, $R^{11}$, $R^{12}$, $R^{13}$, $R^a$, $R^b$ and $R^c$ are as defined in claim 1.

3. The compound according claim 1, selected from the group consisting of:

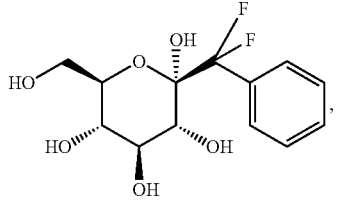

47-A

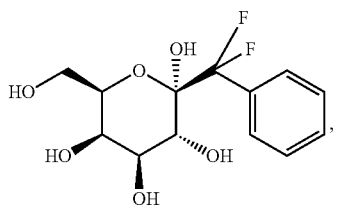

48-A

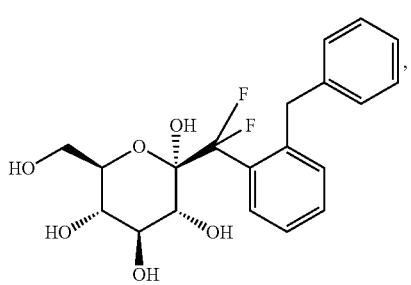

49-A

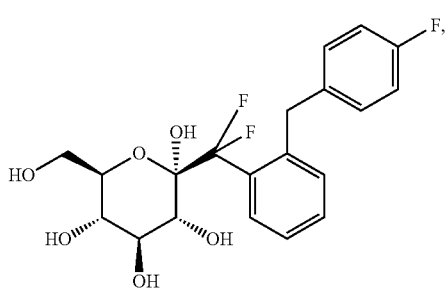

50-A

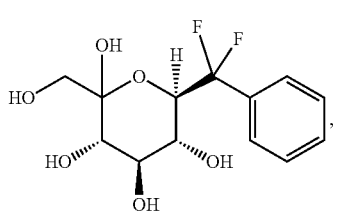

51

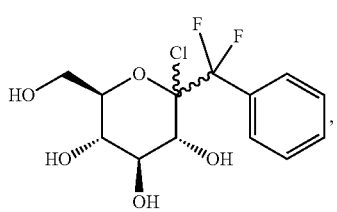

52

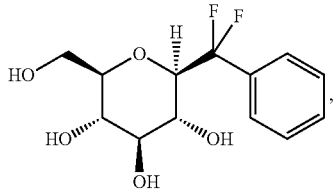

100

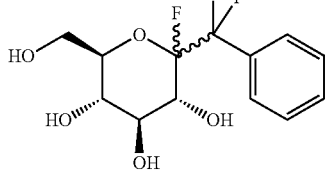

101d1/101d2

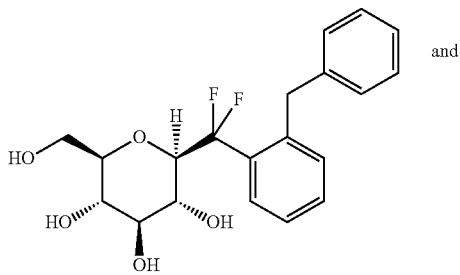

103 and

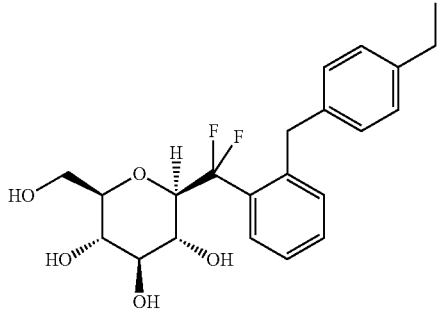

104

4. A method for treating diabetes comprising the administration to a person in need thereof of an effective amount of a compound according to claim 1.

5. A pharmaceutical or cosmetic composition including at least one compound as claimed in claim 1, and at least one pharmaceutically or cosmetically acceptable vehicle.

6. The pharmaceutical composition according to claim 5, wherein it includes at least one other antidiabetic agent.

7. A method of lightening the skin, bleaching the skin, depigmenting the skin, removing blemishes from the skin, or preventing pigmentation of the skin comprising the administration to a person in need thereof of an effective amount of a compound according to claim 1.

8. A process for preparing a compound of formula (I) as defined in claim 1, wherein R4 represents an OH group, according to the following steps:

(a) placing a compound of formula A-CFXX', wherein X and A are as defined in claim 1 and X' represents a bromine or chlorine atom, in the presence of a compound of formula (V):

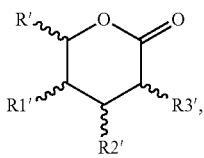

(V)

wherein:
R' represents a $CH_2OH$, $CH_2OSiR^aR^bR^c$, $CH_2OR^{11}$ or $CH_2OCOR^{11}$ group, R1' and R2' represent, independently from one another, an OH, $OSiR^aR^bR^c$, $OR^{11}$ or $OCOR^{11}$ group, and R3' represents an OH, $OSiR^aR^bR^c$, $OR^{11}$ or $OCOR^{11}$ group, or R' and R1', together with the carbon atoms carrying them, form a cyclic acetal having the following formula:

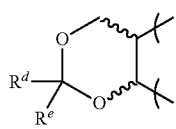

and/or (R2' and R3') or (R1' and R2'), together with the carbon atoms carrying them, form a cyclic acetal having the following formula:

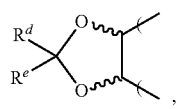

and (b) addition of a $(C_1\text{-}C_6)$-alkyl lithium to the mixture of step (a3) and optionally deprotection steps, in order to obtain a compound of formula (I) with $R^{11}$ representing a $(C_1\text{-}C_6)$-alkyl, $(C_2\text{-}C_6)$-alkenyl, $(C_2\text{-}C_6)$-alkynyl, $(C_3\text{-}C_7)$-cycloalkyl, 5 to 7 ring-membered heterocycloalkyl, aryl, aryl-$(C_1\text{-}C_6)$-alkyl or $(C_1\text{-}C_6)$-alkyl-aryl group, this group being optionally substituted with one or more groups chosen among an halogen atom, an OH, COOH and CHO group;

$R^a$, $R^b$ and $R^c$ representing, independently from one another, a $(C_1\text{-}C_6)$-alkyl, aryl or aryl-$(C_1\text{-}C_6)$-alkyl group; and $R^d$ and $R^e$ representing, independently from one another, a hydrogen atom or a $(C_1\text{-}C_6)$-alkyl group.

9. A process for preparing a compound of formula (I) as claimed in claim 1, wherein R4 represents $OR^{11}$, wherein the compound of formula (I) is obtained by substitution of the OH group of a compound of formula (Ib) below:

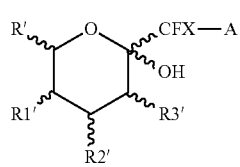

(Ib)

wherein:
R' represents a $CH_2OH$, $CH_2OSiR^aR^bR^c$, $CH_2OR^{11}$ or $CH_2OCOR^{11}$ group, R1' and R2' represent, independently from one another, an OH, $OSiR^aR^bR^c$, $OR^{11}$ or $OCOR^{11}$ group, and R3' represents an OH, $OSiR^aR^bR^c$, $OR^{11}$ or $OCOR^{11}$ group, or R' and R1', together with the carbon atoms carrying them, form a cyclic acetal having the following formula:

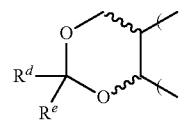

and/or (R2' and R3') or (R1' and R2'), together with the carbon atoms carrying them, form a cyclic acetal having the following formula:

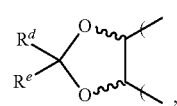

$R^{11}$ representing a $(C_1\text{-}C_6)$-alkyl, $(C_2\text{-}C_6)$-alkenyl, $(C_2\text{-}C_6)$-alkynyl, $(C_3\text{-}C_7)$-cycloalkyl, 5 to 7 ring-membered heterocycloalkyl, aryl, aryl-$(C_1\text{-}C_6)$-alkyl or $(C_1\text{-}C_6)$-alkyl-aryl group, this group being optionally substituted with one or more groups chosen among an halogen atom, an OH, COOH and CHO group;

$R^a$, $R^b$ and $R^c$ representing, independently from one another, a $(C_1\text{-}C_6)$-alkyl, aryl or aryl-$(C_1\text{-}C_6)$-alkyl group;

$R^d$ and $R^e$ representing, independently from one another, a hydrogen atom or a $(C_1\text{-}C_6)$-alkyl group, and optionally deprotection steps.

10. A process for preparing a compound of formula (II) as defined in claim 2, wherein $R_0$=H, wherein the compound of formula (II) is obtained by fluorination of a compound of the following formula (VIIa):

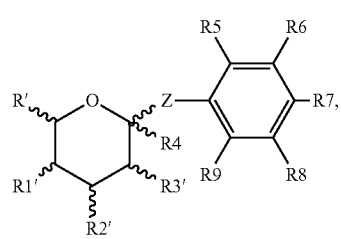

(VIIa)

wherein:
R' represents a $CH_2OH$, $CH_2OSiR^aR^bR^c$, $CH_2OR^{11}$ or $CH_2OCOR^{11}$ group, R1' and R2' represent, independently from one another, an OH, OSiR$^a$R$^b$R$^e$, OR$^{11}$ or OCOR$^{11}$ group, and
R3' represents an OH, OSiR$^a$R$^b$R$^c$, OR$^{11}$ or OCOR$^{11}$ group,
or R' and R1', together with the carbon atoms carrying them, form a cyclic acetal having the following formula:

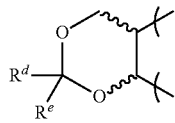

and/or (R2' and R3') or (R1' and R2'), together with the carbon atoms carrying them, form a cyclic acetal having the following formula:

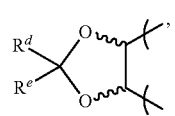

R5, R6, R7, R8 R9, R11, R$^a$, R$^b$ and R$^c$ are as defined in claim 2,
Z represents a C=O, CHOH or C(SR$^{15}$)(SR$^{16}$) group, with R15 and R16 representing, independently of each other, a (C$_1$-C$_6$)-alkyl group or forming together an hydrocarbon chain of formula —CH$_2$—(CH$_2$)$_p$—, with p=1 or 2, between the two sulphur atoms, and
R$^d$ and R$^e$ representing, independently from one another, a hydrogen atom or a (C$_1$-C$_6$)-alkyl group;
and optionally deprotection steps.

11. A compound of the following formula (VII):

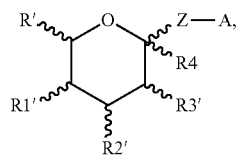

or a pharmaceutically acceptable addition salt thereof with organic and inorganic acid, a tautomer, an isomer or a mixture of isomers in any proportions,
wherein:
R' represents a CH$_2$OH, CH$_2$OSiR$^a$R$^b$R$^c$, CH$_2$OR$^{11}$ or CH$_2$OCOR$^{11}$ group;
R1' and R2' represent, independently from one another, an OH, OSiR$^a$R$^b$R$^c$, OR$^{11}$ or OCOR$^{11}$ group;
R3' represents an OH, OSiR$^a$R$^b$R$^c$, OR$^{11}$ or OCOR$^{11}$ group;
or R' and R1', together with the carbon atoms carrying them, form a cyclic acetal having the following formula:

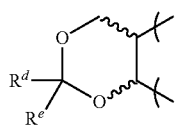

and/or (R2' and R3') or (R1' and R2'), together with the carbon atoms carrying them, form a cyclic acetal having the following formula:

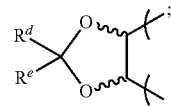

A represents an aryl or aryl-(C$_1$-C$_6$)-alkyl-aryl group, optionally substituted with one or more groups chosen among an halogen atom, a CN, SO$_2$, SiR$^a$R$^b$R$^c$, (C$_1$-C$_6$)-alkyl, (C$_1$-C$_6$)-alkenyl, (C$_2$-C$_6$)-alkynyl, (C$_3$-C$_7$)-cycloalkyl, 5 to 7 ring-membered heterocycloalkyl, aryl, heteroaryl, aryl-(C$_1$-C$_6$)-alkyl, heteroaryl-(C$_1$-C$_6$)-alkyl, (C$_1$-C$_6$)-alkyl-aryl, (C$_1$-C$_6$)-alkyl-heteroaryl, OR$^{11}$, COR$^{11}$, OCOR$^{11}$, CO$_2$R$^{11}$, NR$^{12}$R$^{13}$, NR$^{12}$COR$^{11}$, CONR$^{12}$R$^{13}$, SR$^{11}$, SO$_2$R$^{11}$, CSR$^{11}$ and OSO$_3$R$^{11}$ group,
the whole being, optionally substituted with one or more groups chosen among an halogen atom, an OH, (C$_1$-C$_6$)-alkyl, (C$_1$-C$_6$)-alkoxy, COOH and CHO group; and
Z represents a C=O, CHOH or C(SR$^{15}$)(SR$^{16}$) group; with:
R$^{11}$ representing a (C$_1$-C$_6$)-alkyl, (C$_2$-C$_6$)-alkenyl, (C$_2$-C$_6$)-alkynyl, (C$_3$-C$_7$)-cycloalkyl, 5 to 7 ring-membered heterocycloalkyl, aryl, aryl-(C$_1$-C$_6$)-alkyl or (C$_1$-C$_6$)-alkyl-aryl group, this group being optionally substituted with one or more groups chosen among an halogen atom, an OH, COOH and CHO group;
R$^{12}$ and R$^{13}$ representing, independently from one another, a hydrogen atom or (C$_1$-C$_6$)-alkyl or aryl-(C$_1$-C$_6$)-alkyl group;
R$^a$, R$^b$ and R$^c$ representing, independently from one another, a (C$_1$-C$_6$)-alkyl, aryl or aryl-(C$_1$-C$_6$)-alkyl group;
R$^d$ and R$^e$ representing, independently from one another, a hydrogen atom or a (C$_1$-C$_6$)-alkyl group; and R$^{15}$ and R$^{16}$ representing, independently of each other, a (C$_1$-C$_6$)-alkyl group or forming together an hydrocarbon chain of formula —CH$_2$—(CH$_2$)$_p$—, with p=1 or 2, between the two sulphur atoms.

12. The compound according to claim 11, of formula (VIIa) or (VIIb):

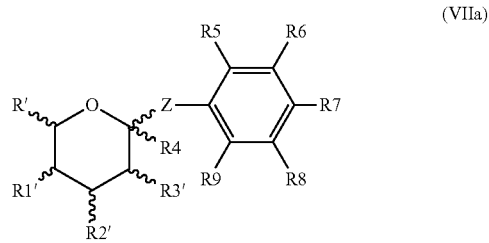

-continued

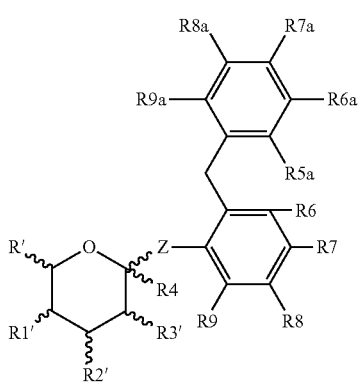
(VIIb)

wherein
R' represents a CH$_2$OH, CH$_2$OSiR$^a$R$^b$R$^c$, CH$_2$OR$^{11}$ or CH$_2$OCOR$^{11}$ group;
R1' and R2' represent, independently from one another, an OH, OSiR$^a$R$^b$R$^c$, OR$^{11}$ or OCOR$^{11}$ group;
R3' represents an OH, OSiR$^a$R$^b$R$^c$, OR$^{11}$ or OCOR$^{11}$ group;
R4 represents a hydrogen atom, an halogen atom or an OH or OR$^{11}$ group;
R5, R6, R7, R8, R9, R5a, R6a, R7a, R8a and R9a represent, independently from one another, a hydrogen atom, an halogen atom, a CN, SO$_2$, SiR$^a$R$^b$R$^c$, (C$_1$-C$_6$)-alkyl, (C$_2$-C$_6$)-alkenyl, (C$_2$-C$_6$)-alkynyl, (C$_3$-C$_7$)-cycloalkyl, 5 to 7 ring-membered heterocycloalkyl, aryl, heteroaryl, aryl-(C$_1$-C$_6$)-alkyl, heteroaryl-(C$_1$-C$_6$)-alkyl, (C$_1$-C$_6$)-alkyl-aryl, (C$_1$-C$_6$)-alkyl-heteroaryl, OR$^{11}$, COR$^{11}$, OCOR$^{11}$, CO$_2$R$^{11}$, NR$^{12}$R$^{13}$, NR$^{12}$COR$^{11}$, CONR$^{12}$R$^{13}$, SR$^{11}$, SO$_2$R$^{11}$, CSR$^{11}$ or OSO$_3$R$^{11}$ group, the said group being optionally substituted with one or more groups chosen among an halogen atom, an OH, (C$_1$-C$_6$)-alkyl, (C$_1$-C$_6$)-alkoxy, COOH and CHO group; and
Z represents a C=O, CHOH or C(SR$^{15}$)(SR$^{16}$) group with R$^{15}$ and R$^{16}$ representing, independently of each other, a (C$_1$-C$_6$)-alkyl group or forming together an hydrocarbon chain of formula —CH$_2$—(CH$_2$)$_p$—, with p=1 or 2, between the two sulphur atoms.

13. The compound according to claim 11, wherein it is chosen among:

57

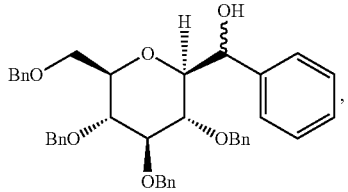

58

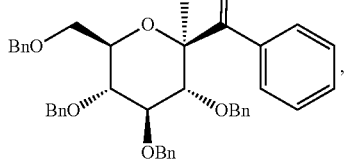

59

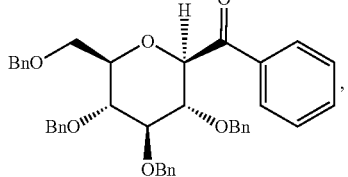

60

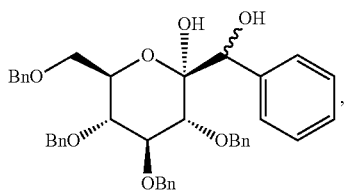

62

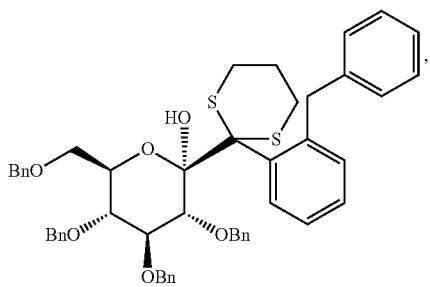

64

70

71

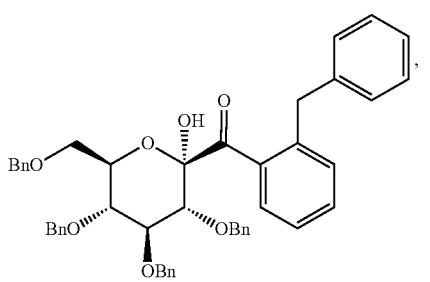

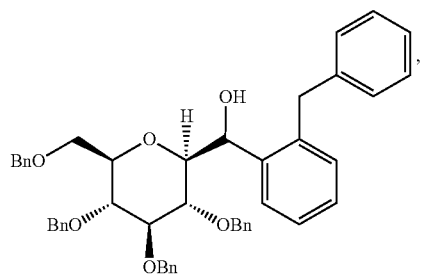
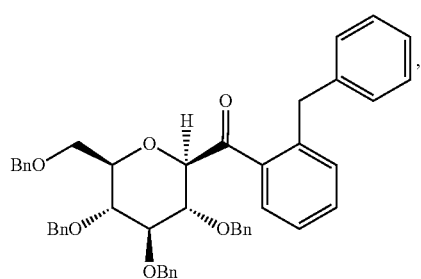
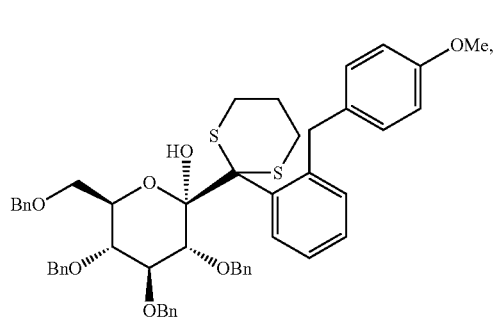
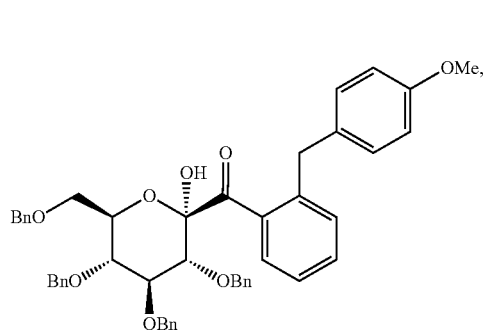
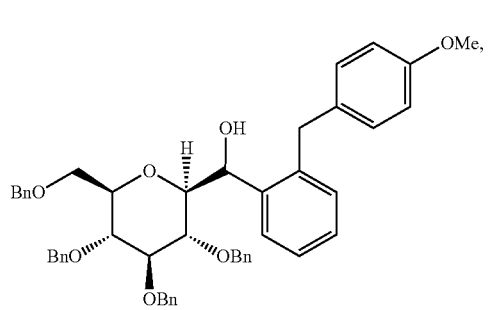
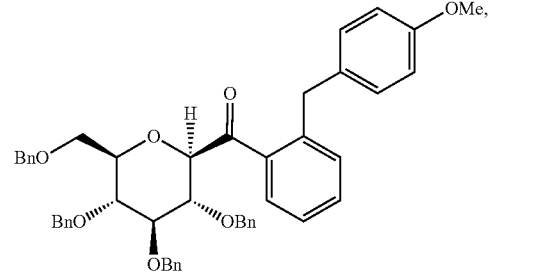
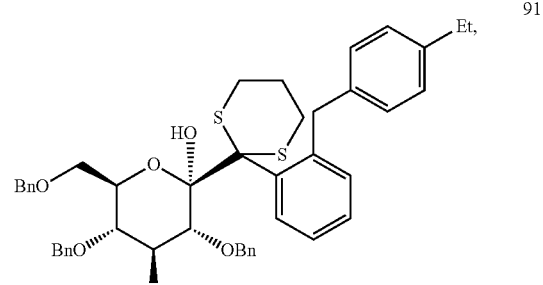
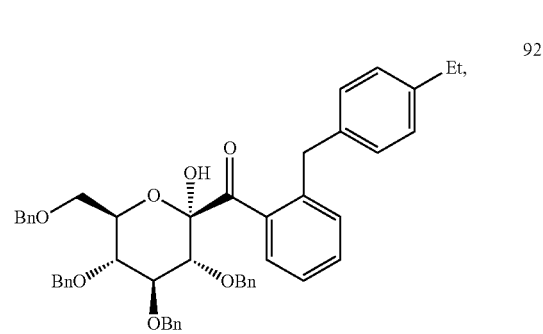
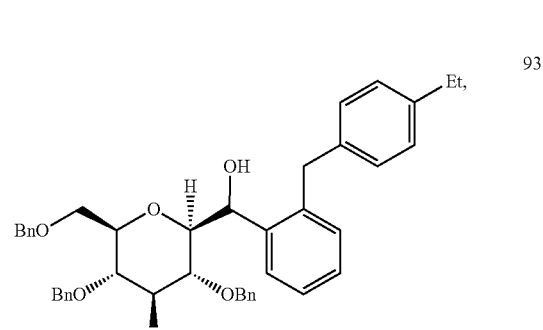
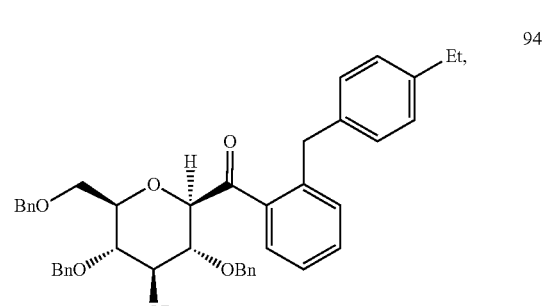

-continued

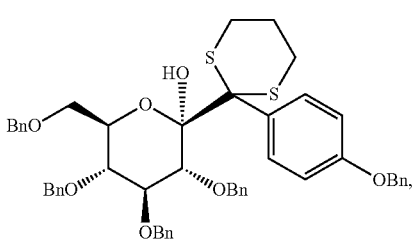
98

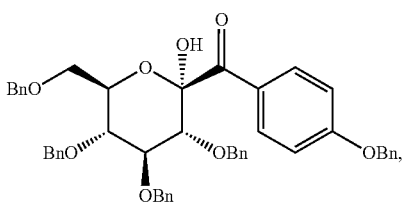
99

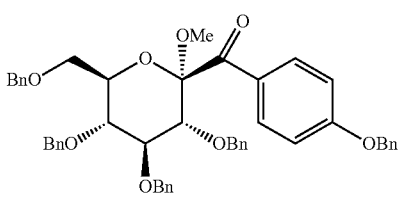
105
and

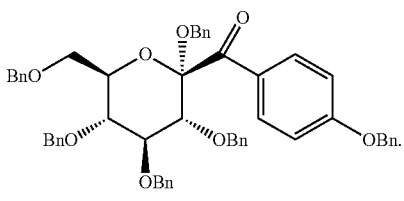
106

14. The compound according to claim 1, wherein the mixture of isomers is a racemate mixture.

15. The compound according to claim 11, wherein the mixture of isomers is a racemate mixture.

16. The method according to claim 4, wherein diabetes is type-II diabetes.

17. The pharmaceutical composition according to claim 6, wherein the antidiabetic agent is chosen among sulfonylurea-type compounds, thiazolidinediones, alpha-glucosidase inhibitors, meglitinides, incretin mimics, dipeptidylpeptidase-4 (DPP4) inhibitors and antilipidic agents.

18. The pharmaceutical composition according to claim 17, wherein the sulfonylurea-type compound is chosen among chlorpropamide, tolbutamide, tolazamide, glipizide, gliclazide, glibenclamide, gliquidone and glimepiride; the biguanide is metformine; the thiazolidinedione is chosen among rosiglitazone, pioglitazone and ciglitazone; the alpha-glucosidase inhibitor is chosen among acarbose, miglitol and voglibose; the meglitinide is chosen among repaglinide and nateglinide; the incretin mimic is exenatide; the dipeptidylpeptidase-4 (DPP4) inhibitor is chosen among sitagliptin, vildagliptin and insulin; and the antilipidic agent is chosen among statins, fibrates and ezetimibe.

19. The pharmaceutical composition according to claim 18, wherein the statin is chosen among atorvastatin and cerivastatin, and the fibrate is chosen among bezafibrate, gemfibrozil and fenofibrate.

* * * * *